(12) United States Patent
Morie et al.

(10) Patent No.: US 7,176,199 B2
(45) Date of Patent: Feb. 13, 2007

(54) ARYL-SUBSTITUTED ALICYCLIC COMPOUND AND MEDICAL COMPOSITION COMPRISING THE SAME

(75) Inventors: Toshiya Morie, Matsubara (JP); Seiji Iwama, Kishiwada (JP); Mitsue Notake, Suita (JP); Tomoko Kitano, Tondabayashi (JP)

(73) Assignee: Dainippon Pharmaceutical Co., Ltd., Osaka-Fu (JP)

( * ) Notice: Subject to any disclaimer, the term of this patent is extended or adjusted under 35 U.S.C. 154(b) by 318 days.

(21) Appl. No.: 10/472,236

(22) PCT Filed: Mar. 14, 2002

(86) PCT No.: PCT/JP02/02391

§ 371 (c)(1),
(2), (4) Date: Sep. 22, 2003

(87) PCT Pub. No.: WO02/074743

PCT Pub. Date: Sep. 26, 2002

(65) Prior Publication Data

US 2004/0106622 A1 Jun. 3, 2004

(30) Foreign Application Priority Data

Mar. 19, 2001 (JP) ............................... 2001-079029

(51) Int. Cl.
*C07D 239/14* (2006.01)
*C07D 233/50* (2006.01)
*C07D 401/14* (2006.01)
*A61K 31/506* (2006.01)
*C07D 413/14* (2006.01)

(52) U.S. Cl. .................. 514/218; 514/252.14; 514/269; 514/275; 514/326; 540/553; 544/298; 544/331; 544/332; 546/210

(58) Field of Classification Search ................ 544/298, 544/331, 332; 546/210; 540/553; 514/218, 514/252.14, 269, 275, 326
See application file for complete search history.

(56) References Cited

U.S. PATENT DOCUMENTS 5,990,145 A 11/1999 Wehner et al.
6,451,800 B1 9/2002 Ajito et al.

FOREIGN PATENT DOCUMENTS

| EP | 1074543 | 2/2001 |
| WO | 98/18461 | 5/1998 |
| WO | 00/06169 | 2/2000 |
| WO | 01/44230 | 6/2001 |
| WO | 01/96334 | 12/2001 |

OTHER PUBLICATIONS

Agrez et al., The alpha-v-beta-6 Integrin induces gelatinase B secretion in colon cancer cells, Int. J. Cancer, 81, pp. 90-97, 1999.*

Brooks et al., Integrin alpha-v-beta-3: A therapeutic target, DN&P, 10(8), pp. 456-461, Oct. 1997.*

Gladson et al., Vitronectin Expression in Differentiating Neuroblastic Tumors, American Journal of Pathology, vol. 150, No. 5, pp. 1631-1646, May 1997.*

Kim et al., Vitronectin-driven Human Keratinocyte Locomotion Is Mediated by the alpha-v-beta-5 Integrin Receptor, The Journal of Biological Chemistry, vol. 269, No. 43, pp. 26928-26932, Oct. 1994.*

Nip et al., The role of the Integrin vitronectin receptor, alpha-v-beta-3 in melanoma metastasis, Cancer and Metastasis Reviews, 14, pp. 241-252, 1995.*

Raynal et al., Bone Sialoprotein Stimulates in vitro Bone Resorption, Endocrinology, vol. 137, No. 6, pp. 2347-2354, 1996.*

Schvartz et al., Vitronectin, The International Journal of Biochemistry & Cell Biology, 31, pp. 539-544, 1999.*

Simone, Oncology: Introduction, Cecil Textbook of Medicine, 20th Edition, vol. 1, pp. 1004-1010, 1996.*

Antonov et al., Medline Abstract (American Journal of Pathology, vol. 165, Issue 1, pp. 247-258) Jul. 2004.*

Douglas, Jr. Introduction to Viral Diseases, Cecil Textbook of Medicine, 20th Edition, vol. 2, pp. 1739-1747, 1996.*

West, Solid Solutions, Solid state chemistry and it's applications, Wiley, New York, pp. 358 and 365, 1988.*

Vippagunta et al., Crystalline solids, Advanced Drug Delivery Reviews, 48 (2001), pp. 3-26, 2001.*

J. Samanen et al., "Vascular Indications for Integrin αv Antagonists", Current Pharmaceutical Design, vol. 3, pp. 545-583, 1997.

W. Miller et al., "Identification and *in vivo* efficacy of small-molecule antagonists of integrin $α_vβ_e$ (the vitronectin receptor)", Drug Discovery Today, vol. 5, No. 9, pp. 397-408, 2000.

G. P. Curley et al., "Integrin Antagonists", Cell. Mol. Life Sci., vol. 56, pp. 427-441, 1999.

* cited by examiner

*Primary Examiner*—Deepak Rao
(74) *Attorney, Agent, or Firm*—Wenderoth, Lind & Ponack, L.L.P.

(57) ABSTRACT

An aryl-substituted alicyclic compound of the formula (I):

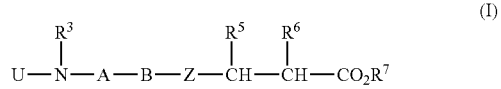

wherein U is 1,4,5,6-tetrahydropyrimidin-2-yl, etc., A is phenylene, etc., B is piperidine-1,4-diyl, etc., Z is —CONH—, etc., $R^3$ is hydrogen, etc., $R^5$ is hydrogen, aryl, etc., $R^6$ is a mono-substituted amino (e.g., benzyloxycarbonylamino), $R^7$ is hydrogen, etc., and a process for preparation thereof, and a pharmaceutical composition containing the same. The compound of the present invention has a high selectivity for αvβ3 integrin, and exhibits a potent inhibitory activity thereto, and hence, it is useful as a preventive or/and a therapeutic agent for a disease in which αvβ3 integrin is involved.

16 Claims, No Drawings

ARYL-SUBSTITUTED ALICYCLIC COMPOUND AND MEDICAL COMPOSITION COMPRISING THE SAME

This application is a U.S. national stage of International Application No. PCT/JP02/02391 filed Mar. 14, 2002.

TECHNICAL FIELD

The present invention relates to a novel aryl-substituted alicyclic compound having αvβ3 integrin inhibitory activity, etc., and a pharmaceutical composition containing the same.

BACKGROUND ART

Integrin is a family of receptors that have cell adhesion molecules as ligands, and mediate cell-to-cell and cell-to-extracellular matrix adhesions. Integrins directly participate in preservation of cell shape, anchorage for cell migration, and intra- and extracellular signal transduction. Therefore, integrins play important roles in a range of biological events including cell survival, movement, proliferation, development and differentiation.

Integrin is a heterodimeric transmembrane glycoprotein consisting of α and β chains. To date, various kinds of α and β chains have been known, and thus more than 20 integrins have been identified based on combination of the α and β chains (Trends Pharmacol., Sci., 21, 29 (2000)). In addition to the integrins, a number of cell adhesion molecules including, proteins that constitute extracellular matrix such as, collagen and vitronectin, proteins involved in immune and/or inflammatory cells adhesion such as, VCAM-1 and ICAM-1, and proteins involved in blood coagulation such as, fibrinogen and von Willebrand factor have been identified as integrin ligands (Cell, 69, 11 (1992)).

The αvβ3 integrin comprising αv- and β3-chains is also known as vitronectin receptor. Although vitronectin is the main ligand for αvβ3 integrin, some other proteins with RGD sequence such as fibronectin, fibrinogen and osteopontin are also known as αvβ3 integrin ligands.

It is known that αvβ3 integrin is expressed on a wide variety of adhesive cells. Among them, much attention has been given to the pathophysiological role of αvβ3 integrin expressed on cells where cell adhesion, migration, or proliferation is activated with the development of disease state. For example, after angioplasty, abnormal migration and proliferation of vascular smooth muscle cells often causes neointimal hyperplasia resulting in restenosis. Similarly, in cancer tissues, abnormal migration and proliferation of vascular endothelial cells accelerates angiogenesis. Moreover, it has been shown in animal models of progressive diseases that the expression of αvβ3 integrin is increased in defective cells, and that disease symptoms can be prevented by administration of antibodies or synthetic peptides which inhibit αvβ3 integrin (Curr. Pharm. Des., 3, 545 (1997)). Therefore, it is suggested that αvβ3 integrin may play an important role in the initiation and progression of restenosis and angiogenesis. Besides these two conditions, αvβ3 integrin has also been shown to be involved in other diseases including osteoporosis, rheumatoid arthritis, cancer metastasis, diabetic retinopathy, inflammatory diseases and viral infections (Curr. Biol., 3, 596 (1993); Cell. Mol. Life Sci., 56, 427 (1999); Drug Discovery Today, 5, 397 (2000)).

From the information above, it is assumed that inhibition of αvβ3 integrin might cure diseases that are accompanied with cells adhesion, migration or proliferation. Therefore, it is expected that αvβ3 integrin inhibitors may be useful as a novel type of antirestenotic agents, antiarteriosclerotic agents, anticancer agents, antiosteoporosis agents, antiinflammatory agents, antiimmune agents, and agents for eye diseases.

Beside αvβ3 integrin, αIIbβ3 integrin or GPIIb/IIIa, another integrin closely related to αvβ3 integrin, has been shown to be highly involved in platelet aggregation. As inhibitors of αvβ3 integrin that also suppress αIIbβ3 integrin may cause breeding adverse effects, and may be inappropriate for repeated administration, αvβ3 integrin inhibitors with high selectivity for αvβ3 integrin as opposed to αIIbβ3 integrin have long been desired.

As far as the present inventors know, no therapeutic agent with highly selective αvβ3 integrin inhibitory activity has, so far, been developed. Therefore, under the present situation where diseases that involve αvβ3 integrin have been increasing with the aging population, it is necessary to develop inhibitors with high selectivity for αvβ3 integrin as opposed to αIIbβ3 integrin.

To date, quite a lot of compounds having αvβ3 integrin inhibitory activity have been reported (cf. U.S. Pat. No. 5,990,145, WO 98/18461, WO 99/38849, WO99/52872, etc.) For example, WO 99/38849 discloses (2S)-2-benzenesulfonylamino-3-[3-chloro-4-[4-(1,4,5,6-tetrahydropyrimidin-2-yl)piperazin-1-yl]benzoylamino]propanoic acid represented by the following formula (A-1, Example 59), and it reports that this compound has a potent αvβ3 integrin inhibitory activity ($IC_{50}$ value: 3.5 nM) and GPIIb/IIIa inhibitory activity ($IC_{50}$ value: 0.2 nM or less).

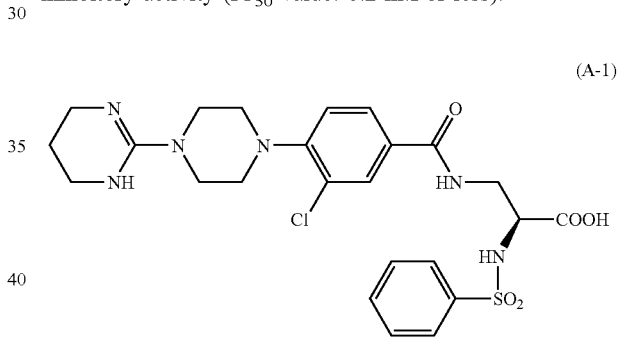

(A-1)

In addition, WO 99/52872 discloses (2S)-2-benzenesulfonylamino-3-[3-fluoro-4-[[4-(1,4,5,6-tetrahydropyrimidin-2-yl)amino]-piperidin-1-yl]benzoylamino]propanoic acid represented by the following formula (A-2, Example 52), and it reports that this compound has a potent αvβ3 integrin inhibitory activity ($IC_{50}$ value: 1.0 nM or less) and GPIIb/IIIa inhibitory activity ($IC_{50}$ value: 1.0 nM or less).

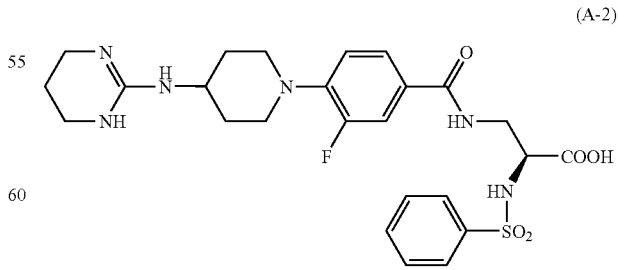

(A-2)

However, the chemical structures of these compounds are completely different from those of the compounds of the present invention as described below, and these compounds have a potent GPIIb/IIIa inhibitory activity, which is also different from the compounds of the present invention.

The present inventors have intensively studied, and have found that a novel aryl-substituted alicyclic compound of the formula (I) has a potent αvβ3 integrin inhibitory activity, and that it is useful as a preventive or therapeutic agent for diseases with which αvβ3 integrin is involved, and have accomplished the present invention.

DISCLOSURE OF INVENTION

The present invention provides an aryl-substituted alicyclic compound of the following formula (I), a prodrug thereof, a pharmaceutically acceptable salt thereof or an N-oxide derivative thereof, or a hydrate or a solvate thereof, a process for preparing these compounds, and a pharmaceutical composition containing the same.

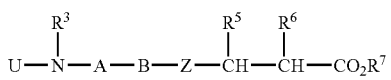

wherein U is a group of the following formula:

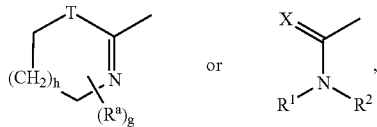

A is a group of the following formula:

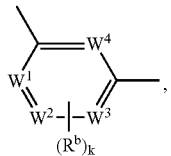

B is a group of the following formula:

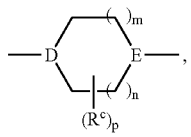

Z is —CONR$^4$(CH$_2$)$_q$—, —NR$^4$CO(CH$_2$)$_q$— or —COCH$_2$(CH$_2$)$_q$—,

T is —CH$_2$—, an oxygen atom, a sulfur atom or —NR$^d$—,

X is an oxygen atom or a sulfur atom,

W$^1$, W$^2$, W$^3$ and W$^4$ are the same or different, and each is —CH— or a nitrogen atom, D and E are the same or different, and each is —CH— or a nitrogen atom, R$^a$ is the same or different, and each is a hydrogen atom, a halogen atom, a hydroxy group, a C$_{1-6}$ alkyl group, a C$_{3-7}$ cycloalkyl group, a C$_{2-6}$ alkenyl group, a C$_{2-6}$ alkynyl group, an aryl group, an aralkyl group, a C$_{1-6}$ alkyloxy group, a C$_{1-6}$ alkyloxycarbonyl group, a formyl group, a C$_{1-6}$ alkylcarbonyl group, a carboxyl group, a C$_{1-6}$ alkylcarbonyloxy group, an amino group, a C$_{1-3}$ alkylamino group, a di(C$_{1-3}$ alkyl)amino group, a formylamino group, a C$_{1-3}$ alkylcarbonylamino group, an arylcarbonylamino group, a nitro group, a cyano group, a trifluoromethyl group, a trifluoromethoxy group or a trifluoroethoxy group, or when two R$^a$ groups attach to the same carbon atom, then they combine to form an oxo group or a thioxo group, or together with said carbon atom to form a spiro ring, R$^b$ is the same or different, and each is a hydrogen atom, a halogen atom, a hydroxy group, a C$_{1-6}$ alkyl group, a C$_{3-7}$ cycloalkyl group, a C$_{2-6}$ alkenyl group, a C$_{2-6}$ alkynyl group, an aryl group, an aralkyl group, a C$_{1-6}$ alkyloxy group, a C$_{1-6}$ alkyloxycarbonyl group, a formyl group, a C$_{1-6}$ alkylcarbonyl group, a carboxyl group, a C$_{1-6}$ alkylcarbonyloxy group, an amino group, a C$_{1-3}$ alkylamino group, a di(C$_{1-3}$ alkyl)amino group, a formylamino group, a C$_{1-3}$ alkylcarbonylamino group, an arylcarbonylamino group, a nitro group, a cyano group, a trifluoromethyl group, a trifluoromethoxy group or a trifluoroethoxy group, R$^c$ is the same or different, and each is a hydrogen atom, a halogen atom, a hydroxy group, a C$_{1-6}$ alkyl group, a C$_{3-7}$ cycloalkyl group, a C$_{2-6}$ alkenyl group, a C$_{2-6}$ alkynyl group, an aryl group, an aralkyl group, a C$_{1-6}$ alkyloxy group, a C$_{1-6}$ alkyloxycarbonyl group, a formyl group, a C$_{1-6}$ alkylcarbonyl group, a carboxyl group, a C$_{1-6}$ alkylcarbonyloxy group, an amino group, a C$_{1-3}$ alkylamino group, a di(C$_{1-3}$ alkyl)amino group, a formylamino group, a C$_{1-3}$ alkylcarbonylamino group, an arylcarbonylamino group, a nitro group, a cyano group, a trifluoromethyl group, a trifluoromethoxy group or a trifluoroethoxy group, or two R$^c$ groups may combine to form —(CR$^8$R$^9$)$_t$—, R$^d$ is a hydrogen atom, a C$_{1-6}$ alkyl group, a C$_{3-7}$ cycloalkyl group, a C$_{2-6}$ alkenyl group, a C$_{2-6}$ alkynyl group, an aryl group, an aralkyl group, a formyl group, a C$_{1-6}$ alkylcarbonyl group or a C$_{1-6}$ alkyloxycarbonyl group, R$^1$ and R$^2$ are the same or different, and each is a hydrogen atom, a C$_{1-10}$ alkyl group, a C$_{3-7}$ cycloalkyl group, a C$_{2-6}$ alkenyl group, a C$_{2-6}$ alkynyl group, an aryl group, an aralkyl group, a C$_{1-6}$ alkylcarbonyl group, a C$_{1-6}$ alkyloxycarbonyl group, a C$_{1-6}$ alkylsulfonyl group or an arylsulfonyl group, or R$^1$ and R$^2$ may combine to form —(CR$^{10}$R$^{11}$)$_u$— or —(CH$_2$)$_v$Y(CH$_2$)$_w$—, R$^3$ and R$^4$ are the same or different, and each is a hydrogen atom, a C$_{1-6}$ alkyl group, a C$_{3-7}$ cycloalkyl group, a C$_{2-6}$ alkenyl group, a C$_{2-6}$ alkynyl group, an aryl group or an aralkyl group, R$^5$ is a hydrogen atom, a halogen atom, a C$_{1-6}$ alkyl group, a C$_{3-7}$ cycloalkyl group, a C$_{2-6}$ alkenyl group, a C$_{2-6}$ alkynyl group, an aryl group or an aralkyl group, R$^6$ is a hydrogen atom, a halogen atom, a hydroxy group, a C$_{1-6}$ alkyl group, a C$_{3-7}$ cycloalkyl group, a C$_{2-6}$ alkenyl group, a C$_{2-6}$ alkynyl group, an aryl group, an aralkyl group, a C$_{1-6}$ alkyloxy group, a C$_{3-7}$ cycloalkyloxy group, a C$_{2-6}$ alkenyloxy group, a C$_{2-6}$ alkynyloxy group, an aryloxy group, an aralkyloxy group, a C$_{1-6}$ alkylcarbonyloxy group, a C$_{3-7}$ cycloalkylcarbonyloxy group, a C$_{2-6}$ alkenylcarbonyloxy group, a C$_{2-6}$ alkynylcarbonyloxy group, an arylcarbonyloxy group, an aralkylcarbonyloxy group, an amino group or a monosubstituted amino group (in which the substituent is a formyl, a C$_{1-10}$ alkylcarbonyl, a C$_{3-7}$ cycloalkylcarbonyl, a C$_{2-10}$ alkenylcarbonyl, a C$_{2-10}$ alkynylcarbonyl, an arylcarbonyl, an aralkylcarbonyl, a $C_{7-15}$ polycyclo-$C_{0-3}$ alkylcarbonyl, a $C_{1-16}$ alkyloxycarbonyl, a polyfluoro-$C_{1-16}$ alkyloxycarbonyl, a $C_{3-7}$ cycloalkyloxycarbonyl, a $C_{2-16}$ alkenyloxycarbonyl, a $C_{2-16}$ alkynyloxycarbonyl, an aryloxycarbonyl, a $C_{3-7}$ cycloalkyl-$C_{1-6}$ alkyloxycarbonyl, an aralkyloxycarbonyl, a $C_{1-10}$ alkylaminocarbonyl, a $C_{3-7}$ cycloalkylaminocarbonyl, a $C_{2-10}$ alkenylaminocarbonyl, a $C_{2-10}$ alkynylaminocarbonyl, an arylaminocarbonyl, an aralkylaminocarbonyl, a $C_{1-10}$ alkylsulfonyl, a $C_{3-7}$ cycloalkylsulfonyl, a $C_{2-10}$ alkenylsulfonyl, a $C_{2-10}$ alkynylsulfonyl, an arylsulfonyl, an aralkylsulfonyl, a $C_{7-15}$ polycyclo-$C_{0-3}$ alkylsulfonyl, a $C_{1-10}$ alkylaminosulfonyl, a $C_{3-7}$ cycloalkylaminosulfonyl, a $C_{2-10}$ alkenylaminosulfonyl, a $C_{2-10}$ alkynylaminosulfonyl, an arylaminosulfonyl or an aralkylaminosulfonyl), $R^7$ is a hydrogen atom, a $C_{1-6}$ alkyl group, a $C_{3-7}$ cycloalkyl group, an aryl group or an aralkyl group, $R^8$, $R^9$, $R^{10}$ and $R^{11}$ are the same or different, and each is a hydrogen atom, a $C_{1-3}$ alkyl group or an aryl group, Y is an oxygen atom, a sulfur atom or —$NR^{12}$—, $R^{12}$ is a hydrogen atom, a $C_{1-6}$ alkyl group, a $C_{3-7}$ cycloalkyl group, a $C_{2-6}$ alkenyl group, a $C_{2-6}$ alkynyl group, an aryl group, an aralkyl group, a $C_{1-6}$ alkylcarbonyl group or a $C_{1-6}$ alkyloxycarbonyl group, g is an integer of 1 to 4,
h is an integer of 0 to 3,
k is an integer of 1 to 3,
m and n are the same or different, and each is an integer of 0 to 3, but the sum of m and n should be an integer of 1 to 3,
p is an integer of 1 to 4,
q is 0 or 1,
t is an integer of 1 to 3,
u is an integer of 3 to 7,
v and w are the same or different, and each is an integer of 1 to 4, but the sum of v and w should be an integer of 2 to 6, provided that (i) when E is a nitrogen atom, then Z is —$CONR_4(CH_2)_q$— or —$COCH_2(CH_2)_q$—, (ii) in the above definition, the alkyl group, the cycloalkyl group, the alkenyl group, the alkynyl group, and the alkyl moiety of the aralkyl group may optionally be substituted by 1 to 3 atoms or groups selected from a halogen, a $C_{1-6}$ alkyloxy, an amino and a hydroxy, and the aryl group and the aryl moiety may optionally be substituted by 1 to 5 atoms or groups selected from a halogen, a $C_{1-6}$ alkyl, a $C_{3-7}$ cycloalkyl, an aryl, an aralkyl, an amino, an amino-$C_{1-6}$ alkyl, a formylamino, a $C_{1-3}$ alkylcarbonylamino, a $C_{1-6}$ alkylamino, a $C_{1-6}$ alkylamino-$C_{1-6}$ alkyl, a di($C_{1-6}$ alkyl)amino, a di($C_{1-6}$ alkyl) amino-$C_{1-6}$ alkyl, an arylcarbonylamino, a $C_{1-6}$ alkylaminocarbonylamino, an arylaminocarbonylamino, a $C_{1-4}$ alkyloxy, a $C_{1-4}$ alkylthio, a $C_{1-4}$ alkylsulfonyl, a $C_{1-4}$ alkyloxy-$C_{1-6}$ alkyl, a carboxyl, a carboxyl-$C_{1-6}$ alkyl, a $C_{1-4}$ alkyloxycarbonyl, a hydroxy, a hydroxy-$C_{1-6}$ alkyl, a cyano, a trifluoromethyl, a trifluoromethoxy, a $C_{1-4}$ alkylcarbonyloxy and a nitro.

The prodrug of the compound of the formula (I) means a compound of the formula (I) wherein $R^7$ is a hydrogen atom, and the carboxyl group is modified, said modified carboxyl group being converted into a carboxyl group by enzymatically or chemical cleavage in a living body, for example, such as compounds having an esterified carboxyl group. The esterified carboxyl group is preferably ones being used in the preparation of prodrugs in the pharmaceutical field, for example, a $C_{1-6}$ alkyloxycarbonyl group, a $C_{3-7}$ cycloalkyloxycarbonyl group, an aryloxycarbonyl group, an aralkyloxycarbonyl group, an optionally substituted $C_{1-3}$ alkyloxycarbonyl group (the substituent is selected from a carboxyl, a $C_{1-3}$ alkyloxycarbonyl, a $C_{1-3}$ alkylaminocarbonyl, a di($C_{1-3}$ alkyl)aminocarbonyl, a $C_{1-3}$ alkylamino, a di($C_{1-3}$ alkyl) amino, a $C_{1-3}$ alkyloxy or a dioxolenyl), or a group: —COO-$CHR^eOCOR^f$ ($R^e$ is a $C_{1-3}$ alkyl group, and $R^f$ is a $C_{1-6}$ alkyl group, a $C_{3-7}$ cycloalkyl group, an aryl group, an aralkyl group, a $C_{1-6}$ alkyloxy group, a $C_{3-7}$ cycloalkyloxy group, an aryloxy group or an aralkyloxy group). Besides, it is apparent that the compound of the formula (I) wherein $R^7$ is other than a hydrogen atom may fall under the category of prodrug. Suitable examples of prodrug are hereinafter disclosed.

The pharmaceutically acceptable salt of the compound of the formula (I) includes a pharmaceutically acceptable acid addition salt of the compound of the formula (I) having a group being capable of producing an acid addition salt within the structure thereof or a prodrug thereof, or a pharmaceutically acceptable salt with a base of the compound of the formula (I) having a group being capable of producing a salt with a base within the structure thereof or a prodrug thereof. Suitable acid addition salts are, for example, a salt with an inorganic acid such as hydrochloride, hydrobromide, hydroiodide, sulfate, perchlorate, phosphate, etc., and a salt with an organic acid such as oxalate, malonate, maleate, fumarate, lactate, malate, citrate, tartrate, benzoate, trifluoroacetate, acetate, methanesulfonate, p-toluenesulfonate, trifluoromethanesulfonate, etc., an amino acid salt such as glutamate, aspartate, etc. Suitable example of a salt with a base are such as an alkali metal salt or an alkaline earth metal salt (e.g., sodium salt, potassium salt, calcium salt, etc.), a salt with an organic base (e.g., pyridine salt, triethylamine salt, etc.), a salt with an amino acid (e.g., a salt with lysine, arginine, etc.). The N-oxide derivative of the compound of the formula (I) means an N-oxide derivative of the compound of the formula (I) having a pyridine nucleus.

The compound of the formula (I), or a prodrug thereof, or a salt thereof, and an N-oxide derivative thereof (hereinafter, occasionally referred to as the compound of the formula (1)) may exist in the form of a hydrate or a solvate, and these hydrates and solvates are also included in the compounds of the present invention. Further, the compound of the formula (I) may optionally have one or more asymmetric carbon atoms, and may have isomerism. Therefore, the compound of the formula (I) may exist in the form of several stereoisomers, and these stereoisomers, a mixture thereof and racemic compounds thereof are also included in the compound of the present invention.

The compound of the formula (I) wherein U is a group of the following formula:

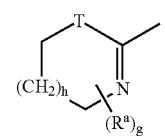

(wherein T, $R^a$, g and h are as defined above), and $R^3$ is a hydrogen atom may exist in the form of a tautomer of the following formula ($I_t$), and the present compound also includes the tautomer thereof. In the present specification, the compound of the present invention is expressed by the notational system of the formula (Is).

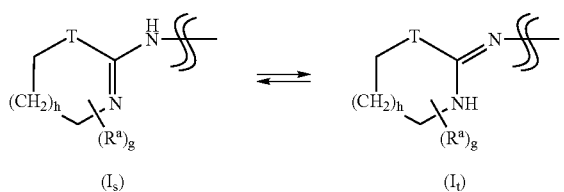

(the group A and the substructure succeeding therefrom of the compounds of the formulae ($I_s$) and ($I_t$) are omitted in the above formula. T, $R^a$, g and h are as defined above)

The terms in the present specification are explained below.

In the present specification, the number of the carbon atoms is defined such as "$C_{1-6}$ alkylcarbonyloxy", and the number of the carbon atoms is applied to only the group or moiety immediately following thereto. Therefore, in the above case, since $C_{1-6}$ indicate only the number of carbon atom of the alkyl, and hence, "$C^1$ alkylcarbonyloxy" means acetoxy.

Further groups: $R^a$, $R^{a1}$, $R^{a2}$, $R^c$, $R^{c1}$, $R^{c2}$, $R^{c3}$ and $R^{c4}$ may attach to any position, for example, when T, $T^1$ and $T^2$ are —$CH_2$—, then $R^a$, $R^{a1}$ or $R^{a2}$ may attach to said carbon atom in place of a hydrogen atom.

The alkyl group and the alkyl moiety may be either a straight chain or a branched chain.

The "halogen atom" is fluorine, chlorine, bromine, iodine, and preferable one is fluorine or chlorine, and especially preferable one is fluorine.

The "$C_{1-16}$ alkyl" is, for example, methyl, ethyl, propyl, isopropyl, butyl, isobutyl, sec-butyl, tert-butyl, pentyl, isopentyl, neopentyl, hexyl, octyl, nonyl, 3,7-dimethyloctyl, decyl, hexadecyl, etc.

The "$C_{3-7}$ cycloalkyl" is, for example, cyclopropyl, cyclobutyl, cyclopentyl, cyclohexyl, cycloheptyl. The "$C_{2-16}$ alkenyl" includes either straight chain, branched chain or cyclic ones, having at least one double bond, for example, vinyl, allyl, 1-propenyl, isopropenyl, 1-, 2- or 3-butenyl, 2-, 3- or 4-pentenyl, 2-methyl-2-butenyl, 3-methyl-2-butenyl, 5-hexenyl, 2,6-dimethyl-1,5-heptadienyl, 2-hexadecenyl, 1-cyclopentenyl, 1-cyclohexenyl, and equivalents thereof.

The "$C_{2-16}$ alkynyl" may be either straight chain, branched chain or cyclic ones, having at least one triple bond, for example, ethynyl, 1- or 2-propynyl, 1-, 2- or 3-butynyl, 1-methyl-2-propynyl, 2-hexadecynyl, and equivalents thereof.

The "aryl" includes a monocyclic or polycyclic group consisting of 5- or 6-membered aromatic ring, which contains 0 to 3 heteroatoms selected from a nitrogen atom, an oxygen atom and a sulfur atom, and when it is a polycyclic group, then it has at least one aromatic ring. Examples of the aryl group are phenyl, naphthyl, fluorenyl, antholyl, biphenylyl, tetrahydronaphthyl, indanyl, phenantholyl, furyl, thienyl, pyrrolyl, imidazolyl, pyrazolyl, oxazolyl, thiazolyl, isoxazolyl, isothiazolyl, pyridyl, pyrazinyl, pyrimidinyl, pyridazinyl, indolyl, quinolyl, benzo[b]-thienyl, benzimidazolyl, 1H-imidazo[4,5-b]pyridyl, tetrahydroquinolyl, and equivalents thereof, and these aryl groups may have 1 to 5 substituents as mentioned above. Examples of the substituted aryl group are 2-, 3- or 4-methylphenyl, 2,4,6-trimethylphenyl, pentafluorophenyl, 2-, 3- or 4-fluorophenyl, 2-, 3- or 4-chlorophenyl, 2-bromo-4,6-difluorophenyl, 2,3,4-trifluorophenyl, 4-bromo-2-fluorophenyl, 3-chloro-4-fluorophenyl, 2-chloro-4-nitrophenyl, 2,4-dichlorophenyl, 3,5-dichlorophenyl, 2,4-difluorophenyl, 2,6-difluorophenyl, 3,4-difluorophenyl, 2-chloro-4-trifluoromethylphenyl, 2-fluoro-5-trifluoromethylphenyl, 2-fluoro-6-trifluoromethylphenyl, 3-fluoro-5-trifluoromethylphenyl, 4-fluoro-2-trifluoromethylphenyl, 2-fluoro-5-nitrophenyl, 2-, 3- or 4-trifluoromethylphenyl, 2-, 3- or 4-methoxyphenyl, 2-, 3- or 4-trifluoromethoxyphenyl, 4-cyanophenyl, 2-difluoromethoxyphenyl, 3-fluoro-4-methylphenyl, 5-fluoro-2-methylphenyl and equivalents thereof.

The "aralkyl" is ones having an aryl group as defined above at any position of an alkyl group having 1 to 6 carbon atoms or an alkenyl or alkynyl chain having 2 to 6 carbon atoms, and further the alkyl moiety thereof may optionally have 1 to 5 substituents as mentioned above. Examples of the aralkyl group are benzyl, fluorobenzyl, chlorobenzyl, phenylethyl, phenylpropyl, fluorophenylethyl, chlorophenylethyl, cinnamyl, fluorocinnamyl, thienylmethyl, thienylethyl, thienylpropyl, pyridylmethyl, pyridylethyl, pyridylpropyl and equivalents thereof.

Examples of the alkyl, cycloalkyl, alkenyl or alkynyl moiety having the defined number of carbon atoms, or the complex group containing an aryl or aralkyl moiety are ones wherein the above examples for each group are applied to the corresponding moieties. For example, the $C_{1-6}$ alkyloxy group is methoxy, ethoxy, propoxy, isopropoxy, butoxy, isobutoxy, tert-butoxy, pentyloxy, isopentyloxy, hexyloxy.

With respect to the group: U of the formula (I), when two $R^a$ groups attach to the same carbon atom and together with said carbon atom to form a spiro ring, said spiro ring is a 3- to 7-membered one having 0 to 2 heteroatoms selected from an oxygen atom, a nitrogen atom and a sulfur atom.

Examples of the substituent of the mono-substituted amino group for $R^6$ is ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, neopentyloxycarbonyl, hexyloxycarbonyl, 5-methylhexyloxycarbonyl, octyloxycarbonyl, decyloxycarbonyl, 3,3-dimethyloctyloxycarbonyl, $(CF_3)_2CFCF_2(CH_2)_2OCO$, $CF_3(CF_2)_3CH_2CH_2OCO$, $CF_3(CF_2)_2(CH_2)_3OCO$, $CF_3CF_2(CH_2)_6OCO$, $CF_3(CF_2)_8CH_2OCO$, cyclopentyloxycarbonyl, 2-cyclopentylethoxycarbonyl, cyclopentylmethoxycarbonyl, 3-cyclohexylpropoxycarbonyl, 3,7-dimethyl-6-octenyloxycarbonyl, benzyloxycarbonyl, phenethyloxycarbonyl, 3-phenylpropoxycarbonyl, 5-phenylpentyloxycarbonyl, 6-phenylhexyloxycarbonyl, 2-naphthylmethoxycarbonyl, 4-biphenylylmethoxycarbonyl, 4-butylbenzyloxycarbonyl, 4-butoxybenzyloxycarbonyl, 4-fluorobenzyloxycarbonyl, 4-methoxybenzyloxycarbonyl, 3,5-difluorobenzyloxycarbonyl, ethylaminocarbonyl, propylaminocarbonyl, isopropylaminocarbonyl, butylaminocarbonyl, tert-butylaminocarbonyl, hexylaminocarbonyl, cyclopentylaminocarbonyl, cyclohexylaminocarbonyl, allylaminocarbonyl, phenylaminocarbonyl, 3,5-difluorophenylaminocarbonyl, 4-trifluoromethylphenylaminocarbonyl, 3-methylphenylaminocarbonyl, 4-methoxyphenylaminocarbonyl, benzylaminocarbonyl, 4-fluorobenzylaminocarbonyl, phenethylaminocarbonyl, 4-methoxybenzylaminocarbonyl, 2-pyridylcarbonyl, 3-pyridylcarbonyl, 4-pyridylcarbonyl, 2-pyridylmethylcarbonyl, 3-pyridylmethylcarbonyl, 4-pyridylmethylcarbonyl, phenylsulfonyl, 3-chlorophenylsulfonyl, 2,6-dichlorophenylsulfonyl, 2-chloro-6-methylphenylsulfonyl, 4-methylphenylsulfonyl, 2-methylphenylsulfonyl, 2,4,6-trimethylphenylsulfonyl, 4-tert-butylphenylsulfonyl, 2-methyl-5-nitrophenylsulfonyl, 4-methoxyphenylsulfonyl, 4-tert-butoxyphenylsulfonyl, 4-acetylaminophenylsulfonyl, 3-trifluoromethylphenylsulfonyl, 2,6-dimethyl-4-biphenylylsulfonyl, 2-naphthylsulfonyl, 1-naphthylsulfonyl, cinnamylsulfonyl, butylsulfonyl, isobutylsulfonyl, 8-quinolyl-sulfonyl, 2-thienylsulfonyl, 3,5-dimethyl-4-isoxazolyl, 5-chloro-3-methyl-4-pyrazolyl, phenylaminosulfonyl, (7,7-dimethyl-2-oxobicyclo-[2.2.1]heptan-1-yl)methylsulfonyl and equivalents thereof.

Suitable examples of U of the formula (I) are groups as described below, and equivalents thereof.

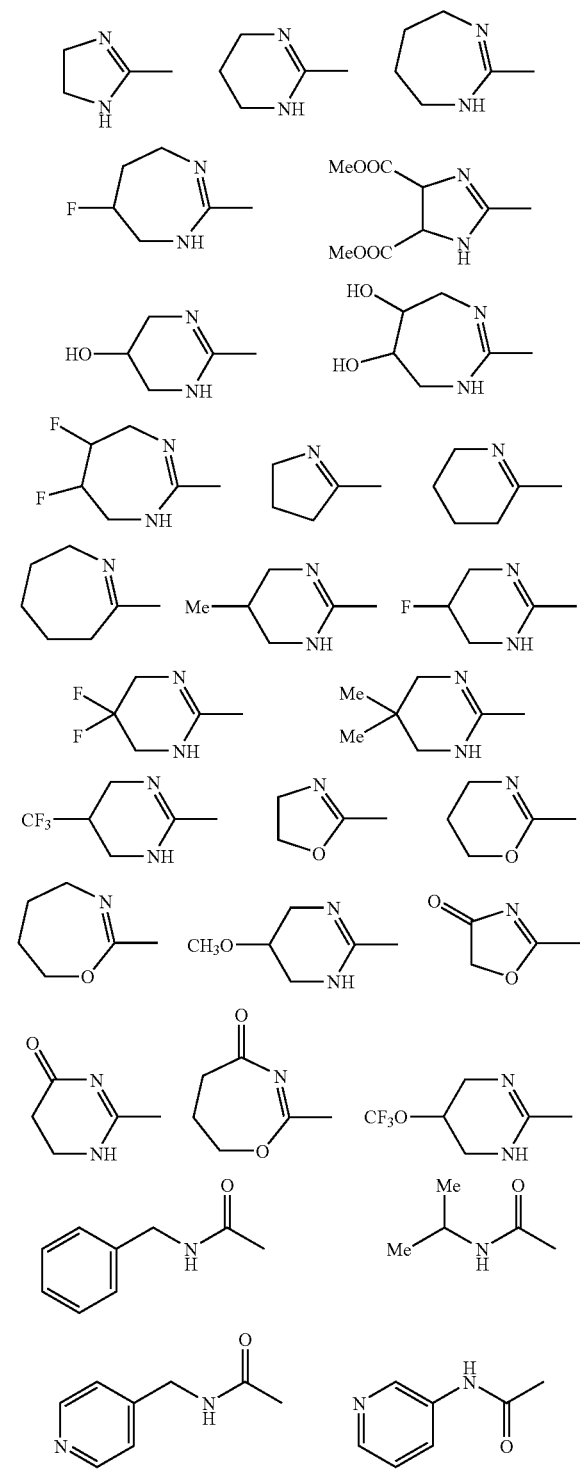

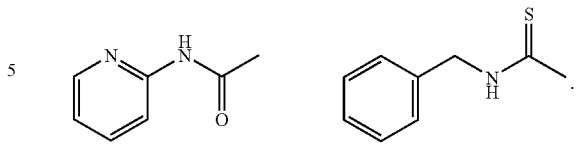

With respect to the group B of the formula (I), suitable examples of —$(CR^8R^9)_t$— formed by combining two $R^c$ are shown below together with 5 the carbon atoms to which they bond and a surrounding substructure thereof. Equivalents of these groups are also preferable.

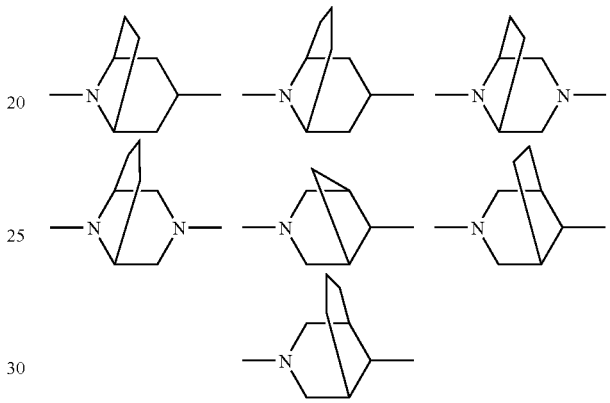

In the formula (I), the suitable examples of the substituent of the mono-substituted amino group for $R^6$ are a $C_{7-15}$ polycyclo-$C_{0-3}$ alkylcarbony group or a $C_{7-15}$ polycyclo-$C_{0-3}$ alkylsulfonyl group, such as the formulae as shown below. Equivalents thereof are also preferable.

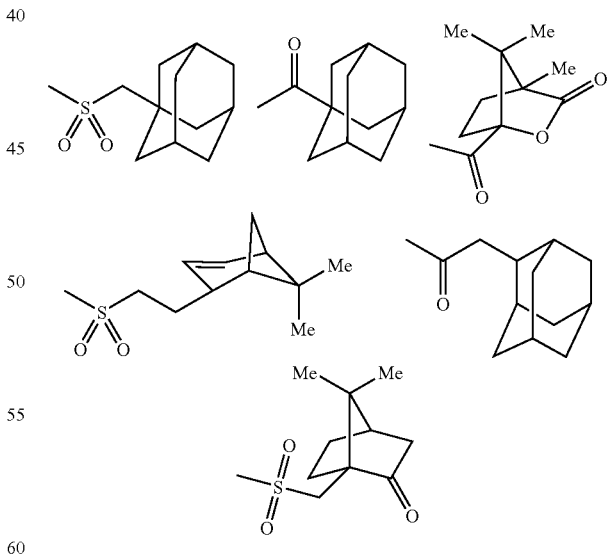

Preferable examples of the esterified carboxyl group of prodrugs of the compound of the formula (I) are methyloxycarbonyl group, ethyloxycarbonyl group, propyloxycarbonyl group, isopropyloxycarbonyl group, butyloxycarbonyl group, isobutyloxycarbonyl group, tert-butyloxycarbonyl group, cyclopropyloxycarbonyl group, cyclobutyloxycarbonyl group, cyclopentyloxycarbonyl group, cyclohexyloxycarbonyl group, cycloheptyloxycarbonyl group, benzyloxycarbonyl group, pyridyloxycarbonyl group, carboxymethyloxycarbonyl group, methoxycarbonylmethyloxycarbonyl group, methylaminocarbonylmethyloxycarbonyl group, dimethylaminocarbonylmethyloxycarbonyl group, 2-methylaminoethyloxycarbonyl group, 2-dimethylaminocarbonylethyloxycarbonyl group, (5-methyl-2-oxo-1,3-dioxolen-4-yl)methyloxycarbonyl group, acetoxymethyloxycarbonyl group, propionyloxymethyloxycarbonyl group, isobutyryloxymethyloxycarbonyl group, pivaloyloxymethyloxycarbonyl group, cyclopentylcarbonyloxymethyloxycarbonyl group, cyclohexylcarbonyloxymethyloxycarbonyl group, benzoyloxymethyloxycarbonyl group, 1-acetoxyethyloxycarbonyl group, 1-ethoxycarbonyloxyethyloxycarbonyl group, 1-tert-butoxycarbonyloxyethyloxycarbonyl group, 1-cyclopentyloxycarbonyloxyethyloxycarbonyl group and 1-cyclohexyloxycarbonyloxyethyloxycarbonyl group.

The preferable compounds of the present invention are the aryl-substituted alicyclic compound of the formula (I), a prodrug thereof, a pharmaceutically acceptable salt thereof, or an N-oxide derivative thereof, a hydrate or a solvate thereof, wherein U is a group selected from the following group:

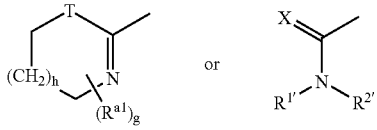

($T^1$ is —$CH_2$—, an oxygen atom or —$NR^{d1}$—, $R^{a1}$ is the same or different, and each is a hydrogen atom, a halogen atom, a hydroxy group, a $C_{1-6}$ alkyl group, a $C_{3-7}$ cycloalkyl group, an aryl group, an aralkyl group, a $C_{1-6}$ alkyloxy group, a $C_{1-6}$ alkyloxycarbonyl group, a carboxyl group, a $C_{1-6}$ alkylcarbonyloxy group, an amino group, a di($C_{1-3}$ alkyl)amino group, a $C_{1-3}$ alkylcarbonylamino group, a nitro group, a cyano group, a trifluoromethyl group, a trifluoromethoxy group or a trifluoroethoxy group, or when two $R^{a1}$ groups attach to the same carbon atom, then they combine to form an oxo group or a thioxo group, or together with said carbon atom to form a spiro ring, $R^{d1}$ is a hydrogen atom, a $C_{1-3}$ alkyl group, a $C_{1-3}$ alkylcarbonyl group or a $C_{1-6}$ alkyloxycarbonyl group, $R^{1'}$ and $R^{2'}$ are the same or different, and each is a hydrogen atom, a $C_{1-5}$ alkyl group, a $C_{3-7}$ cycloalkyl group, an aryl group or an aralkyl group, or $R^{1'}$ and $R^{2'}$ may combine to form —$(CH_2)_u$— or —$(CH_2)_v Y^1 (CH_2)_w$—, and $Y^1$ is an oxygen atom, a sulfur atom or —$NR^{12'}$—, $R^{12'}$ is a hydrogen atom, a methyl group, a $C_{1-4}$ alkyloxycarbonyl group or an acetyl group, X, g, h, u, v and w are as defined above), A is a group selected from the following group:

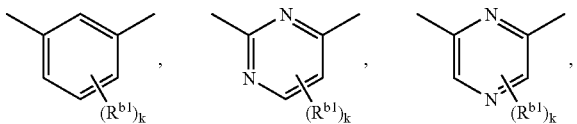

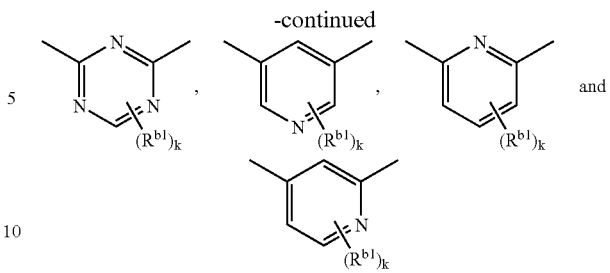

($R^{b1}$ is the same or different, and each is a hydrogen atom, a halogen atom, a hydroxy group, a $C_{1-3}$ alkyl group, an aryl group, a $C_{1-3}$ alkyloxy group, a $C_{1-3}$ alkyloxycarbonyl group, a carboxyl group, a $C_{1-3}$ alkylcarbonyloxy group, an amino group, a di($C_{1-3}$ alkyl)amino group, a $C_{1-3}$ alkylcarbonylamino group, a nitro group, a cyano group, a trifluoromethyl group or a trifluoromethoxy group, k is as defined above), B is a group selected from the following group:

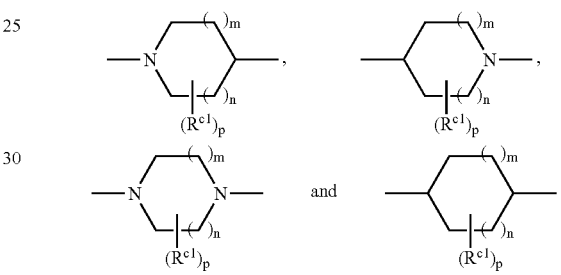

($R^{c1}$ is the same or different, and each is a hydrogen atom, a halogen atom, a hydroxy group, a $C_{1-6}$ alkyl group, a $C_{3-7}$ cycloalkyl group, an aryl group, an aralkyl group, a $C_{1-6}$ alkyloxy group, a $C_{1-6}$ alkyloxycarbonyl group, a formyl group, a carboxyl group, a $C_{1-6}$ alkylcarbonyloxy group, an amino group, a di($C_{1-3}$ alkyl)amino group, a $C_{1-3}$ alkylcarbonylamino group, a cyano group or a trifluoromethyl group, or two $R^{c1}$ groups may combine to form —$(CH_2)_t$—, m, n, p and t are as defined above), $R^3$ is a hydrogen atom,
$R^4$ is a hydrogen atom or a $C_{1-3}$ alkyl group,
Z, $R^5$, $R^6$ and $R^7$ are as defined above.

Among the above-mentioned preferable compounds, a compound wherein $R^6$ is a group other than a hydrogen atom is more preferable.

More preferable compound is the aryl-substituted alicyclic compound of the formula (I), a prodrug thereof, a pharmaceutically acceptable salt thereof, or an N-oxide derivative thereof, or a hydrate or a solvate thereof, wherein U is a group selected from the following group:

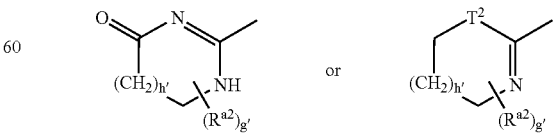

($T^2$ is —$CH_2$—, an oxygen atom or —$NR^{d2}$—, $R^{a2}$ is the same or different, and each is a hydrogen atom, a fluorine atom, a hydroxy group, a $C_{1-4}$ alkyl group, an aryl group, a $C_{1-3}$ alkyloxy group, a $C_{1-3}$ alkyloxycarbonyl group, a di($C_{1-3}$ alkyl)amino group, a $C_{1-3}$ alkylcarbonylamino group, a hydroxy-$C_{1-3}$ alkyl group, a carboxyl group, a $C_{1-3}$ alkylcarbonyloxy group, a trifluoromethyl group or a trifluoromethoxy group, $R^{d2}$ is a hydrogen atom, a methyl group, an acetyl group, a propionyl group, a methoxycarbonyl group, an ethoxycarbonyl group or a tert-butoxycarbonyl group, g' is 1 or 2, h' is an integer of 0 to 2), B is a group selected from the following group:

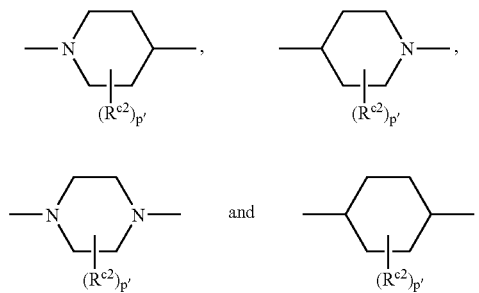

($R^{c2}$ is the same or different, and each is a hydrogen atom, a methyl group, a phenyl group, a $C_{1-2}$ alkyloxycarbonyl group or a carboxyl group, or two $R^{c2}$ groups may combine to form —$(CH_2)_t$—, p' is 1 or 2, t is an integer of 1 to 3), Z is —$CONR^{4'}$—, —$NR^{4'}CO$— or —$COCH_2$—, $R^{4'}$ is a hydrogen atom or a methyl group, $R^6$ is a mono-substituted amino group (the substituent thereof is a formyl, a $C_{1-10}$ alkylcarbonyl, a $C_{3-7}$ cycloalkylcarbonyl, a $C_{2-10}$ alkenylcarbonyl, a $C_{2-10}$ alkynylcarbonyl, an arylcarbonyl, an aralkylcarbonyl, a $C_{7-15}$ polycyclo-$C_{0-3}$ alkylcarbonyl, a $C_{1-16}$ alkyloxycarbonyl, a polyfluoro-$C_{1-6}$ alkyloxycarbonyl, a $C_{3-7}$ cycloalkyloxycarbonyl, a $C_{2-16}$ alkenyloxycarbonyl, a $C_{2-16}$ alkynyloxycarbonyl, an aryloxycarbonyl, a $C_{3-7}$ cycloalkyl-$C_{1-6}$ alkyloxycarbonyl, an aralkyloxycarbonyl, a $C_{1-10}$ alkylaminocarbonyl, a $C_{3-7}$ cycloalkylaminocarbonyl, a $C_{2-10}$ alkenylaminocarbonyl, a $C_{2-10}$ alkynylaminocarbonyl, an arylaminocarbonyl, an aralkylaminocarbonyl, a $C_{1-10}$ alkylsulfonyl, a $C_{3-7}$ cycloalkylsulfonyl, a $C_{2-10}$ alkenylsulfonyl, a $C_{2-10}$ alkynylsulfonyl, an arylsulfonyl, an aralkylsulfonyl, a $C_{7-15}$ polycyclo-$C_{0-3}$ alkylsulfonyl, a $C_{1-10}$ alkylaminosulfonyl, a $C_{3-7}$ cycloalkylaminosulfonyl, a $C_{2-10}$ alkenylaminosulfonyl, a $C_{2-6}$ alkynylaminosulfonyl, an arylaminosulfonyl or an aralkylaminosulfonyl), $R^7$ is a hydrogen atom, a $C_{1-6}$ alkyl group, a $C_{3-7}$ cycloalkyl group or an aralkyl group, A and $R^3$ are as defined above, $R^5$ is as defined above.

Further preferable compound is the aryl-substituted alicyclic compound of the following formula (Ia), a prodrug thereof, a pharmaceutically acceptable salt thereof, or an N-oxide derivative thereof, or a hydrate or a solvate thereof.

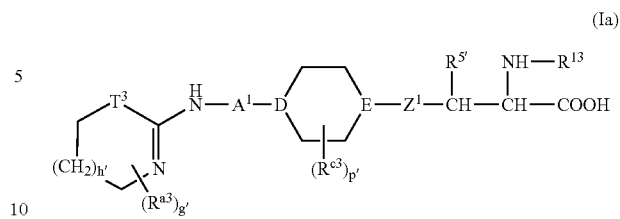

wherein $A^1$ is a group selected from the following group:

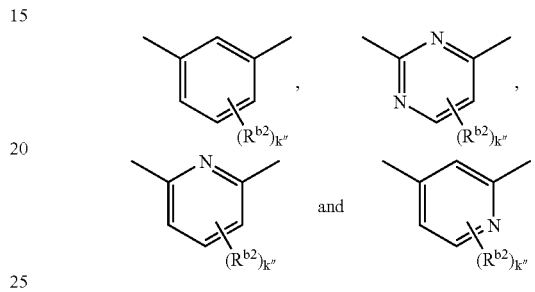

($R^{b2}$ is the same or different, and each is a hydrogen atom, a fluorine atom, a chlorine atom, a hydroxy group, a methyl group, a methoxy group, a phenyl group, a methoxycarbonyl group, a carboxyl group, an acetoxy group, an acetylamino group, a nitro group, a cyano group, a trifluoromethyl group or a trifluoromethoxy group, k" is 1 or 2), $Z^1$ is —CONH—, —NHCO— or —$COCH_2$—, $T^3$ is —$NR^{d2}$—, $R^{d2}$ is a hydrogen atom, an acetyl group, a propionyl group, a methoxycarbonyl group, an ethoxycarbonyl group or a tert-butoxycarbonyl group, D and E are the same or different, and each is —CH— or a nitrogen atom, when E is a nitrogen atom, then $Z^1$ is —CONH— or —$COCH_2$—, $R^{a3}$ is the same or different, and each is a hydrogen atom, a fluorine atom, a hydroxy group, a methyl group, a methoxy group, a trifluoromethyl group or a trifluoromethoxy group, g' is 1 or 2, h' is an integer of 0 to 2, $R^{c3}$ is the same or different, and each is a hydrogen atom or a methyl group, or two $R^{c3}$ groups may combine to form —$(CH_2)_t$—, p' is 1 or 2, t is an integer of 1 to 3, $R^{5'}$ is a hydrogen atom, $R^{13}$ is a $C_{1-10}$ alkyloxycarbonyl group, a polyfluoro-$C_{1-10}$ alkyloxycarbonyl group, a $C_{3-7}$ cycloalkyloxycarbonyl group, a $C_{2-10}$ alkenyloxycarbonyl group, a $C_{2-10}$ alkynyloxycarbonyl group, an aryloxycarbonyl group, a $C_{3-7}$ cycloalkyl-$C_{1-6}$ alkyloxycarbonyl group, an aralkyloxycarbonyl group, a $C_{1-10}$ alkylaminocarbonyl group, a $C_{3-7}$ cycloalkylaminocarbonyl group, a $C_{2-10}$ alkenylaminocarbonyl group, a $C_{2-10}$ alkynylaminocarbonyl group, an arylaminocarbonyl group, an aralkylaminocarbonyl group, an arylsulfonyl group, an aralkylsulfonyl group or a $C_{7-15}$ polycyclo-$C_{0-3}$ alkylsulfonyl group, provided that in the above definition, the alkyl group, the cycloalkyl group, the alkenyl group, the alkynyl group and the alkyl moiety of the aralkyl group may optionally be substituted by 1 to 3 atoms or groups selected from a halogen, a $C_{1-3}$ alkyloxy, an amino and a hydroxy, and the aryl group and the aryl moiety may optionally be substituted by 1 to 3 atoms or groups selected from a halogen, a methyl, an ethyl, a propyl, a butyl, a $C_{3-7}$ cycloalkyl, an aryl, an aralkyl, an amino, a formylamino, an acetylamino, a dimethylamino, a dimethylaminomethyl, an aryl carbonylamino, a $C_{1-4}$ alkyloxy, a carboxyl, a $C_{1-3}$ alkyloxycarbonyl, a hydroxy, a hydroxymethyl, a cyano, a nitro, a trifluoromethyl, an acetoxy and a trifluoromethoxy.

Especially preferable compound is the aryl-substituted alicyclic compound of the following formula (Ib), a prodrug thereof, a pharmaceutically acceptable salt thereof, or a hydrate or solvate thereof.

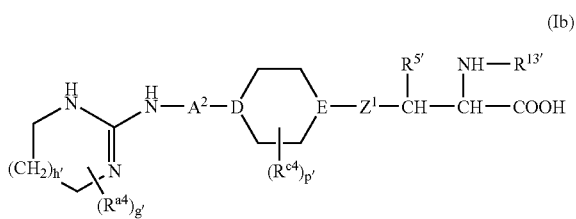

(Ib)

wherein $A^2$ is a group selected from the following group:

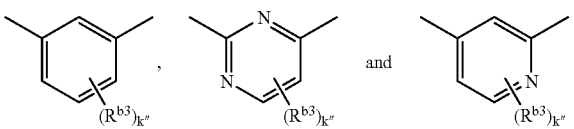

($R^{b3}$ is the same or different, and each is a hydrogen atom, a fluorine atom, a methyl group, a methoxy group, a trifluoromethyl group or a trifluoromethoxy group, k" is 1), $Z^1$ is —CONH—, —NHCO— or —COCH$_2$—, D and E are the same or different, and each is —CH— or a nitrogen atom, and when E is —CH—, then $Z^1$ is —CONH— or —NHCO—, and when E is a nitrogen atom, then $Z^1$ is —CONH— or —COCH$_2$—, $R^{a4}$ is the same or different, and each is a hydrogen atom, a fluorine atom, a hydroxy group or a methyl group, $R^{c4}$ is a hydrogen atom or a methyl group, $R^{5'}$ is a hydrogen atom, $R^{13'}$ is a $C_{1-10}$ alkyloxycarbonyl group, a polyfluoro-$C_{1-10}$ alkyloxycarbonyl group, a $C_{3-7}$ cycloalkyloxycarbonyl group, a $C_{2-10}$ alkenyloxycarbonyl group, a $C_{2-10}$ alkynyloxycarbonyl group, a $C_{3-7}$ cycloalkyl-$C_{1-6}$ alkyloxycarbonyl group, an aralkyloxycarbonyl group or an arylsulfonyl group, g' is 1 or 2, h' is an integer of 0 to 2, p' is 1 or 2, provided that in the above definition, the alkyl group, the cycloalkyl group, the alkenyl group, the alkynyl group, and the alkyl moiety of the aralkyl group may optionally be substituted by one atom or group selected from a halogen, a $C_{1-3}$ alkyloxy, an amino and a hydroxy, and the aryl group and the aryl moiety may optionally be substituted by 1 or 2 atoms or groups selected from a halogen, a methyl, an ethyl, a propyl, a butyl, a $C_{3-7}$ cycloalkyl, an aryl, an aralkyl, an amino, a formylamino, an acetylamino, a dimethylamino, a $C_{1-4}$ alkyloxy, a carboxyl, a hydroxy, a hydroxymethyl, a cyano, a nitro, a trifluoromethyl, an acetoxy and a trifluoromethoxy.

In the formula (Ib), the following combinations are preferable.

(i) Cases wherein D is a nitrogen atom, E is —CH—, $Z^1$ is —CONH— or —NHCO—, and $R^{c4}$ is a hydrogen atom:

(ii) Cases wherein both D and E are simultaneously —CH—, $Z^1$ is —CONH— or —NHCO—, and $R^{c4}$ is a hydrogen atom:

(iii) Cases wherein both D and E are simultaneously a nitrogen atom, $Z^1$ is —CONH— or —COCH$_2$—, and $R^{c4}$ is a hydrogen atom or a methyl group: and (iv) Cases wherein D is —CH—, E is a nitrogen atom, $Z^1$ is —CONH— or —COCH$_2$—, and $R^{c4}$ is a hydrogen atom:

Examples of especially preferable compound are, the compounds as described below, the compounds as listed in Table 1, and the compounds of Examples as listed in Table 2 which had been studied with respect to their integrin binding inhibitory activity, a prodrug thereof, or a pharmaceutically acceptable salt thereof, or a hydrate or a solvate thereof. Among the following compounds, ones to which an example number is appended following each chemical name, a prodrug thereof, or a pharmaceutically acceptable salt thereof, or a hydrate or a solvate thereof are most preferable.

(2S)-2-benzyloxycarbonylamino-3-[[1-[3-(1,4,5,6-tetrahydropyrimidin-2-yl)aminophenyl]piperidin-4-yl]carbonylamino]propanoic acid (Example 2), (2S)-2-benzyloxycarbonylamino-3-[[1-[2-(1,4,5,6-tetrahydropyrimidin-2-yl)amino-6-methylpyrimidin-4-yl]piperidin-4-yl]carbonylamino]propanoic acid (Example 150), (2S)-2-benzyloxycarbonylamino-5-[4-[3-(1,4,5,6-tetrahydropyrimidin-2-yl)aminophenyl]piperazin-1-yl]-5-oxopentanoic acid (Example 121), (2S)-2-benzyloxycarbonylamino-3-[[4-[3-(1,4,5,6-tetrahydropyrimidin-2-yl)aminophenyl]piperazin-1-yl]carbonylamino]propanoic acid (Example 145), (2S)-2-Isopropoxycarbonylamino-3-[[1-[3-(1,4,5,6-tetrahydropyrimidin-2-yl)aminophenyl]piperidin-4-yl]carbonylamino]propanoic acid (Example 44), (2S)-2-benzyloxycarbonylamino-3-[[1-[3-(1H-4,5,6,7-tetrahydro-1,3-diazepin-2-yl)aminophenyl]piperidin-4-yl]carbonylamino]propanoic acid (Example 10), (2S)-2-benzyloxycarbonylamino-5-[4-[2-methoxy-5-(1,4,5,6-tetrahydropyrimidin-2-yl)aminophenyl]piperazin-1-yl]-5-oxopentanoic acid (Example 154), (2S)-2-benzyloxycarbonylamino-3-[[1-[2-methoxy-5-(1,4,5,6-tetrahydropyrimidin-2-yl) aminophenyl]piperidin-4-yl]carbonylamino]-propanoic acid (Example 152), (2S)-2-isobutoxycarbonylamino-3-[[1-[3-(1,4,5,6-tetrahydropyrimidin-2-yl)aminophenyl]piperidin-4-yl]carbonylamino]propanoic acid (Example 92), (2S)-2-hexyloxycarbonylamino-3-[[1-[3-(1,4,5,6-tetrahydropyrimidin-2-yl)aminophenyl]piperidin-4-yl]carbonylamino]propanoic acid (Example 88), (2S)-2-benzyloxycarbonylamino-3-[[1-[4-(1,4,5,6-tetrahydropyrimidin-2-yl)aminopyridin-2-yl]piperidin-4-yl]carbonylamino]-propanoic acid (Example 159), (2S)-2-benzyloxycarbonylamino-3-[[1-[3-(5-hydroxy-1,4,5,6-tetrahydropyrimidin-2-yl)aminophenyl]piperidin-4-yl]carbonylamino]-propanoic acid (Example 14), (2S)-2-benzyloxycarbonylamino-3-[[1-[3-(5,5-dimethyl-1,4,5,6-tetrahydropyrimidin-2-yl) aminophenyl]piperidin-4-yl]carbonylamino]-propanoic acid (Example 11), (2S)-2-benzyloxycarbonylamino-3-[[1-[3-(5-fluoro-1,4,5,6-tetrahydropyrimidin-2-yl) aminophenyl]piperidin-4-yl]carbonylamino]-propanoic acid (Example 13), (2S)-2-benzyloxycarbonylamino-3-[[1-[4-methyl-3-(1,4,5,6-tetrahydropyrimidin-2-yl)aminophenyl]piperidin-4-yl]carbonylamino]-propanoic acid (Example 153), (2S)-2-hexylaminocarbonylamino-3-[[1-[3-(1,4,5,6-tetrahydropyrimidin-2-yl)aminophenyl]piperidin-4-yl]carbonylamino]propanoic acid (Example 117), (2S)-2-(2-methoxyethoxycarbonylamino)-3-[[1-[3-(1,4,5,6-tetrahydropyrimidin-2-yl)aminophenyl]piperidin-4-yl]carbonylamino]-propanoic acid (Example 94), (2S)-2-butoxycarbonylamino-3-[[1-[3-(1,4,5,6-tetrahydropyrimidin-2-yl) aminophenyl]piperidin-4-yl]carbonylamino]propanoic acid (Example 87), (2S)-2-octyloxycarbonylamino-3-[[1-[3-(1,4,5,6-tetrahydropyrimidin-2-yl)aminophenyl]piperidin-4-yl]carbonylamino]propanoic acid (Example 89), (2S)-2-neopentyloxycarbonylamino-3-[[1-[3-(1,4,5,6-tetrahydropyrimidin-2-yl)aminophenyl]piperidin-4-yl]carbonylamino]propanoic acid (Example 93), (2S)-2-benzyloxycarbonylamino-3-[[4-[3-(1,4,5,6-tetrahydropyrimidin-2-yl)aminophenyl]cyclohexyl]carbonylamino]propanoic acid (Stereoisomer A of Example 151), (2S)-2-benzyloxycarbonylamino-3-[[1-[5-fluoro-3-(1,4,5,6-tetrahydropyrimidin-2-yl)aminophenyl]piperidin-4-yl]carbonylamino]-propanoic acid (Example 156), (2S)-2-hexyloxycarbonylamino-5-[4-[3-(1,4,5,6-tetrahydropyrimidin-2-yl)aminophenyl]piperazin-1-yl]-5-oxopentanoic acid (Example 137), (2S)-2-benzyloxycarbonylamino-3-[[1-[3-(2-imidazolin-2-yl)aminophenyl]piperidin-4-yl]carbonylamino]propanoic acid (Example 9), (2S)-2-benzyloxycarbonylamino-3-[[1-[4-(5-fluoro-1,4,5,6-tetrahydropyrimidin-2-yl)aminopyridin-2-yl]piperidin-4-yl]carbonylamino]-propanoic acid (Example 160), (2S)-2-benzyloxycarbonylamino-3-[[1-[3-(5,5-difluoro-1,4,5,6-tetrahydropyrimidin-2-yl)aminophenyl]piperidin-4-yl]carbonylamino]-propanoic acid (Example 12), (2S)-2-isobutoxycarbonylamino-5-[4-[3-(1,4,5,6-tetrahydropyrimidin-2-yl)aminophenyl]piperazin-1-yl]-5-oxopentanoic acid (Example 138), (2S)-2-isobutoxycarbonylamino-3-[[1-[3-(5,5-dimethyl-1,4,5,6-tetrahydropyrimidin-2-yl)aminophenyl]piperidin-4-yl]carbonylamino]-propanoic acid (Example 18), (2S)-2-isobutoxycarbonylamino-3-[[1-[3-(5-fluoro-1,4,5,6-tetrahydropyrimidin-2-yl)aminophenyl]piperidin-4-yl]carbonylamino]-propanoic acid (Example 19), (2S)-2-Isobutoxycarbonylamino-3-[[1-[3-(5-hydroxy-1,4,5,6-tetrahydropyrimidin-2-yl)aminophenyl]piperidin-4-yl]carbonylamino]-propanoic acid (Example 20), (2S)-2-ethoxycarbonylamino-3-[[1-[3-(1,4,5,6-tetrahydropyrimidin-2-yl)aminophenyl]piperidin-4-yl]carbonylamino]propanoic acid (Example 86), (2S)-2-decyloxycarbonylamino-3-[[1-[3-(1,4,5,6-tetrahydropyrimidin-2-yl)aminophenyl]piperidin-4-yl]carbonylamino]propanoic acid (Example 90), (2S)-2-allyloxycarbonylamino-3-[[1-[3-(1,4,5,6-tetrahydropyrimidin-2-yl)aminophenyl]piperidin-4-yl]carbonylamino] propanoic acid (Example 96), (2S)-2-benzyloxycarbonylamino-5-[4-[3-(5-fluoro-1,4,5,6-tetrahydropyrimidin-2-yl)aminophenyl]piperazin-1-yl]-5-oxopentanoic acid (Example 124), (2S)-2-Isobutoxycarbonylamino-5-[4-[3-(5-fluoro-1,4,5,6-tetrahydropyrimidin-2-yl)aminophenyl]piperazin-1-yl]-5-oxopentanoic acid (Example 127), (2S)-2-hexyloxycarbonylamino-5-[4-[3-(5-fluoro-1,4,5,6-tetrahydropyrimidin-2-yl)aminophenyl]piperazin-1-yl]-5-oxopentanoic acid (Example 130), (2S)-2-benzyloxycarbonylamino-5-[4-[2-fluoro-5-(1,4,5,6-tetrahydropyrimidin-2-yl)aminophenyl]piperazin-1-yl]-5-oxopentanoic acid (Example 155), (2S)-2-isopropoxycarbonylamino-3-[[4-[3-(2-oxazolin-2-yl)aminophenyl]piperazine-1-yl]carbonylamino]propanoic acid, (2S)-2-isobutoxycarbonylamino-3-[[4-[3-(7H-3,4,5,6-tetrahydroazepin-2-yl)aminophenyl]piperazin-1-yl]carbonylamino]propanoic acid, (2S)-3-[[1-[2-(benzylaminocarbonyl)amino-6-methylpyrimidin-4-yl]piperidin-4-yl]carbonylamino]-2-(benzyloxycarbonylamino)propanoic acid, (2S)-2-benzyloxycarbonylamino-3-[N-[8-[3-(1,4,5,6-tetrahydropyrimidin-2-yl)aminophenyl]-8-azabicyclo[3.2.1]octan-3-yl]carbamoyl]-propanoic acid, (2S)-2-ethoxycarbonylamino-3-[[8-[3-(5,5-difluoro-1,4,5,6-tetrahydropyrimidin-2-yl)aminophenyl]-8-azabicyclo[3.2.1]octan-3-yl]-carbonylamino]propanoic acid, (2S)-3-[[1-[5-fluoro-3-(1H-4,5,6,7-tetrahydro-1,3-diazepin-2-yl)aminophenyl]piperidin-4-yl]carbonylamino]-2-(isobutoxycarbonylamino)propanoic acid, (2S)-2-isopropoxycarbonylamino-5-[4-[5-(1H-4,5,6,7-tetrahydro-1,3-diazepin-2-yl)amino-2-methoxyphenyl]piperazin-1-yl]-5-oxopentanoic acid, (2S)-5-[4-[2-fluoro-5-(1H-4,5,6,7-tetrahydro-1,3-diazepin-2-yl)amino]piperazin-1-yl]-2-(isobutoxycarbonylamino)-5-oxopentanoic acid, (2S)-2-butoxycarbonylamino-5-[4-[4-(1H-4,5,6,7-tetrahydro-1,3-diazepin-2-yl) aminopyridin-2-yl]piperazin-1-yl]-5-oxopentanoic acid, (2S)-2-benzyloxycarbonylamino-3-[[1-[4-(1H-4,5,6,7-tetrahydro-1,3-diazepin-2-yl)aminopyridin-2-yl]piperidin-4-yl]carbonylamino]-propanoic acid, (2S)-2-hexyloxycarbonylamino-3-[[1-[4-(2-imidazolin-2-yl)aminopyridin-2-yl]piperidin-4-yl]carbonylamino]propanoic acid, (2S)-2-isopropoxycarbonylamino-3-[[4-[4-(2-imidazolin-2-yl)aminopyridin-2-yl]piperazin-1-yl]carbonylamino]propanoic acid, (2S)-2-benzyloxycarbonylamino-3-[[2,6-dimethyl-4-[3-(1,4,5,6-tetrahydropyrimidin-2-yl)aminophenyl]piperazin-1-yl]carbonylamino]-propanoic acid, (2S)-2-hexyloxycarbonylamino-3-[[2,5-dimethyl-4-[3-(5-fluoro-1,4,5,6-tetrahydropyrimidin-2-yl)aminophenyl]piperazin-1-yl]carbonylamino]propanoic acid, (2S)-2-Isobutoxycarbonylamino-5-[2,6-dimethyl-4-[3-(5,5-dimethyl-1,4,5,6-tetrahydropyrimidin-2-yl)aminophenyl]piperazin-1-yl]-5-oxopentanoic acid, (2S)-2-benzyloxycarbonylamino-5-[3,5-dimethyl-4-[3-(5,5-difluoro-1,4,5,6-tetrahydropyrimidin-2-yl)aminophenyl]piperazin-1-yl]-5-oxopentanoic acid, (2S)-2-hexyloxycarbonylamino-3-[[3,5-dimethyl-4-[3-(5-hydroxy-1,4,5,6-tetrahydropyrimidin-2-yl)aminophenyl]piperazin-1-yl]carbonylamino]propanoic acid, (2S)-2-isobutoxycarbonylamino-3-[[2,2-dimethyl-4-[3-(5-hydroxy-1,4,5,6-tetrahydropyrimidin-2-yl)aminophenyl]piperazin-1-yl]carbonylamino]propanoic acid, (2S)-2-benzyloxycarbonylamino-5-[2-methyl-4-[3-(5-fluoro-1,4,5,6-tetrahydropyrimidin-2-yl)aminophenyl]piperazin-1-yl]-5-oxopentanoic acid, and (2S)-2-isopropoxycarbonylamino-5-[3-methyl-4-[3-(5-fluoro-1,4,5,6-tetrahydropyrimidin-2-yl)aminophenyl]piperazin-1-yl]-5-oxopentanoic acid.

TABLE 1

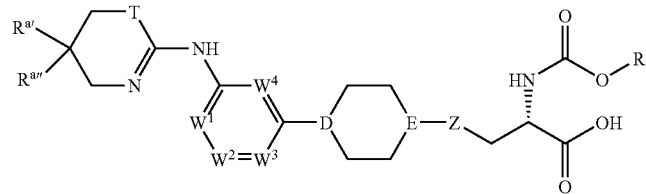

| R8' | R8" | T | W1 | W2 | W3 | W4 | D | E | Z | R |
|---|---|---|---|---|---|---|---|---|---|---|
| F | H | NH | CH | CH | C—CF3 | CH | N | CH | CONH | CH2CHMe2 |
| F | F | NH | CH | CH | C—CF3 | CH | N | CH | CONH | (CH2)5Me |
| OMe | H | NH | CH | CH | N | CH | N | N | COCH2 | CH2Ph |
| F | H | NH | CH | CH | N | CH | N | N | COCH2 | (CH2)5Me |
| F | H | NH | CH | CH | N | CH | N | N | COCH2 | (CH2)2CHMe(CH2)3CHMe2 |
| F | H | NH | CH | CH | N | CH | N | CH | CONH | (CH2)2(CF2)3CF3 |
| F | F | NH | CH | CH | N | CH | N | CH | CONH | (CH2)7Me |
| F | H | NH | CH | CH | C—CF3 | CH | N | N | COCH2 | CH2CHMe2 |
| OH | H | NH | CH | CH | C—CF3 | CH | N | N | CONH | (CH2)3Me |
| F | F | NH | CH | C—F | C—F | CH | N | N | CONH | CH2Ph |
| OH | H | NH | CH | C—F | CH | CH | N | CH | CONH | CH2CHMe2 |
| H | H | CH2 | CH | C—F | C—F | CH | N | CH | CONH | CH2Ph |
| F | H | NH | CH | CH | C—OMe | CH | N | N | CONH | CHMe2 |
| Me | Me | NH | CH | CH | C—OMe | CH | N | N | COCH2 | CH2CH2Me |
| H | H | O | CH | CH | C—OMe | CH | N | N | COCH2 | CHMe2 |
| F | F | NH | CH | CH | CH | CH | CH | N | CONH | CHMeCH2Me |
| F | H | NH | CH | CH | CH | CH | CH | CH | CONH | CH2-cyclo-C5H9 |
| CF3 | CF3 | NH | CH | CH | CH | N | N | CH | CONH | CHMeCH2Me |
| OH | H | NH | CH | N | CH | CH | N | CH | CONH | CH2CHMe2 |
| F | H | NH | CH | N | CH | CH | N | N | CONH | CH2Ph |
| F | H | CH2 | CH | C—Me | N | N | N | N | COCH2 | (CH2)7Me |
| OH | H | NH | CH | N | CH | N | N | N | CONH | (CH2)5Me |
| F | H | NH | CH | N | CH | N | N | N | COCH2 | CHMe2 |
| CF3 | CF3 | CH2 | CH | N | CH | N | N | N | COCH2 | CH2Me |
| H | H | O | CH | N | CH | N | N | N | COCH2 | (CH2)5Me |
| F | H | CH2 | CH | CH | CH | CH | N | CH | CONH | CH2Ph |
| H | H | O | CH | CH | CH | CH | N | CH | CONH | CH2CHMe2 |
| H | H | CH2 | CH | C—Me | N | N | N | CH | CONH | CH2CMe3 |
| H | H | O | CH | N | CH | CH | N | N | COCH2 | CMe3 |
| OH | H | NH | CH | CH | CH | N | N | N | COCH2 | CHMe2 |
| F | H | NH | CH | C—Me | N | N | N | CH | CONH | (CH2)2(CF2)3CF3 |
| OCF3 | H | NH | N | C—Me | CH | N | N | N | COCH2 | CH2CH=CHCH3 |
| H | H | NH | CH | CH | CH | CH | CH | N | COCH2NH | (CH2)3Me |
| H | H | O | N | C—Me | CH | N | N | CH | CONH | (CH2)5Me |
| H | H | CH2 | N | C—Me | CH | N | N | N | COCH2 | CHMeCH2Me |
| F | H | NH | N | CH | CH | CH | N | N | COCH2 | CHMe2 |
| F | H | NH | N | CH | CH | CH | N | CH | CONH | (CH2)5Me |
| H | H | O | N | CH | CH | CH | N | N | COCH2 | CHMeCH2Me |
| F | F | NH | N | CH | CH | CH | N | N | CONH | CMe3 |
| F | H | NH | CH | N | CH | CH | N | N | COCH2 | CH2Ph |
| F | H | NH | CH | N | CH | CH | N | CH | CONH | CH2CHMe2 |
| F | H | NH | CH | CH | CH | CH | N | N | COCH2 | CH2CH2(CF2)2CF(CF3)2 |
| H | H | NH | CH | CH | N | CH | N | CH | COCH2 | CH2Ph |
| F | H | NH | CH | CH | CH | N | N | N | COCH2 | (CH2)3Me |
| F | H | NH | CH | CH | CH | CH | CH | CH | COCH2 | CH2CHMe2 |

The process for preparing the compound of the formula (I) will be explained below. The compound of the formula (I) can be prepared according to the process for preparing the compound of the following formula (I'). The compound (I') may be prepared by reacting the compound of the formula (II) and the compound of the formula (III) as shown in the following Reaction Scheme. In addition, the compound of the formula (I') may also be prepared by reacting the compound of the formula (II) wherein the group: U—NR3— is protected with a suitable protecting group, with the compound of the formula (III), followed by removing said protecting group from the product. When the compound of the formula (I') wherein R7 is a hydrogen atom is prepared, said compound is subjected to hydrolysis or acid decomposition, if necessary, to give the compound of the formula (I'). Besides, when the compound of the formula (II) and/or the compound of the formula (III) have an asymmetric carbon atom, the configuration with respect to the asymmetric carbon atom of said compounds is retained in the compound of the formula (I') thus obtained.

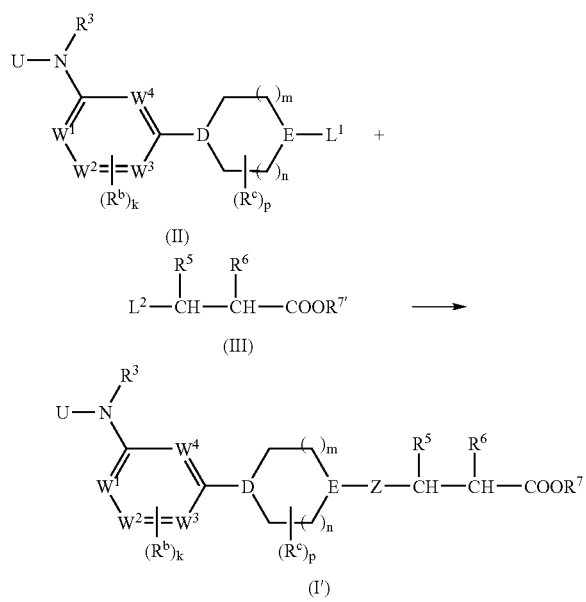

(when E is —CH—, then $L^1$ and $L^2$ are a different amino or carboxyl group, when E is a nitrogen atom, then $L^1$ is a hydrogen atom and $L^2$ is a lower alkyloxycarbonylamino group, an aryloxycarbonylamino group or a carboxymethyl group, or $L^1$ is a lower alkyloxycarbonyl group or an aryloxycarbonyl group, and $L^2$ is an amino group, $R^{7'}$ is the same groups as $R^7$ as mentioned above excluding a hydrogen atom, and U, $W^1$, $W^2$, $W^3$, $W^4$, D, E, $R^b$, $R^c$, $R^3$, $R^5$, $R^6$, k, p, m and n are as defined above).

The reaction of the compound of the formula (II) and the compound of the formula (III) is carried out under conventional reaction conditions for amido bond forming reaction. The compound of the formula (II) wherein $L^1$ is a carboxyl group, or the compound of the formula (III) wherein $L^2$ is a carboxyl group or a carboxymethyl group may be reacted with the compound of the formula (III) or the compound of the formula (II), respectively, after these compounds are converted into a reactive derivative at the carboxyl group thereof.

The reactive derivative of the compound of the formula (II) wherein $L^1$ is a carboxyl group, or the compound of the formula (III) wherein $L^2$ is a carboxyl group or a carboxymethyl group is, for example, a lower alkyl ester (especially, methyl ester), an active ester, an acid anhydride, an acid halide (especially an acid chloride). The active ester is, for example, p-nitrophenyl ester, N-hydroxysuccinimide ester, pentafluorophenyl ester. The acid anhydride is, for example, a symmetric acid anhydride or a mixed acid anhydride with ethyl chlorocarbonate, isobutyl chlorocarbonate, isovaleric acid, pivalic acid, etc.

When the compound of the formula (II) wherein $L^1$ is a carboxyl group, or the compound of the formula (III) wherein $L^2$ is a carboxyl group or a carboxymethyl group is used, the present reaction is usually carried out in the presence of a condensing agent. The condensing agent is, for example, N,N'-dicyclohexylcarbodiimide, 1-ethyl-3-(3-dimethylaminopropyl)carbodiimide hydrochloride, N,N'-carbonyldiimidazole, benzotriazol-1-yloxytris(pyrrolidino)phosphonium hexafluorophosphate. These condensing agents are used alone, or a combination of these condensing agents and a peptide synthesis reagent such as N-hydroxysuccinimide, 1-hydroxybenzotriazole, etc.

The reaction of the compound of the formula (II) or a reactive derivative thereof with the compound of the formula (III), or the reaction of the compound of the formula (II) with the compound of the formula (III) or a reactive derivative thereof is carried out in a solvent or without a solvent. The solvent used should be selected according to the kinds of the starting compound, etc., and includes, for example, toluene, tetrahydrofuran, dioxane, ethylene glycol diethyl ether, dichloromethane, chloroform, ethyl acetate, acetone, acetonitrile, dimethylformamide. These solvents may be used alone or in the form of a mixture of two or more solvents. The compound of the formula (II) wherein E is a nitrogen atom, and $L^1$ is a hydrogen atom, or the compound of the formula (III) wherein $L^2$ is an amino group may be used in the form of an acid addition salt such as hydrochloride, etc., to produce a free basic compound in the reaction system.

This reaction is usually carried out in the presence of a base. The base includes, for example, an inorganic base such as potassium carbonate, sodium hydrogen carbonate, or an organic base such as triethylamine, ethyldiisopropylamine, N-methylmorpholine, pyridine, 4-dimethylaminopyridine, etc. The reaction temperature may vary according to the kinds of the starting compounds used, and it is usually in the range of about –30° C. to about 150° C., preferably in the range of about –10° C. to about 50° C. When the compound (II) or the compound (III) has a functional group participating in the reaction within the structure thereof, it is preferable to protect such functional groups by a conventional method, and to remove them after the reaction.

When the product wherein $R^{7'}$ is a $C_{1-6}$ alkyl group is obtained by the reaction of the compound (II) with the compound (III), such compounds are subjected to hydrolysis or acid decomposition, if necessary, to give the compound of the formula (I) wherein $R^7$ is a hydrogen atom. The hydrolysis is carried out by a conventional method, for example, by reacting with an alkali metal hydroxide (e.g., sodium hydroxide, potassium hydroxide) in a suitable solvent. The solvent used includes, for example, methanol, ethanol, tetrahydrofuran, water, and these solvents may be used alone or in the form of a mixture of two or more of these solvents. The acid decomposition is carried out, for example, by treating with an organic acid (e.g., trifluoroacetic acid, methanesulfonic acid, trifluoromethanesulfonic acid, etc.) or an inorganic acid (e.g., hydrogen chloride, hydrochloric acid, etc.). The solvent used includes, for example, diethyl ether, dichloromethane, ethyl acetate, dioxane, methanol, ethanol, etc., and these solvents may be used alone or in the form of a mixture of two or more of these solvents. The reaction temperature is usually in the range of –10° C. to 50° C.

The starting compound (III) of this reaction may be commercially available ones or may be prepared by a conventional method. For example, α,β-diaminopropanoic acid derivatives may be prepared by the methods disclosed in J. Am. Chem. Soc., 114, 998 (1992); J. Med. Chem., 24, 554 (1981); J. Med. Chem., 40, 1779 (1997); Bioorg. Med. Chem., 5, 693 (1997); J. Org. Chem., 62, 6918 (1997), or a modified method thereof. β-Substituted-β-amino propanoic acid derivatives may be prepared by the method disclosed in J. Med. Chem., 42, 5254 (1999), or a modified method thereof. Aspartic acid derivatives or glutamic acid derivatives may be prepared by the methods disclosed in J. Am. Chem. Soc., 75, 4610 (1953); J. Chem. Soc., Perkin Trans.

I, 855 (1999); Tetrahedron Lett., 35, 5243 (1994); Bioorg. Med. Chem. Lett., 6, 1403 (1996), or a modified method thereof. β-Aryloxycarbonylamino-α-aminopropanoic acid derivatives may be prepared by the methods disclosed in Bioorg. Med. Chem. Lett., 7, 1371 (1997); Bioorg. Med. Chem. Lett., 9, 853 (1999), or a modified method thereof. Another starting compound (II) of this reaction is prepared, for example, by the following Process (A) or Process (B).

Process (A):

The compound of the formula (II) wherein $W^1$, $W^2$, $W^3$ and $W^4$ are all —CH—, D is a nitrogen atom, E is —CH— or a nitrogen atom may be prepared, for example, by the method disclosed in the following Reaction Scheme.

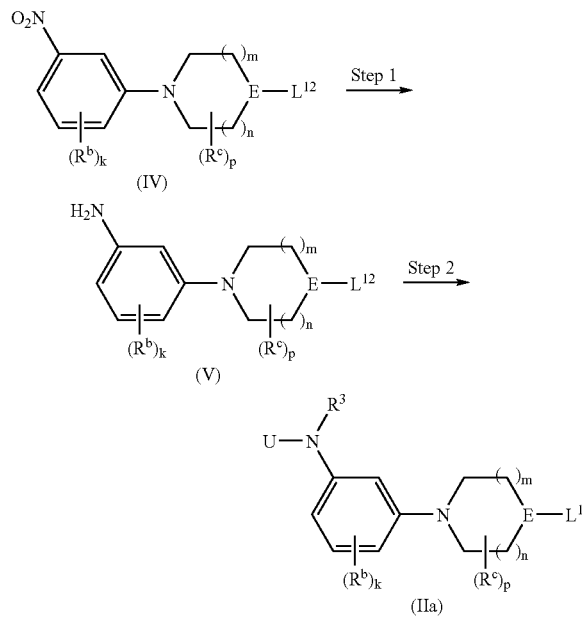

($L^{12}$ is an amino group, a protected amino group, a protected carboxyl group, a lower alkyloxycarbonyl group, or an aryloxycarbonyl group, and $L^1$, U, E, $R^b$, $R^c$, $R^3$, k, p, m and n are as defined above)

(Step 1)

This step is carried out by treating the compound of the formula (IV) in a suitable solvent with a reducing agent suitable for reduction of a nitro group into an aniline amino group, or by catalytic reduction. The reducing agent is, for example, a combination of a metal (e.g., iron, zinc, tin, etc.) or a metal salt (e.g., stannic chloride) and an acid or a salt thereof (e.g., hydrochloric acid, acetic acid, or ammonium acetate). Stannic chloride may be used alone. The catalytic reduction is carried out in the presence of a catalyst (e.g., palladium on carbon, platinum). The solvent used should be selected according to the kinds of the catalyst, etc., and includes, for example, ethanol, ethyl acetate, acetone, dimethylformamide, water, acetic acid, hydrochloric acid, etc., and these solvent may be used alone, or in the form of a mixture of two or more of these solvents. The reaction temperature may vary according to the kinds of the reducing agent or catalyst to be used, etc. and it is usually in the range of 30° C. to 150° C.

In this step, the starting compound (IV) may be prepared from unsubstituted or substituted arylboronic acid compounds, phenylpiperazine, phenylpiperidine or 3-nitrofluorobenzene by a conventional method, for example, by the methods disclosed in Tetrahedron Lett., 39, 7979 (1998); J. Med. Chem., 35, 4727 (1992); J. Med. Chem., 23, 1358 (1980); J. Med. Chem., 37, 2253 (1994); Tetrahedron, 55, 13285 (1999), or by a combination of these methods.

On the other hand, the unsubstituted or substituted arylboronic acid compounds, phenylpiperazine, phenylpiperidine or 3-nitrofluorobenzene, which is a starting compound of the compound (IV), may be commercially available one or may be prepared by a conventional method, for example, by the methods disclosed in J. Am. Chem. Soc., 54, 4415 (1932); J. Am. Chem. Soc., 53, 711 (1931); J. Med. Chem., a2, 1052 (1989); J. Med. Chem., 42, 3342 (1999); Tetrahedron, 55, 11399 (1999), or by a modified method thereof.

(Step 2)

This step is carried out, for example, by reacting the compound (V) with a reagent such as 1,3-bis(tert-butoxycarbonyl)-2(1H)-tetrahydropyrimidinethione, 2-methylthio-3,4,5,6-tetrahydropyrimidine-3-carboxylic acid alkyl ester, an isocyanic acid derivative, an isothiocyanic acid derivative, etc., followed by removing the protecting group such as tert-butoxycarbonyl, if necessary.

The solvent used should be selected according to the kinds of the starting compound, etc., and includes, for example, the same solvents as listed in the reaction of the compound (II) and the compound (III).

This reaction is carried out in the presence of a base or a catalyst if necessary, and the base includes, for example, ones as listed in the reaction of the compound (II) and the compound (III).

The catalyst includes, for example, mercury (II) chloride, mercury (II) oxide, copper (II) chloride, etc. The reaction temperature may vary according to the kinds of the starting compound, etc., and it is usually in the range of −30° C. to 200° C., preferably in the range of 0° C. to 70° C.

The compound of the formula (IIa) wherein $R^3$ is a group other than a hydrogen atom may be prepared by introducing a group: $R^3$ onto the aniline amino group of the compound of the formula (V), followed by introducing a group U in a similar manner as mentioned above. The introduction of the group $R^3$ onto the aniline amino group of the compound (V) is carried out, for example, by reductive alkylation reaction using an aldehyde compound such as formaldehyde, or an alkylation reaction using an alkyl halide or a dialkyl sulfate and a base.

When the product thus obtained has a protecting group such as tert-butoxycarbonyl group, said protecting group is removed by hydrolysis or acid decomposition in a suitable solvent to give the compound of the formula (IIa). Besides, the product thus obtained may be reacted with the compound of the formula (III) without further treatment, followed by removing the protecting group, to give the compound of the formula (I').

Process (B):

The compounds of the formula (IIb), wherein 1 to 3 groups of $W^1$, $W^2$, $W^3$ and $W^4$, and D is a nitrogen atom, and all $W^1$, $W^2$, $W^3$, $W^4$ and D are —CH—, may be prepared, for example, by the method disclosed in the following Reaction Scheme.

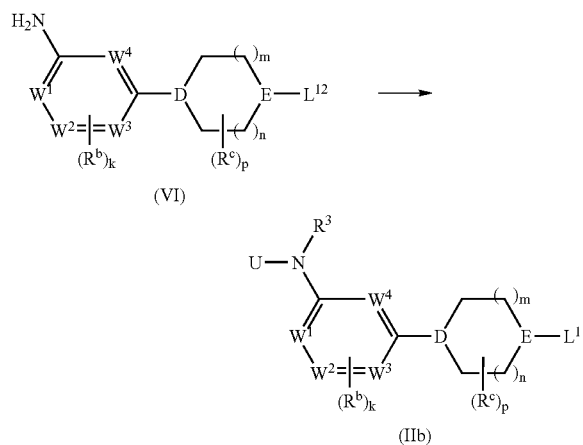

(wherein $L^{12}$, $L^1$, U, E, $R^b$, $R^c$, $R^3$, k, p, m and n are as defined above, and $W^1$, $W^2$, $W^3$, $W^4$ and D are as defined above)

Process (B) may be carried out according to the method of Step 2 of Process (A). The removal of the protecting group may be carried out according to the method as explained in Process (A).

The compound of the formula (VI) wherein 1 to 3 groups of $W^1$, $W^2$, $W^3$ and $W^4$, and D are a nitrogen atom may be prepared from a compound of the formula: $G^1$-A-$G^2$ ($W^1$, $W^2$, $W^3$ and $W^4$ in A are as defined above, $G^1$ is a halogen atom, an alkylthio, an alkylsulfinyl, or an alkylsulfonyl, $G^2$ is a hydrogen atom, an amino group, a nitro group, etc.), for example, halogenated pyridine, halogenated aminopyridine, halogenated pyridine N-oxide, halogenated nitropyridine N-oxide, halogenated pyrimidine, halogenated pyrazine, or halogenated triazine, by a conventional method, for example, by the methods disclosed in J. Org. Chem., 64, 8576 (1999); Tetrahedron Lett., 39, 5725 (1998); J. Med. Chem., 15, 295 (1972); Acta Pol. Pharm., 54, 55 (1997); J. Org. Chem., 18, 1484 (1953), or by a modified method thereof.

The unsubstituted or substituted halogenated pyridine, halogenated pyridine N-oxide, halogenated pyrimidine, etc., which are the starting compounds for the compound (VI), may be commercially available ones, or may be prepared by a conventional method, for example, by the methods disclosed in Acta. Chem. Scand., 47, 805 (1993); J. Prakt. Chem., 330, 154 (1988); J. Org. Chem., 21, 1077 (1956), or a modified method thereof.

The compound of the formula (VI) wherein $W^1$, $W^2$, $W^3$, $W^4$ and D are all carbon atoms may be prepared from unsubstituted or substituted trifluoromethanesulfonic acid vinyl esters by a conventional method, for example, by the methods disclosed in Synthesis, 993 (1991); Bioorg. Med. Chem. Lett., 10, 1625 (2000); Tetrahedron Lett., 41, 3705 (2000); J. Med. Chem., 43, 2703 (2000); J. Med. Chem., 16, 813 (1973), or by a modified method thereof.

The unsubstituted or substituted trifluoromethanesulfonic acid vinyl esters may be prepared by a conventional method, for example, by the methods disclosed in J. Am. Chem. Soc., 111, 8320 (1989); Can. J. Chem., 71, 1867 (1993); Tetrahedron, 53, 1391 (1997), or a modified method thereof.

The compound of the formula (I) may also be prepared according to the methods of Reference Examples 1, 2, 3, 4 and 5, and Examples 1 and 2 as mentioned below, that is, by reacting the compound of the formula (IV) wherein $L^{12}$ is converted into $L^1$, with the compound of the formula (III), followed by converting the nitro group of the product into a group: U-$NR^3$— according to Process (A).

The compound of the formula (I) may also be prepared according to the methods of Reference Examples 11, 12 and 17, and Examples 51 to 120 and 136 to 143 as mentioned below.

Other compounds of the formula (I) may be prepared by the above processes or a conventional method.

The compounds of the formula (I) obtained by the above Processes or a modified method thereof can be isolated and purified by a conventional method such as chromatography, recrystallization, reprecipitation, etc. The compound of the formula (I) can be obtained either in the form of an acid addition salt thereof or a salt with a base, according to the kinds of functional groups within the structure, the selection of the starting compounds, and reaction conditions, and these salts can be converted into the compound of the formula (I) by a conventional method. On the other hand, the compound of the formula (I) having a group being capable of forming an acid addition salt thereof within the structure thereof may be converted into an acid addition salt thereof by treating with various acids in a conventional manner. In addition, the compound of the formula (I) having a group being capable of forming a salt with a base within the structure thereof may be converted into a salt with a base by treating with various bases in a conventional manner.

The compound of the formula (I) having a pyridine nucleus may be converted into an N-oxide derivative of the pyridine nucleus by oxidizing under conventional N-oxidization conditions. The N-oxidization reaction is carried out by reacting the compound of the formula (I) with an oxidizing agent in a suitable solvent. The oxidizing agent includes, for example, hydrogen peroxide and an organic peracid such as peracetic acid, perbenzoic acid, m-chloroperoxybenzoic acid, etc. The oxidizing agent is usually used in an amount of about 0.9 to about 2 equivalents to 1 equivalent of the compound of the formula (I). The solvent used be selected according to the kinds of oxidizing agents, etc., and includes, for example, water, acetic acid, methanol, acetone, dioxane, dichloromethane, chloroform. The reaction temperature may vary according to the kinds of the oxidizing agent, but it is usually in the range of about −30° C. to about 100° C., preferably in the range of about −20° C. to about 30° C.

The pharmacological activities of the present compounds are explained by the following pharmacological experiments on the representative compounds of the present invention.

Experiment 1: Assay for the Inhibition of αvβ3 integrin binding

This experiment was carried out based on the method described in Coron. Artery Dis., 7, 767 (1996), using vitronectin as a ligand.

Purified human αvβ3 integrin (Chemicon International, Inc., USA) was adjusted to a concentration of 1 μg/ml with TBS++ [20 mM Tris-HCl (pH 7.4), 150 mM NaCl, 1 mM CaCl$_2$, 1 mM MgCl$_2$], and the diluted solution was added to plates (Labsystems, Finland) at 50 μl/well. The plate was left at 4° C. overnight for immobilization of the αvβ3 integrin. All subsequent steps were done at 25° C., and the procedure for each well was described hereafter.

The solution was discarded, and then 200 μl of TBS++ containing 1% BSA (Wako Pure Chemical Industries, Ltd., Japan) was added to the well and left for one hour for blocking. The well was washed with a wash solution (TBS++ containing 0.01% Tween 20) 4 times, and 50 µl of a reaction solution (TBS++ containing 0.1% BSA and 0.01% Tween 20) was added to the well. Subsequently, 25 µl of a test compound solution adjusted to each concentration with the reaction solution was added, and then mixed with 25 µl of biotinylated (Amersham Pharmacia Biotech, UK) human vitronectin (Gibco BRL, USA) adjusted to 0.4 µg/ml with the reaction solution. The mixture was reacted for 2 hours. After washing 4 times with the wash solution, 100 µl of peroxidase-labeled streptoavidin (Amersham Pharmacia Biotech, UK) diluted 1:500 with the reaction solution was added to the well. Following 30 minutes reaction, the well was washed 4 times with the wash solution, and 100 µl of a TMB substrate solution (Bio-Rad Laboratories, USA) was added to the well. Color was developed for 20 minutes and the reaction was stopped by adding 100 µl of 0.5 M sulfuric acid.

The absorbance at 450 nm was measured with a plate reader (Molecular Devices, USA) to obtain a total binding. To obtain a nonspecific binding, EDTA adjusted to 20 mM with the reaction solution was added instead of the test compound solution. A specific binding was calculated by subtracting the nonspecific binding from the total binding. Inhibitory activity of the test compound on αvβ3 integrin binding was expressed as $IC_{50}$ value, exhibiting a concentration of the test compound required to inhibit the specific binding of vitronectin to αvβ3 integrin by 50%. For reference, when a synthesized RGD peptide (Gibco BRL, USA, GPenGRGDSPCA) was tested in this assay system, the $IC_{50}$ value of the peptide was 3.0 nM.

The results of the inhibition assay of the αvβ3 integrin binding are shown in the following Table 2 together with the results of that of αIIbβ3 integrin binding.

Experiment 2: Assay for the Inhibition of αIIbβ3 Integrin Binding

This experiment was carried out based on the method described in Thromb. Haemostasis, 75, 339 (1996), Blood, 93, 2559 (1999), using fibrinogen as a ligand. According to the method described in the above literatures, assay for the inhibition of αIIbβ3 integrin binding can be achieved by capturing αIIbβ3 integrin from platelet lysate with the use of an activated antibody against αIIbβ3 integrin.

Human platelets were isolated in a conventional manner. At 25° C., the isolated platelets were adjusted to a concentration of $1.25 \times 10^9$/ml with TBS+[50 mM Tris-HCl (pH 7.4), 150 mM NaCl, 2 mM $CaCl_2$], and then ⅛ volume of TBS+ containing 2 mM leupepsin and 10 mM PMSF was added and stirred gently. Nest, ⅙ volume of TBS+ containing 10% Triton X-100 was added and stirred gently. After standing on ice for 30 minutes, a platelet lysate was prepared from the mixture by discarding the insoluble fraction with centrifugation (10,000 g, 15 minutes).

Anti-mouse IgG goat antibody (Jackson Immunoresearch Laboratories, Inc., USA) was adjusted to a concentration of 5 µg/ml with sodium carbonate buffer (pH 9.6) and added to plates at 50 µl/well. The plate was left at 4° C. overnight for immobilization of the antibody. All subsequent steps were done at 25° C., and the procedure for each well was described hereafter.

The well was washed once with TBS+, and then 200 µl of TBS+ containing 5% BSA was added to the well and left for one hour for blocking. The well was washed with a reaction solution (TBS+ containing 0.1% BSA and 0.05% Triton X-100) 4 times, and then 50 µl of anti-human αIIbβ3 integrin activated monoclonal antibody (TAKARA SHUZO CO., LTD, Japan, PT25-2 strain) adjusted to 5 µg/ml with the reaction solution was added to the well. After one hour reaction, the well was washed 4 times with the reaction solution, and 50 µl of the platelet lysate diluted 1:2 with the reaction solution was added to the well. Following 2 hours reaction, the well was washed 4 times with the reaction solution, and 50 µl of the reaction solution was added to the well. Subsequently, 25 µl of a test compound solution adjusted to each concentration with the reaction solution was added, and then mixed with 25 µl of biotinylated fibrinogen (Calbiochem, Germany) adjusted to 2 µg/ml with the reaction solution. The mixture was reacted for one hour. After washing 4 times with the reaction solution, 100 µl of alkaline phosphatase-labeled streptoavidin (Gibco BRL, USA) diluted 1:500 with the reaction solution was added to the well. Following 30 minutes reaction, the well was washed 4 times with the wash solution. Next, 50 µl of the NaDPH solution (Invitrogen, former company name: Gibco BRL, USA) was added and reacted for 20 minutes, and then 50 µl of an amplification solution containing diaphorase and alcohol dehydrogenase (Invitrogen, former company name: Gibco BRL, USA) was added. Color was developed for 20 minutes and the reaction was stopped by adding 50 µl of 0.5 M sulfuric acid.

The absorbance at 495 nm was measured with a plate reader to obtain a total binding. To obtain a nonspecific binding, EDTA adjusted to 20 mM with the reaction solution was added instead of the test compound solution. A specific binding was calculated by subtracting the nonspecific binding from the total binding. Inhibitory activity of the test compounds on the αIIbβ3 integrin binding was expressed as $IC_{50}$ value, exhibiting a concentration of the test compound required to inhibit the specific binding of fibrinogen to αIIbβ3 integrin by 50%. For reference, when an αIIbβ3 integrin inhibitor, tirofiban hydrochloride, was tested in this assay system, the $IC_{50}$ value of the inhibitor was 0.28 nM.

TABLE 2

| Inhibitory activities on αvβ3 and αIIbβ3 integrin binding | | | | | |
|---|---|---|---|---|---|
| Test | $IC_{50}$ (nM) | | Test | $IC_{50}$ (nM) | |
| comp. | αvβ3 | αIIbβ3 | comp. | αvβ3 | αIIbβ3 |
| Ex. 2 | 0.060 | 43 | Ex. 9 | 0.059 | 54 |
| Ex. 10 | 0.075 | 74 | Ex. 11 | 0.14 | 87 |
| Ex. 12 | 0.057 | 95 | Ex. 13 | 0.042 | 59 |
| Ex. 18 | 0.13 | 310 | Ex. 19 | 0.032 | 100 |
| Ex. 20 | 0.061 | 37 | Ex. 30 | 5.1 | 4600 |
| Ex. 44 | 0.11 | 800 | Ex. 50 | 0.065 | 13 |
| Ex. 86 | 0.094 | 380 | Ex. 87 | 0.10 | 110 |
| Ex. 88 | 0.051 | 26 | Ex. 89 | 0.10 | 96 |
| Ex. 90 | 0.23 | 260 | Ex. 92 | 0.066 | 72 |
| Ex. 93 | 0.20 | 150 | Ex. 94 | 0.21 | 60 |
| Ex. 95 | 0.36 | 940 | Ex. 96 | 0.080 | 60 |
| Ex. 97 | 5.1 | 1000< | Ex. 98 | 5.7 | 580 |
| Ex. 99 | 0.87 | 480 | Ex. 100 | 0.62 | 180 |
| Ex. 101 | 0.74 | 450 | Ex. 102 | 3.0 | 1100 |
| Ex. 103 | 3.9 | 960 | Ex. 104 | 2.5 | 210 |
| Ex. 105 | 0.75 | 430 | Ex. 106 | 1.4 | 280 |
| Ex. 107 | 0.65 | 350 | Ex. 108 | 1.4 | 650 |
| Ex. 110 | 0.20 | 110 | Ex. 111 | 0.075 | 96 |
| Ex. 112 | 0.10 | 24 | Ex. 113 | 0.45 | 320 |
| Ex. 114 | 0.44 | 190 | Ex. 115 | 0.25 | 73 |
| Ex. 117 | 0.35 | 88 | Ex. 118 | 0.72 | 270 |
| Ex. 119 | 0.35 | 150 | Ex. 120 | 0.47 | 160 |
| Ex. 121 | 0.058 | 660 | Ex. 122 | 0.16 | 720 |
| Ex. 123 | 0.056 | 1600 | Ex. 124 | 0.063 | 540 |
| Ex. 125 | 0.15 | 340 | Ex. 126 | 0.38 | 1000< |
| Ex. 127 | 0.055 | 1000< | Ex. 128 | 0.30 | 1000< |
| Ex. 129 | 0.39 | 1000< | Ex. 130 | 0.058 | 1000< |
| Ex. 131 | 0.30 | 57 | Ex. 132 | 1.7 | 1000< |
| Ex. 133 | 0.26 | 1000< | Ex. 134 | 0.64 | 1000< |

TABLE 2-continued

Inhibitory activities on αvβ3 and αIIbβ3 integrin binding

| Test comp. | IC$_{50}$ (nM) αvβ3 | IC$_{50}$ (nM) αIIbβ3 | Test comp. | IC$_{50}$ (nM) αvβ3 | IC$_{50}$ (nM) αIIbβ3 |
|---|---|---|---|---|---|
| Ex. 135 | 0.74 | 1000< | Ex. 136 | 0.59 | 1000< |
| Ex. 137 | 0.28 | 880 | Ex. 138 | 0.32 | 1000< |
| Ex. 139 | 6.8 | 1000< | Ex. 140 | 0.22 | 30 |
| Ex. 142 | 3.6 | 1000< | Ex. 143 | 1.4 | 1000< |
| Ex. 145 | 0.041 | 380 | Ex. 146 | 1.0 | 4200 |
| Ex. 148 | 0.17 | 420 | Ex. 150 | 0.081 | 52 |
| Ex. 151A | 0.074 | 37 | Ex. 151B | 1.9 | 510 |
| Ex. 152 | 0.055 | 13 | Ex. 153 | 0.14 | 94 |
| Ex. 154 | 0.096 | 530 | Ex. 155 | 0.077 | 1000 |
| Ex. 156 | 0.055 | 43 | Ex. 157 | 0.048 | 10 |
| Ex. 158 | 0.14 | 750 | Ex. 159 | 0.060 | 86 |
| Ex. 160 | 0.046 | 67 | Ex. 161 | 0.10 | 77 |
| Ex. 162 | 0.21 | 1000< | | | |

(Note)
Example 151A and Example 151B indicate Stereoisomer A and Stereoisomer B respectively.

As is clearly shown in Table 2, the compounds of the present invention showed marked inhibitory activities on αvβ3 integrin binding. Most of the tested compounds potently inhibited αvβ3 integrin binding, exhibiting IC$_{50}$ value of 1 nM or less. On the other hand, these compounds exhibited much higher IC$_{50}$ values of inhibitory activity on αIIbβ3 integrin binding than that on αvβ3 integrin binding, and the difference between the two IC$_{50}$ values was 100 times or more in all of the tested compounds. Therefore, it was revealed that the compounds of the present invention have an excellent selectivity for αvβ3 integrin as opposed to αIIbβ3 integrin.

As is shown in the above experimental results, the compounds (I) of the present invention, a prodrug thereof, a pharmaceutically acceptable salt thereof or an N-oxide thereof, or a hydrate or a solvate thereof (hereinafter, occasionally referred to as the compounds of the present invention) have a high selectivity for αvβ3 integrin as well as a potent inhibitory activity and a low toxicity, and hence, the present compound may be used as a preventive or/and therapeutic agent for diseases in which αvβ3 integrin is involved, that is, diseases in which the inhibition of cell adhesion, migration and/or proliferation is effective for treatment. For example, the present compound is useful as antirestenotic agents, antiarteriosclerotic agents, anticancer agents, anti-osteoporosis agents, antiinflammatory agents, antiimmune agents, and therapeutic agents for eye diseases, which are indicated for the prevention and/or treatment of diseases related to poop muscle cell (e.g., restenosis after PTCA or vascular grafting, angina, myocardial infarction, atherosclerosis), diseases related to angiogenesis (e.g., cancer, retinopathy, rheumatoid arthritis, psoriasis), diseases related to osteoclast (e.g., osteoporosis, hypercalcemia, Paget's disease, osteitis deformans, arthritis, periodontal disease), diseases related to macrophage (e.g., inflammatory diseases, atherosclerosis), diseases related to fibroblast (e.g., intraperitoneal adhesion), cancer metastasis, or viral infections The compounds of the present invention can be administered either orally, parenterally, rectally or intravaginally. The dose of the compounds of the present invention may vary according to the kinds of the compound, the administration routes, the conditions, ages of the patients, etc., but it is usually in the range of 0.01–50 mg/kg/day, preferably in the range of 0.1–10 mg/kg/day, once a day or divided into several dosage forms.

The compounds of the present invention are usually administered in the form of a pharmaceutical preparation, which is prepared by mixing thereof with a pharmaceutically acceptable carrier or diluent. The pharmaceutical preparation is, for example, oral preparations such as tablets, capsules, granules, powders, syrups, etc., external preparations such as inhalants, nasal drops, ointments, patches, etc., injection preparations such as intravenous injections, subcutaneous injections, intramuscular injections, etc., drip infusions, suppositories, etc. These pharmaceutical compositions may be prepared by a conventional method.

The pharmaceutically acceptable carrier or diluent may be any conventional ones usually used in the pharmaceutical field, and does not react with the compounds of the present invention. Suitable examples of the pharmaceutically acceptable carrier or diluent for preparing tablets, capsules, granules and powders are, for example, excipients such as lactose, corn starch, white sugar, mannitol, calcium sulfate, crystalline cellulose, etc., disintegrants such as carmellose sodium, pregelatinized starch, carmellose calcium, etc., binders such as methylcellulose, gelatin, gum arabic, ethylcellulose, hydroxypropyl cellulose, polyvinylpyrrolidone, etc., lubricants such as light anhydrous silicic acid, magnesium stearate, talc, hydrogenated oil, etc. Tablets may be coated in a conventional manner with a coating agent such as carnauba wax, hydroxypropylmethylcellulose, macrogol, hydroxypropylmethyl phthalate, cellulose acetate phthalate, white sugar, titanium oxide, sorbitan fatty acid esters, calcium phosphate, etc.

Suitable examples of the pharmaceutically acceptable carrier or diluent for preparing syrups are sweetening agents such as white sugar, glucose, fructose, etc., suspending agents such as gum arabic, tragacanth, carmellose sodium, methylcellulose, sodium alginate, crystalline cellulose, bee gum, etc., dispersing agents such as sorbitan fatty acid ester, sodium lauryl sulfate, polysorbate 80, etc. If necessary, corrigents, flavors, preservatives may be added to syrups. Syrups may be in the form of a dry syrup, which is dissolved or suspended when used.

Suitable examples of the bases for suppositories are cacao butter, saturated fatty acid glycerin ester, glycerogelatin, macrogol. If necessary, surfactants, preservatives may be added to suppositories.

Injection preparations may be prepared by dissolving an acid addition salt of the compound (I) of the present invention in a distilled water for injection, but if necessary, there may be added solubilizing agents, buffering agents, pH adjusters, isotonic agents, soothing agents, preservatives. Moreover, injection preparations may be in the form of a suspension, which is prepared by suspending the compound of the present invention per se in distilled water for injection or a vegetable oil. In these cases, if necessary, bases, suspending agents, thickening agents may be added thereto. Further, injection preparations may be in the form of powder or may be lyophilized, and it is dissolved when used, and in these cases, if necessary, excipients, etc. may be added thereto.

The content of the compound of the present invention in pharmaceutical compositions may vary based on the dosage forms, and it is usually in the range of 1 to 70% by weight, preferably in the range of 5 to 50% by weight, to the total weight of the pharmaceutical composition. These preparations may also contain other therapeutically effective compounds as well.

BEST MODE FOR CARRYING OUT THE INVENTION

The present invention will be illustrated in more detail by Reference Examples and Examples, but it should not be construed to be limited thereto. The compounds were identified by Elementary Analysis, Mass spectrum, IR spectrum, NMR spectrum, HPLC (High Performance Liquid Chromatography), etc.

The conditions for HPLC are as follows:
Column: CAPCELL PAK C18 SG 120 (manufactured by Shiseido Co., Ltd.), 4.6φ×150 mm),
Temperature: 40° C.,
Flow: 1 ml/min.,
Eluent: gradient 10% to 100% acetonitrile/0.05% aqueous trifluoroacetic acid solution over 25 minutes.
UV detection at 254 nm.

The eluent for the products of Examples 48, 105 and 120 was 0% to 100% acetonitrile/0.05% aqueous trifluoroacetic acid solution.

The following abbreviations may be used in the following Reference Examples and Examples in order to simplify the description.

Boc: tert-butoxycarbonyl group
Bu: butyl group
Bu$^t$: tert-butyl group
Et: ethyl group
Me: methyl group
i-Pr: isopropyl group
Isoxz: isoxazolyl group
Naph: naphthyl group
Ph: phenyl group
Py: pyridyl group
Rt: Retention time
TFA: trifluoroacetic acid In addition, in the following Reference Examples and Examples, the compound name may optionally be expressed as "compound of Reference Example ○" or "compound of Example Δ" for simplification. Such expressions are used instead of chemical names of the title compounds of Reference Example ○ or Example Δ.

REFERENCE EXAMPLE 1

Preparation of 1-(3-nitrophenyl)piperidine-4-carboxylic acid ethyl ester:

To a solution of 4-piperidinecarboxylic acid ethyl ester (25.0 g) and 3-nitrophenylboronic acid (31.9 g) in dichloromethane (1.0 L) are added pyridine (64.8 ml), anhydrous copper (II) acetate (28.9 g) and Molecular Sieves 4 Å (500 g), and the mixture was stirred at 25° C. for 3 days. The reaction solution is poured into 10% aqueous citric acid solution, and the mixture was extracted with ethyl acetate. The organic layer was successively washed with aqueous sodium hydrogen carbonate solution and saturated brine, and the solvent is evaporated under reduced pressure to give the title compound.

REFERENCE EXAMPLE 2

Preparation of 1-(3-nitrophenyl)piperidine-4-carboxylic Acid:

The compound of Reference Example 1 is dissolved in a mixture of methanol (300 ml) and tetrahydrofuran (100 ml), and thereto is added 2M aqueous sodium hydroxide solution (200 ml), and the mixture is stirred at 25° C. for one day. Methanol and tetrahydrofuran are evaporated under reduced pressure, and the aqueous layer is washed with toluene. The aqueous layer was acidified with conc. hydrochloric acid, and the precipitates are collected by filtration to give the title compound (10 g).

REFERENCE EXAMPLE 3

Preparation of (2S)-2-benzyloxycarbonylamino-3-[[1-(3-nitrophenyl)piperidin-4-yl]carbonylamino]propanoic acid methyl ester:

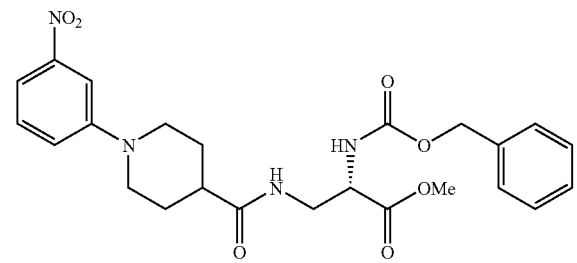

To a solution of the compound of Reference Example 2 (10 g) in dimethylformamide (200 ml) are added successively (2S)-3-amino-2-(benzyloxycarbonylamino)propanoic acid methyl ester hydrochloride (13.9 g), 1-hydroxybenzotriazole (6.1 g), ethyldiisopropylamine (27.7 ml) and 1-ethyl-3-(3-dimethylaminopropyl)carbodiimide hydrochloride (15.3 g), and the mixture was stirred at 25° C. overnight. The reaction solution is diluted with ethyl acetate, and washed successively with 10% aqueous citric acid solution, saturated aqueous sodium hydrogen carbonate solution and saturated brine, dried over magnesium sulfate, and the solvent is evaporated under reduced pressure to give the title compound.

REFERENCE EXAMPLE 4

Preparation of (2S)-3-[[1-(3-aminophenyl)piperidin-4-yl] carbonylamino]-2-(benzyloxycarbonylamino)propanoic acid methyl ester:

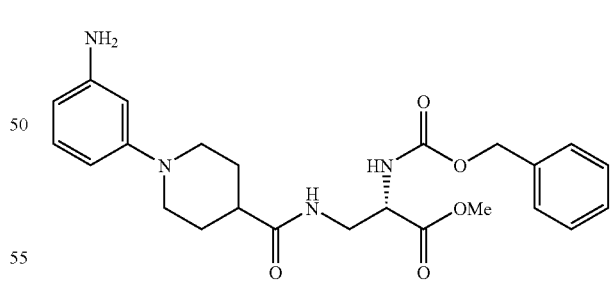

The compound of Reference Example 3 is dissolved in a mixture of ethanol (300 ml) and water (300 ml), and thereto are added iron (6.7 g) and ammonium chloride (6.4 g), and the mixture is stirred at 90° C. for 4 hours. The reaction solution is extracted with chloroform, and the organic layer is dried over magnesium sulfate, and the solvent is evaporated under reduced pressure. The residue is purified by silica gel column chromatography (eluent: gradient, 0% to 5% methanol/chloroform) to give the title compound (16.2 g).

REFERENCE EXAMPLE 5

Preparation of (2S)-3-[[1-[3-[1,3-bis(tert-butoxycarbonyl)hexahydropyrimidin-2-ylidene]aminophenyl]piperidin-4-yl]carbonylamino]-2-(benzyloxycarbonylamino)propanoic acid methyl ester:

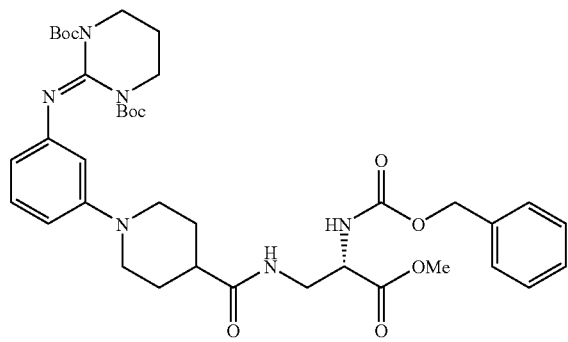

To a solution of the compound of Reference Example 4 (16.2 g) and 1,3-bis(tert-butoxycarbonyl)-2(1H)-tetrahydropyrimidinethione (16.9 g) in dimethylformamide (100 ml) are added triethylamine (9.9 ml) and mercury (II) chloride (14.5 g), and the mixture is stirred at 25° C. overnight. The reaction solution is filtered, and the solvent is evaporated under reduced pressure. The residue is purified by silica gel column chromatography (eluent: gradient, 0% to 5% methanol/chloroform) to give the title compound (20 g).

REFERENCE EXAMPLE 6

Preparation of 1-(3-aminophenyl)piperidine-4-carboxylic acid ethyl ester:

The compound of Reference Example 1 (1.7 g) is dissolved in a mixture of ethanol (50 ml) and water (50 ml), and thereto are added iron (1.0 g) and ammonium chloride (970 mg), and the mixture is stirred at 90° C. for 4 hours. The reaction solution is extracted with chloroform, and the organic layer is dried over magnesium sulfate, and the solvent is evaporated under reduced pressure. The residue is purified by silica gel column chromatography (eluent: gradient, 0% to 100% ethyl acetate/hexane) to give the title compound.

REFERENCE EXAMPLE 7

Preparation of 1-[3-(benzylaminocarbonyl)aminophenyl]piperidine-4-carboxylic acid:

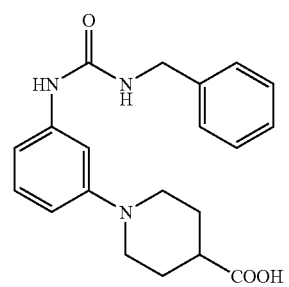

To a solution of the compound of Reference Example 6 in dichloromethane (50 ml) are added ethyldiisopropylamine (1.5 ml) and benzyl isocyanate (1.1 ml), and the mixture is stirred at 25° C. overnight. The reaction solution is concentrated under reduced pressure, and the residue is dissolved in a mixture of methanol (100 ml) and tetrahydrofuran (100 ml), and then thereto is added 2M aqueous sodium hydroxide solution (50 ml), and the mixture is stirred at 25° C. overnight. The reaction solution is concentrated under reduced pressure, and the resultant is acidified. The supernatant is removed by decantation, and the resulting gummy compound is dried to give the title compound.

REFERENCE EXAMPLE 8

Preparation of 1-[3-[1,3-bis(tert-butoxycarbonyl)hexahydropyrimidin-2-ylidene]aminophenyl]piperidine-4-carboxylic acid ethyl ester:

To a solution of the compound of Reference Example 6 (1.68 g) and 1,3-bis(tert-butoxycarbonyl)-2(1H)-tetrahydropyrimidinethione (3.8 g) in dimethylformamide (50 ml) are added triethylamine (3.36 ml) and mercury (II) chloride (3.28 g), and the mixture is stirred at 25° C. overnight. The reaction solution is filtered, and the solvent is evaporated under reduced pressure. The residue is purified by silica gel column chromatography (eluent: gradient, 0% to 100% ethyl acetate/hexane) to give the title compound (2.1 g).

REFERENCE EXAMPLE 9

Preparation of 1-[3-[1,3-bis(tert-butoxycarbonyl)hexahydropyrimidin-2-ylidene]aminophenyl]piperidine-4-carboxylic Acid:

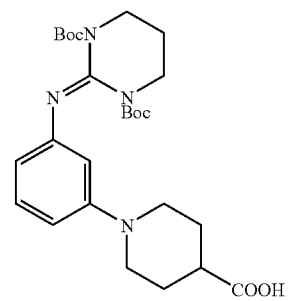

To a solution of the compound of Reference Example 8 (2.1 g) in methanol (100 ml) is added 2M aqueous sodium hydroxide solution (100 ml), and the mixture is stirred at 25° C. for one day. Methanol is evaporated under reduced pressure, and the aqueous layer is washed with toluene, and acidified with 10% aqueous citric acid solution, and then extracted with ethyl acetate. The organic layer is dried over sodium sulfate, and the solvent is evaporated under reduced pressure to give the title compound (780 mg).

REFERENCE EXAMPLE 10

Preparation of (2S)-3-[[1-[3-[1,3-bis(tert-butoxycarbonyl)hexahydropyrimidin-2-ylidene]aminophenyl]piperidin-4-yl]carbonylamino]-2-(isopropoxycarbonylamino)propanoic acid methyl ester:

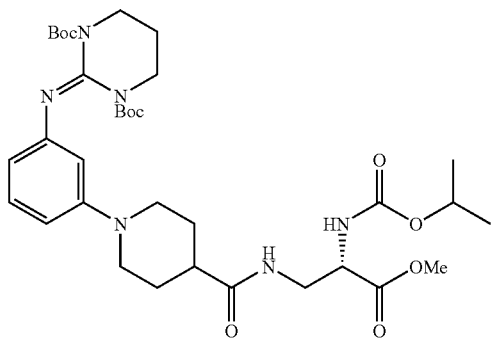

To a solution of the compound of Reference Example 9 (180 mg) in dimethylformamide (2 ml) are successively added (2S)-3-amino-2-(isopropoxycarbonylamino)propanoic acid methyl ester hydrochloride (172 mg), 1-hydroxybenzotriazole (54 mg), ethyldiisopropylamine (0.31 ml) and 1-ethyl-3-(3-dimethylaminopropyl)carbodiimide hydrochloride (200 mg), and the mixture is stirred at 25° C. overnight. The reaction solution is diluted with ethyl acetate, and washed successively with 10% aqueous citric acid solution, saturated aqueous sodium hydrogen carbonate solution and saturated brine, dried over magnesium sulfate, and the solvent is evaporated under reduced pressure to give the title compound.

REFERENCE EXAMPLE 11

Preparation of (2S)-2-amino-3-[[1-[3-[1,3-bis(tert-butoxycarbonyl)hexahydropyrimidin-2-ylidene]aminophenyl]piperidin-4-yl]carbonylamino]-propanoic acid methyl ester:

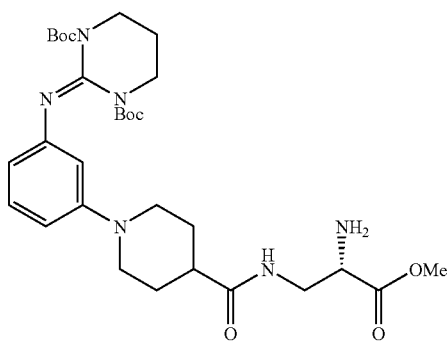

To a solution of the compound of Reference Example 5 (2.0 g) in ethanol (50 ml) is added 10% palladium on carbon (wet, 2.0 g), and the mixture is stirred at 25° C. under hydrogen atmosphere for 5 hours. The catalyst is removed by filtration, and the filtrate is concentrated under reduced pressure, and the residue is purified by silica gel column chromatography (eluent: gradient, 0% to 15% methanol/chloroform) to give the title compound (700 mg).

REFERENCE EXAMPLE 12

Preparation of (2S)-3-[[1-[3-[1,3-bis(tert-butoxycarbonyl)hexahydropyrimidin-2-ylidene]aminophenyl]piperidin-4-yl]carbonylamino]-2-(ethoxycarbonylamino)propanoic acid methyl ester:

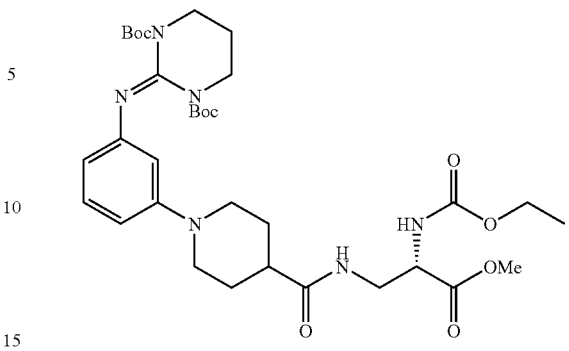

To a solution of the compound of Reference Example 11 (150 mg) in dichloromethane (5 ml) are added ethyldiisopropylamine (0.25 ml) and ethyl chloroformate (0.1 ml), and the mixture is stirred at 25° C. overnight. The reaction solution is concentrated under reduced pressure, and the residue is purified by silica gel column chromatography (eluent: gradient, 0% to 100% ethyl acetate/hexane) to give the title compound.

REFERENCE EXAMPLE 13

Preparation of 1-(3-nitrophenyl)piperazine Hydrochloride:

A solution of 3-fluoronitrobenzene (250 g) and piperazine (900 g) in dimethylsulfoxide (1.5 L) is stirred at 100° C. for 18 hours. The reaction solution is diluted with water and ethyl acetate, and the organic layer is successively washed with water and saturated brine, and a 4M solution of hydrogen chloride in ethyl acetate is added to the organic layer. The resulting precipitates are collected by filtration to give the title compound (408 g).

REFERENCE EXAMPLE 14

Preparation of (2S)-2-benzyloxycarbonylamino-5-[4-(3-nitrophenyl)piperazin-1-yl]-5-oxopentanoic acid tert-butyl ester:

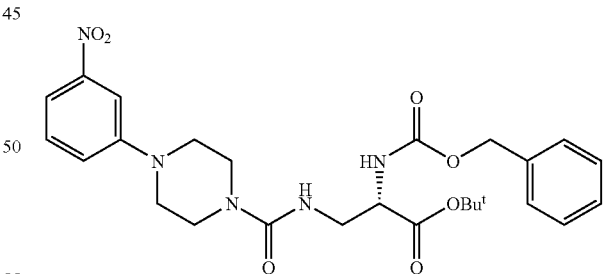

To a solution of the compound of Reference Example 13 (800 mg) in dimethylformamide (20 ml) are added successively N-benzyloxycarbonyl-L-glutamic acid α-tert-butyl ester (1.30 g), 1-hydroxybenzotriazole (591 mg), ethyldiisopropylamine (2.0 ml) and 1-ethyl-3-(3-dimethylaminopropyl)carbodiimide hydrochloride (1.47 g), and the mixture is stirred at 25° C. overnight. The reaction solution is diluted with ethyl acetate, washed successively with 10% aqueous citric acid solution, saturated aqueous sodium hydrogen carbonate solution and saturated brine, dried over magnesium sulfate, and the solvent is evaporated under reduced pressure. The residue is purified by silica gel column chromatography (eluent: gradient, 0% to 100% ethyl acetate/hexane) to give the title compound (1.4 g).

REFERENCE EXAMPLE 15

Preparation of (2S)-5-[4-(3-aminophenyl)piperazin-1-yl]-2-benzyloxycarbonylamino-5-oxopentanoic acid tert-butyl ester:

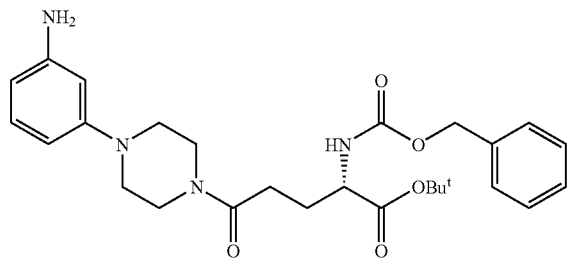

The compound of Reference Example 14 (1.0 g) is dissolved in a mixture of ethanol (100 ml) and water (100 ml), and thereto are added iron (313 mg) and ammonium chloride (302 mg), and the mixture is stirred at 90° C. for 4 hours. The reaction solution is extracted with chloroform, and the organic layer is dried over magnesium sulfate. The solvent is evaporated under reduced pressure, and the residue is purified by silica gel column chromatography (eluent: gradient, 0% to 100% ethyl acetate/hexane) to give the title compound (800 mg).

REFERENCE EXAMPLE 16

Preparation of (2S)-2-benzyloxycarbonylamino-5-[4-[3-[1,3-bis(tert-butoxycarbonyl)hexahydropyrimin-2-ylidene]aminophenyl]piperazin-1-yl]-5-oxopentanoic acid tert-butyl ester:

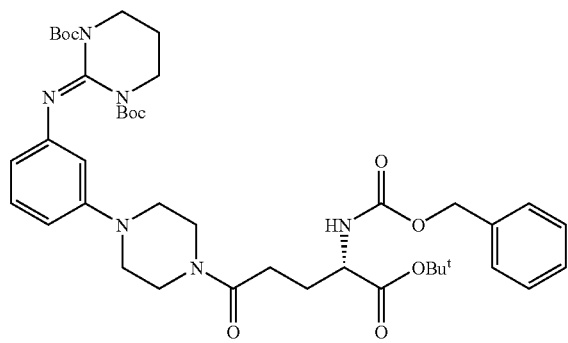

To a solution of the compound of Reference Example 15 (300 mg) and 1,3-bis(tert-butoxycarbonyl)-2(1H)-tetrahydropyrimidinethione (381 mg) in dimethylformamide (10 ml) are added triethylamine (0.336 ml), mercury (II) chloride (327 mg), and the mixture is stirred at 25° C. overnight. The reaction solution is filtered and the solvent is evaporated under reduced pressure. The residue is purified by silica gel column chromatography (eluent: gradient, 0% to 100% ethyl acetate/hexane) to give the title compound (230 mg).

REFERENCE EXAMPLE 17

Preparation of (2S)-2-amino-S-[4-[3-[1,3-bis(tert-butoxycarbonyl)hexahydropyrimidin-2-ylidene]aminophenyl]piperazin-1-yl]-5-oxo-pentanoic acid tert-butyl ester:

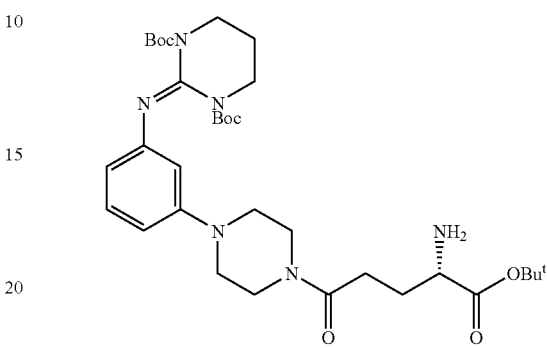

Using the compound of Reference Example 16 instead of the compound of Reference Example 5, the title compound is prepared in a similar manner to Reference Example 11.

REFERENCE EXAMPLE 18

Preparation of (2S)-2-benzyloxycarbonylamino-3-[[4-(3-nitrophenyl)piperazin-1-yl]carbonylamino]propanoic acid methyl ester:

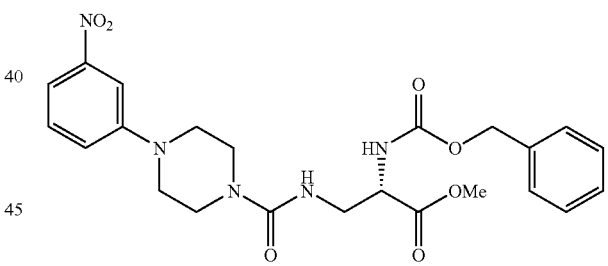

To a solution of the compound of Reference Example 13 (300 mg) and ethyldiisopropylamine (0.656 ml) in dichloromethane (10 ml) is added chloroformic acid p-nitrophenyl ester (273 mg), and the mixture is stirred at 25° C. for 6 hours. To the reaction solution are added a solution of (2S)-3-amino-2-(benzyloxycarbonylamino)propanoic acid methyl ester hydrochloride (709 mg) and ethyldiisopropylamine (0.65 ml) in dimethylformamide (20 ml), and the mixture is stirred at 60° C. overnight. The reaction solution is diluted with ethyl acetate, and then the mixture is washed successively with 10% aqueous citric acid solution, saturated aqueous sodium hydrogen carbonate solution, and saturated brine, dried over magnesium sulfate, and the solvent is evaporated under reduced pressure. The residue is purified by silica gel column chromatography (eluent: gradient, 0% to 100% ethyl acetate/hexane) to give the title compound (120 mg).

REFERENCE EXAMPLE 19

Preparation of (2S)-3-[[4-(3-aminophenyl)piperazin-1-yl]carbonylamino]-2-(benzyloxycarbonylamino)propanoic acid methyl ester:

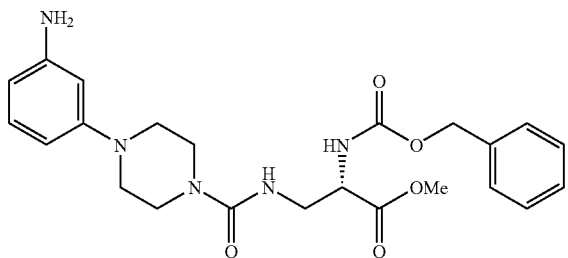

The compound of Reference Example 18 (100 mg) is dissolved in a mixture of ethanol (50 ml) and water (50 ml), and thereto are added iron (34 mg) and ammonium chloride (33 mg), and the mixture is stirred at 90° C. for 4 hours. The reaction solution is extracted with chloroform, and the organic layer is dried over magnesium sulfate, and the solvent is evaporated under reduced pressure. The residue is purified by silica gel column chromatography (eluent: gradient, 0% to 15% methanol/chloroform) to give the title compound (30 mg).

REFERENCE EXAMPLE 20

Preparation of (2S)-2-benzyloxycarbonylamino-3-[[4-[3-[1,3-bis(tert-butoxycarbonyl)hexahydropyrimidin-2-ylidene]aminophenyl]piperazin-1-yl]carbonylamino]propanoic acid methyl ester:

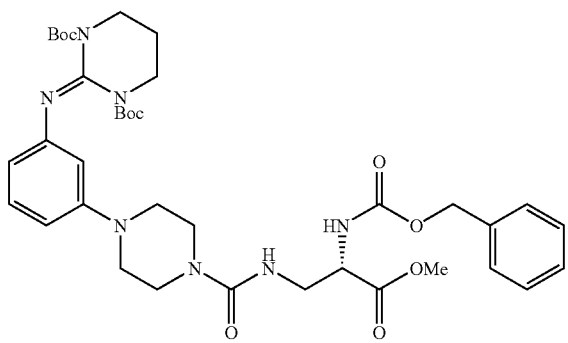

To a solution of the compound of Reference Example 19 (30 mg) and 1,3-bis(tert-butoxycarbonyl)-2(1H)-tetrahydropyrimidinethione (42 mg) in dimethylformamide (5 ml) are added triethylamine (0.036 ml) and mercury (II) chloride (35 mg), and the mixture is stirred at 25° C. overnight. The reaction solution is filtered, and the solvent is evaporated under reduced pressure, and the residue is purified by silica gel column chromatography (eluent: gradient, 0% to 15% methanol/chloroform) to give the title compound (25 mg).

REFERENCE EXAMPLE 21

Preparation of N-[1-(3-nitrophenyl)piperidin-4-yl]carbamic acid tert-butyl

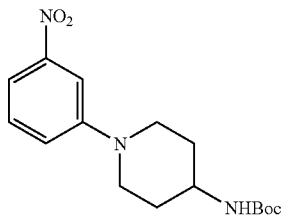

To a solution of N-(4-piperidyl)carbamic acid tert-butyl ester (2.0 g) and 3-nitrophenylboronic acid (2.5 g) in dichloromethane (100 ml) are added pyridine (4.07 ml), anhydrous copper (II) acetate (1.82 g) and Molecular Sieves 4 Å (100 g), and the mixture is stirred at 25° C. for 3 days. The reaction solution is poured into 10% aqueous citric acid solution, and the mixture is extracted with ethyl acetate. The organic layer is washed successively with aqueous sodium hydrogen carbonate solution and saturated brine, and the solvent is evaporated under reduced pressure to give the title compound (2.6 g).

REFERENCE EXAMPLE 22

Preparation of 4-amino-1-(3-nitrophenyl)piperidine trifluoroacetate:

To a solution of the compound of Reference Example 21 (1.0 g) in dichloromethane (10 ml) is added trifluoroacetic acid (10 ml), and the mixture is stirred at 25° C. for 3 hours. The solvent is evaporated under reduced pressure to give the title compound.

REFERENCE EXAMPLE 23

Preparation of (2S)-2-benzyloxycarbonylamino-4-[[1-(3-nitrophenyl)piperidin-4-yl]amino]-4-oxobutanoic acid tert-butyl ester:

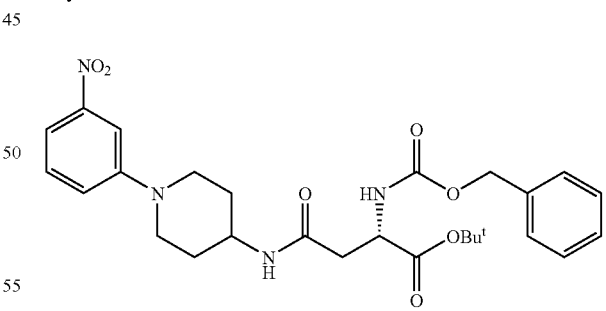

To a solution of the compound of Reference Example 22 in dimethylformamide (50 ml) are added successively N-benzyloxycarbonyl-L-aspartic acid α-tert-butyl ester (made by converting a dicyclohexylamine salt (1.72 g) into a free carboxylic acid using 10% aqueous citric acid solution), 1-hydroxybenzotriazole (476 mg), ethyldiisopropylamine (1.62 ml) and 1-ethyl-3-(3-dimethylaminopropyl)carbodiimide hydrochloride (1.19 g), and the mixture is stirred at 25° C. overnight. The reaction solution is diluted with ethyl acetate, washed successively with 10% aqueous citric acid solution, saturated aqueous sodium hydrogen carbonate solution, and saturated brine, dried over magnesium sulfate, and the solvent is evaporated under reduced pressure. The residue is purified by silica gel column chromatography (eluent: gradient, 0% to 100% ethyl acetate/hexane) to give the title compound (900 mg).

REFERENCE EXAMPLE 24

Preparation of (2S)-4-[[1-(3-aminophenyl)piperidin-4-yl]amino]-2-(benzyloxycarbonylamino)-4-oxobutanoic acid tert-butyl ester:

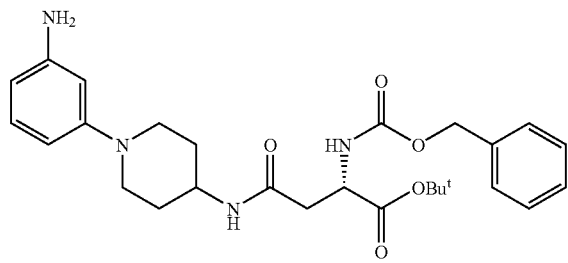

The compound of Reference Example 23 (900 mg) is dissolved in a mixture of ethanol (50 ml) and water (50 ml), and thereto are added iron (282 mg) and ammonium chloride (271 mg), and the mixture is stirred at 90° C. for 4 hours. The reaction solution is extracted with chloroform, and the organic layer is dried over magnesium sulfate, and the solvent is evaporated under reduced pressure. The residue is purified by silica gel column chromatography (eluent: gradient, 0% to 100% ethyl acetate/hexane) to give the title compound (500 mg).

REFERENCE EXAMPLE 25

Preparation of (2S)-2-benzyloxycarbonylamino-4-[[1-[3-[1,3-bis(tert-butoxycarbonyl)hexahydropyrimidin-2-ylidene]aminophenyl]piperidin-4-yl]amino]-4-oxobutanoic acid tert-butyl ester:

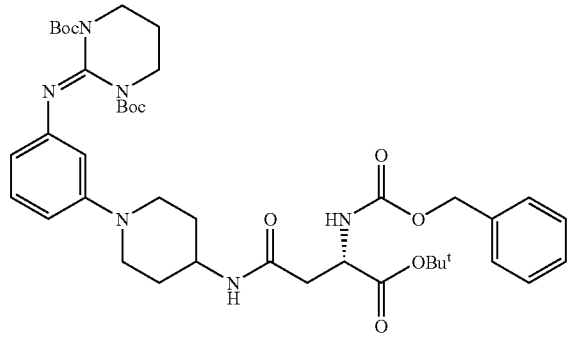

To a solution of the compound of Reference Example 24 (500 mg) and 1,3-bis(tert-butoxycarbonyl)-2(1H)-tetrahydropyrimidinethione (632 mg) in dimethylformamide (10 ml) are added triethylamine (0.556 ml), mercury (II) chloride (542 mg), and the mixture is stirred at 25° C. overnight. The reaction solution is filtered, and the solvent is evaporated under reduced pressure. The residue is purified by silica gel column chromatography (eluent: gradient, 0% to 100% ethyl acetate/hexane) to give the title compound (600 mg).

REFERENCE EXAMPLE 26

Preparation of 4-(3-aminophenyl)piperidin-1-carboxlic acid tert-butyl ester:

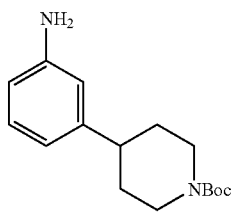

To a solution of 1,2,3,6-tetrahydro-4-(3-nitrophenyl)pyridine-1-carboxylic acid tert-butyl ester (1.7 g), which is prepared according to the method disclosed in Synthesis, 993 (1991), in ethanol (100 ml) is added 10% palladium on carbon (wet, 1.7 g), and the mixture is stirred at 25° C. under hydrogen atmosphere for 5 hours. The catalyst is removed by filtration, and the filtrate is concentrated under reduced pressure. The residue is purified by silica gel column chromatography (eluent: gradient, 0% to 100% ethyl acetate/hexane) to give the title compound (1.1 g).

REFERENCE EXAMPLE 27

Preparation of 4-[3-[1,3-bis(tert-butoxycarbonyl)hexahydropyrimidin-2-ylidene]aminophenyl]piperidine-1-carboxylic acid tert-butyl ester:

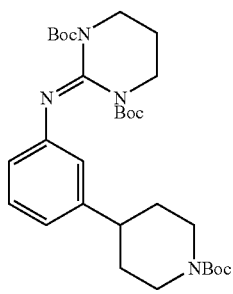

To a solution of the compound of Reference Example 26 (830 mg) and 1,3-bis(tert-butoxycarbonyl)-2(1H)-tetrahydropyrimidinethione (1.90 g) in dimethylformamide (10 ml) are added triethylamine (1.66 ml) and mercury (II) chloride (1.63 g), and the mixture is stirred at 25° C. overnight. The reaction solution is filtered, and the solvent is evaporated under reduced pressure, and the residue is purified by silica gel column chromatography (eluent: gradient, 0% to 100% ethyl acetate/hexane) to give the title compound (1.1 g).

REFERENCE EXAMPLE 28

Preparation of 4-[3-(1,4,5,6-tetrahydropyrimidin-2-yl)aminophenyl]-piperidine trifluoroacetate:

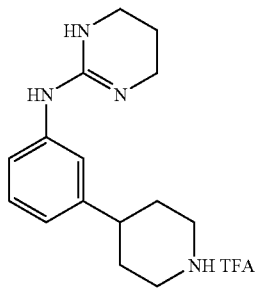

To a solution of the compound of Reference Example 27 (600 mg) in dichloromethane (10 ml) is added trifluoroacetic acid (10 ml), and the mixture is stirred at 25° C. overnight. The reaction solution is concentrated under reduced pressure to give the title compound.

REFERENCE EXAMPLE 29

Preparation of 1-(2-amino-6-methylpyrimidin-4-yl)piperidine-4-carboxylic acid ethyl ester:

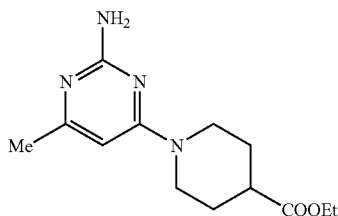

A solution of 4-piperidinecarboxylic acid ethyl ester (6.6 g), 2-amino-4-chloro-6-methylpyrimidine (5.0 g) and triethylamine (4.2 g) in ethanol (50 ml) is stirred at 90° C. for 3 hours. Ethanol is evaporated under reduced pressure, and the residue is dissolved in chloroform, and washed with water. The organic layer is concentrated under reduced pressure to give the title compound.

REFERENCE EXAMPLE 30

Preparation of 1-(2-amino-6-methylpyrimidin-4-yl)piperidine-4-carboxylic acid:

To a solution of the compound of Reference Example 29 in methanol (30 ml) is added 2M aqueous sodium hydroxide solution (28 ml), and the mixture is stirred at 70° C. for one hour. Methanol is evaporated under reduced pressure, and the aqueous layer is acidified with conc. hydrochloric acid. The resulting precipitates are collected by filtration to give the title compound (3.0 g).

REFERENCE EXAMPLE 31

Preparation of (2S)-3-[[1-(2-amino-6-methylpyrimidin-4-yl)piperidin-4-yl]carbonylamino]-2-(benzyloxycarbonylamino)propanoic acid methyl ester:

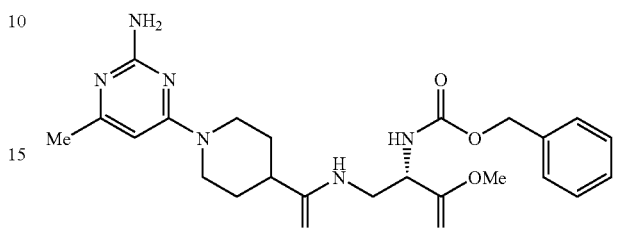

To a solution of the compound of Reference Example 30 (1.0 g) in dimethylformamide (200 ml) are added successively (2S)-3-amino-2-(benzyloxycarbonylamino)propanoic acid methyl ester hydrochloride (1.2 g), benzotriazol-1-yloxytris(pyrrolidino)phosphonium hexafluoro-phosphate (2.2 g) and ethyldiisopropylamine (2.1 g), and the mixture is stirred at 25° C. overnight. The reaction solution is poured into water, and the mixture is extracted with chloroform. The organic layer is concentrated under reduced pressure, and the residue is purified by silica gel column chromatography (eluent: gradient, 0% to 100% ethyl acetate/hexane) to give the title compound.

REFERENCE EXAMPLE 32

Preparation of (2S)-2-benzyloxycarbonylamino-3-[[1-[2-[1,3-bis(tert-butoxycarbonyl) hexahydropyrimidin-2-ylidene]-6-methylpyrimidin-4-yl]piperidin-4-yl]carbonylamino]propanoic acid methyl ester:

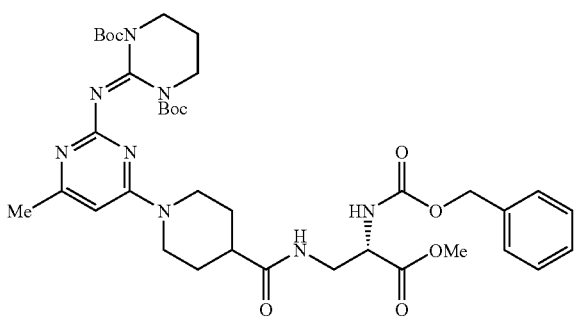

To a solution of the compound of Reference Example 31 (1.2 g) and 1,3-bis(tert-butoxycarbonyl)-2(1H)-hexahydropyrimidinethione (1.66 g) in dimethylformamide (10 ml) are added triethylamine (1.1 ml) and mercury (II) chloride (2.11 g), and the mixture is stirred at 25° C. overnight. The reaction solution is filtered, and the solvent is evaporated under reduced pressure. The residue is purified by silica gel column chromatography (eluent: gradient, 0% to 100% ethyl acetate/hexane) to give the title compound (2.0 g).

REFERENCE EXAMPLE 33

Preparation of 4-(3-nitrophenyl)-3-cyclohexenecarboxylic acid ethyl ester:

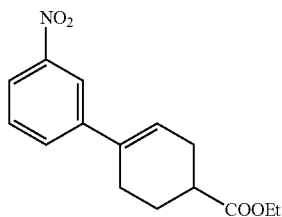

(1) To a solution of 4-oxocyclohexanecarboxylic acid ethyl ester (8.0 g) and 2,6-di(tert-butyl)-4-methylpyridine (14.4 g) in dichloromethane (200 ml) is added trifluoromethanesulfonic anhydride (8.73 ml) at −78° C., and the mixture is gradually warmed to 25° C., and the mixture is stirred at the same temperature overnight. The reaction solution is poured into aqueous sodium hydrogen carbonate solution, and the mixture is extracted with ethyl acetate. The organic layer is washed with saturated brine, and the solvent is evaporated under reduced pressure to give 4-trifluoromethanesulfonyloxy-3-cyclohexenecarboxylic acid ethyl ester.

(2) To a mixture of the above trifluoromethanesulfonyloxy compound and 3-nitrophenylboronic acid (10.0 g), lithium chloride (6.4 g) in ethylene glycol dimethyl ether (160 ml) and 2 M sodium carbonate (60.0 ml) is added tetrakistriphenylphosphine palladium (0) (2.88 g), and the mixture is stirred at 90° C. under argon atmosphere for 3 hours. The reaction solution is poured into ice, and the mixture is extracted with ethyl acetate. The organic layer is washed with saturated brine, and the solvent is evaporated under reduced pressure. The residue is purified by silica gel column chromatography (eluent: gradient, 0% to 100% ethyl acetate/hexane) to give the title compound (10.0 g).

REFERENCE EXAMPLE 34

Preparation of 4-(3-aminophenyl)cyclohexanecarboxylic acid ethyl ester:

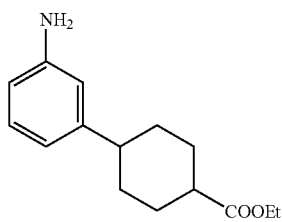

To a solution of the compound of Reference Example 33 (10.0 g) in ethanol (300 ml) is added 10% palladium on carbon (wet, 10.0 g), and the mixture is stirred at 25° C. for 6 hours under hydrogen atmosphere. The catalyst is removed by filtration, and the filtrate is concentrated under reduced pressure. The residue is purified by silica gel column chromatography (eluent: gradient, 0% to 100% ethyl acetate/hexane) to give the title compound (5.8 g).

REFERENCE EXAMPLE 35

Preparation of 4-[3-[1,3-bis(tert-butoxycarbonyl)hexahydropyrimidin-2-ylidene]aminophenyl]cyclohexanecarboxylic acid ethyl ester:

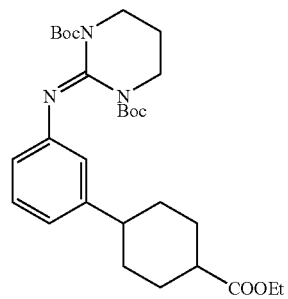

To a solution of the compound of Reference Example 34 and 1,3-bis(tert-butoxycarbonyl)-2(1H)-tetrahydropyrimidinethione (11.18 g) in dimethylformamide (50 ml) are added triethylamine (9.84 ml), and mercury (II) chloride (9.59 g), and the mixture is stirred at 25° C. overnight. The reaction solution is filtered, and the filtrate is evaporated under reduced pressure. The residue is purified by silica gel column chromatography (eluent: gradient, 0% to 100% ethyl acetate/hexane) to give the title compound.

REFERENCE EXAMPLE 36

Preparation of 4-[3-[1,3-bis(tert-butoxycarbonyl)hexahydropyrimidin-2-ylidene]aminophenyl]cyclohexanecarboxylic acid:

The compound of Reference Example 35 is dissolved in a mixture of methanol (100 ml) and tetrahydrofuran (200 ml), and thereto is added 2 M aqueous sodium hydroxide solution (100 ml), and the mixture is stirred at 25° C. for one day. Methanol and tetrahydrofuran are evaporated under reduced pressure, and the aqueous layer is washed with toluene, and acidified with 10% aqueous citric acid solution. The aqueous layer was extracted with ethyl acetate, and the organic layer is washed with saturated brine. The solvent is evaporated under reduced pressure to give the title compound.

REFERENCE EXAMPLE 37

Preparation of (2S)-2-benzyloxycarbonylamino-3-[[4-[3-[1,3-bis (tert-butoxycarbonyl)hexahydropyrimidin-2-ylidene]aminophenyl]-cyclohexane]carbonylamino]propanoic acid methyl ester:

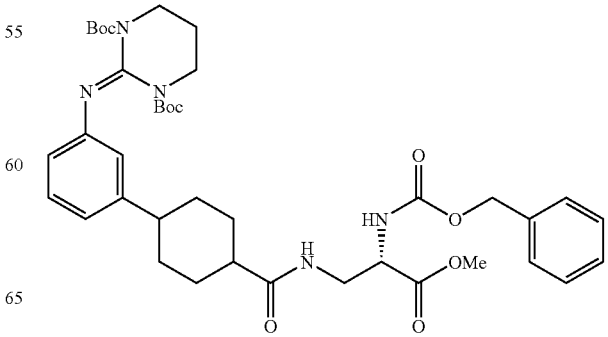

To a solution of the compound of Reference Example 36 in dimethylformamide (100 ml) are added successively (2S)-3-amino-2-(benzyloxycarbonylamino)propanoic acid methyl ester hydrochloride (2.38 g), 1-hydroxybenzotriazole (1.26 g), ethyldiisopropylamine (6.3 ml) and 1-ethyl-3-(3-dimethylaminopropyl)carbodiimide hydrochloride (3.38 g), and the mixture is stirred at 25° C. overnight. The reaction solution is diluted with ethyl acetate, and washed successively with 10% aqueous citric acid solution, saturated aqueous sodium hydrogen carbonate solution and saturated brine, and dried over magnesium sulfate. The solvent is evaporated under reduced pressure to give the title compound (500 mg).

REFERENCE EXAMPLE 38

Preparation of 1-(2-methoxyphenyl)piperidine-4-carboxylic acid ethyl ester:

To a solution of 4-piperidinecarboxylic acid ethyl ester (5.0 g) and 2-methoxyphenylboronic acid (5.0 g) in dichloromethane (100 ml) are added pyridine (12.9 ml), anhydrous copper (II) acetate (5.78 g) and Molecular sieves 4 Å (100 g), and the mixture is stirred at 25° C. for 2 days. The reaction solution is filtered, and the filtrate is poured into 10% aqueous citric acid solution, and the organic layer is washed successively with aqueous sodium hydrogen carbonate solution, and saturated brine. The solvent is evaporated under reduced pressure, and the residue is purified by silica gel column chromatography (eluent: gradient, 0% to 100% hexane/ethyl acetate) to give the title compound.

REFERENCE EXAMPLE 39

Preparation of 1-(2-methoxy-5-nitrophenyl)piperidine-4-carboxylic acid:

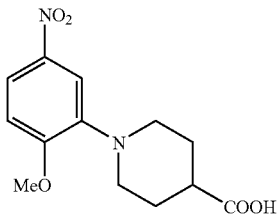

To a solution of the compound of Reference Example 38 in conc. sulfuric acid (20 ml) is added conc. nitric acid (0.52 ml) at 0° C., and the mixture is stirred at around 10° C. for 2 hours. The reaction solution is poured into cold water, and the pH value of the solution is adjusted to pH 3 with 2M aqueous sodium hydroxide solution. The aqueous layer is extracted with ethyl acetate, and the organic layer is washed with saturated brine. The solvent is evaporated under reduced pressure, and the residue is purified by silica gel column chromatography (eluent: gradient, 0% to 100% hexane/ethyl acetate) to give 1-(2-methoxy-5-nitrophenyl)piperidine-4-carboxylic acid ethyl ester (1.0 g).

To a solution of this ester compound in methanol (10 ml) is added 2M aqueous sodium hydroxide solution (10 ml), and the mixture is stirred at 25° C. overnight. The reaction solution is concentrated, and diluted with water and ethyl acetate. The aqueous layer is acidified with conc. hydrochloric acid, and the resulting precipitates are collected by filtration to give the title compound (0.70 g).

REFERENCE EXAMPLE 40

Preparation of 1-(2-methoxy-5-nitrophenyl)piperazine hydrochloride:

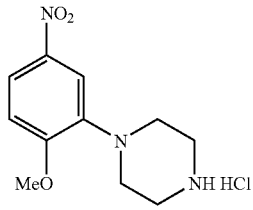

(1) To a solution of 1-(2-methoxyphenyl)piperazine (30 g) in dichloromethane (500 ml) are added triethylamine (22.9 ml) and ethyl chloroformate (15.8 ml), and the mixture is stirred at 25° C. overnight. The reaction solution is concentrated under reduced pressure, diluted with ethyl acetate, washed successively with 10% aqueous citric acid solution and saturated brine, and dried over magnesium sulfate. The solvent is evaporated under reduced pressure to give ethyl 4-(2-methoxyphenyl)piperazine-1-carboxylate.

(2) To a solution of the above product (5 g) in conc. sulfuric acid (18 ml) is added conc. nitric acid (1.31 ml) at 0° C., and the mixture is stirred at around 10° C. for 2 hours. The reaction solution is poured into cold water, and the pH value thereof is adjusted to pH 3 with 2M aqueous sodium hydroxide solution. The resulting precipitates are collected by filtration to give ethyl 4-(2-methoxy-5-nitrophenyl)piperazine-1-carboxylate.

(3) The above product (5 g) is dissolved in a mixture of methanol (50 ml) and tetrahydrofuran (50 ml), and thereto is added 2M aqueous sodium hydroxide solution (50 ml), and the mixture is heated under reflux for 18 hours. The reaction solution is diluted with water and ethyl acetate, and the organic layer is washed with saturated brine, dried over magnesium sulfate. To the organic layer is added a 30% solution of hydrogen chloride in ethanol, and the resulting precipitates are collected by filtration to give the title compound (3.52 g).

REFERENCE EXAMPLE 41

Preparation of 1-(2-fluoro-5-nitrophenyl)piperazine hydrochloride:

The title compound is prepared in a similar manner to Reference Example 40 except that 1-(2-fluorophenyl)piperazine is used instead of 1-(2-methoxyphenyl)piperazine in Reference Example 40.

REFERENCE EXAMPLE 42

Preparation of 2-(4-ethoxycarbonyl-1-piperidinyl)-4-nitropyridine N-oxide:

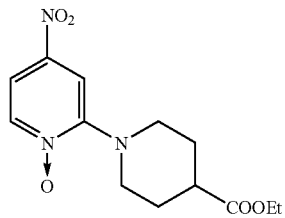

To a solution of 2-bromo-4-nitropyridine N-oxide (12 g), which is prepared according to the method disclosed in J. Org. Chem., 21, 1077 (1956), in ethanol (300 ml) are added 4-piperidinecarboxylic acid ethyl ester (22 g) and triethylamine (11.6 ml), and the mixture is stirred at 80° C. for 5 hours. The reaction solution is concentrated under reduced pressure, and the residue is dissolved in ethyl acetate, washed with water, and the solvent is evaporated under reduced pressure to give the title compound (18 g).

REFERENCE EXAMPLE 43

Preparation of 1-(4-amino 2-pyridyl)piperidine-4-carboxylic acid:

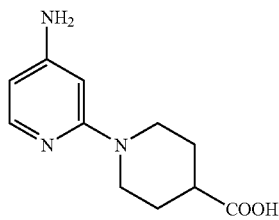

The compound of Reference Example 42 (10 g) is added to a solution of titanium (0) (500 ml) (prepared from magnesium (20 g) and titanium chloride (40 ml)) in tetrahydrofuran at 0° C. Fifteen minutes thereafter, to the reaction solution is added saturated aqueous sodium hydrogen carbonate solution, and the resulting precipitates are collected by filtration. The filtrate is diluted with ethyl acetate, and the organic layer is washed successively with saturated aqueous sodium hydrogen carbonate solution, and saturated brine, and dried over sodium sulfate. The solvent is evaporated under reduced pressure, and the residue is purified by silica gel column chromatography (eluent: gradient, 0% to 25% methanol/chloroform) to give 1-(4-amino-2-pyridyl)piperidine-4-carboxylic acid ethyl ester (5 g).

To a solution of this product (5 g) in methanol (100 ml) is added 2M aqueous sodium hydroxide solution (100 ml), and the mixture is stirred at 25° C. overnight. The reaction solution is neutralized with 2M hydrochloric acid, and the solvent is evaporated under reduced pressure to give the title compound.

EXAMPLE 1

Preparation of (2S)-2-benzyloxycarbonylamino-3-[[1-[3-(1,4,5,6-tetrahydropyrimidin-2-yl) aminophenyl]piperidin-4-yl]carbonylamino]-propanoic acid methyl ester:

To a solution of the compound of Reference Example 5 (10 g) in dichloromethane (100 ml) is added trifluoroacetic acid (100 ml), and the mixture is stirred at 25° C. overnight. The solvent is evaporated under reduced pressure to give the title compound.

EXAMPLE 2

Preparation of (2S)-2-benzyloxycarbonylamino-3-[[1-[3-(1,4,5,6-tetrahydropyrimidin-2-yl)aminophenyl]piperidin-4-yl]carbonylamino]propanoic acid:

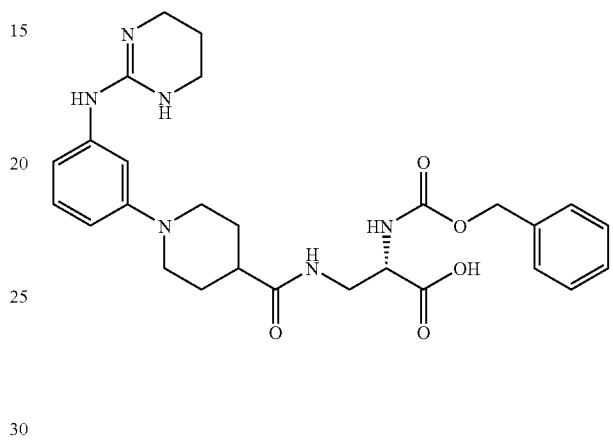

To a solution of the product obtained in Example 1 in methanol (100 ml) is added 2M aqueous sodium hydroxide solution (100 ml), and the mixture is stirred at 25° C. overnight. The reaction solution is neutralized with trifluoroacetic acid, and purified by CHP-20 (manufactured by Mitsubishi Chemical Corporation, highporous styrene resin: 75–150 μm) (eluent: gradient, 30% to 100% methanol/ 0.05% aqueous trifluoroacetic acid solution) to give the title compound (6.5 g).

$^1$H-NMR (300 MHz, CD$_3$OD, δ): 1.84 (4H, m), 1.98 (2H, m), 2.39 (1H, m), 2.91 (2H, m), 3.37 (4H, t), 3.45 (1H, m), 3.71 (3H, m), 4.39 (1H, dd), 5.08 (2H, dd), 6.78 (1H, dd), 6.91 (1H, dd), 7.02 (1H, dd), 7.34 (6H, m). HPLC, Rt: 9.04 min.

EXAMPLES 3 TO 14

Instead of 1,3-bis (tert-butoxycarbonyl)-2(1H)-tetrahydropyrimidinethione in Reference Example 5, 1,3-Bis (tert-butoxycarbonyl)-2-thione compound is treated in a similar manner to Reference Example 5 to give a condensed product, which is treated with trifluoroacetic acid in a similar manner to Example 1 to give (2S)-2-benzyloxycarbonylamino-3-[[1-(3-cyclic guanidinophenyl)piperidin-4-yl]carbonylamino]-propanoic acid methyl ester (Examples 3 to 8).

Further, the compounds of Examples 3 to 8 thus obtained are treated in a similar manner to Example 2 to give (2S)-2-benzyloxycarbonylamino-3-[[1-(3-cyclic guanidinophenyl)piperidin-4-yl]carbonylamino]propanoic acids as listed in Table 3 (Examples 9 to 14).

TABLE 3

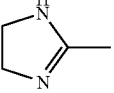

| | U | R⁷ | HPLC; Rt (min) |
|---|---|---|---|
| Example 3 | 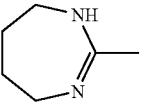 | Me | — |
| Example 9 | | H | 8.81 |
| Example 4 | 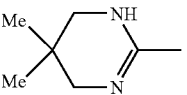 | Me | — |
| Example 10 | | H | 9.51 |
| Example 5 | 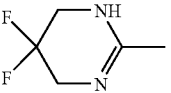 | Me | — |
| Example 11 | | H | 10.4 |
| Example 6 | 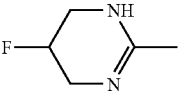 | Me | — |
| Example 12 | | H | 9.74 |
| Example 7 | 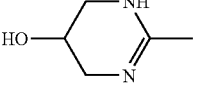 | Me | — |
| Example 13 | | H | 8.97 |
| Example 8 | | Me | — |
| Example 14 | | H | 8.38 |

EXAMPLES 15 TO 20

(2S)-2-Isobutoxycarbonylamino-3-[[1-(3-nitrophenyl)piperidin-4-yl]carbonylamino]propanoic acid methyl ester is prepared in a similar manner to Reference Example 3 except that (2S)-3-amino-2-(isobutoxycarbonylamino)propanoic acid methyl ester p-toluenesulfonate is used instead of (2S)-3-amino-2-(benzyloxycarbonylamino)propanoic acid methyl ester hydrochloride in Reference Example 3.

Then, this product is reduced in a similar manner to Reference Example 4 to give (2S)-3-[[1-(3-aminophenyl)piperidin-4-yl]carbonylamino]-2-(isobutoxycarbonylamino) propanoic acid methyl ester. This product and a corresponding 1,3-bis(tert-butoxycarbonyl)-2-thione compound are treated in a similar manner to Reference Example 5, and the resulting product is treated in a similar manner to Example 1 to give a (2S)-3-[[1-(3-cyclic guanidinophenyl)piperidin-4-yl]carbonylamino]-2-(isobutoxycarbonylamino)propanoic acid methyl ester (Examples 15 to 17).

The compounds of Examples 15 to 17 thus obtained are treated in a similar manner to Example 2 to give (2S)-3-[[1-(3-cyclic guanidinophenyl)piperidin-4-yl]carbonylamino]-2-(isobutoxycarbonylamino) propanoic acids as listed in Table 4 (Examples 18 to 20).

TABLE 4

| | U | R⁷ | HPLC; Rt (min) |
|---|---|---|---|
| Example 15 | (4,4-dimethyl-tetrahydropyrimidin-2-yl) | Me | — |
| Example 18 | | H | 9.64 |
| Example 16 | (5-fluoro-tetrahydropyrimidin-2-yl) | Me | — |
| Example 19 | | H | 8.09 |
| Example 17 | (5-hydroxy-tetrahydropyrimidin-2-yl) | Me | — |
| Example 20 | | H | 7.36 |

EXAMPLE 21

Preparation of (2S)-3-[[1-[3-(benzylaminothiocarbonyl) aminophenyl]-piperidin-4-yl]carbonylamino]-2-(benzyloxycarbonylamino)propanoic acid methyl ester:

To a solution of the compound of Reference Example 4 (200 mg) in dichloromethane (2 ml) are added ethyldiisopropylamine (0.15 ml) and benzylisothiocyanate (0.13 g), and the mixture is stirred at 25° C. overnight. The reaction solution is concentrated under reduced pressure, and the residue is purified by silica gel column chromatography (eluent: gradient, 0% to 5% methanol/chloroform) to give the title compound.

EXAMPLE 22

Preparation of (2S)-3-[[1-[3-(benzylaminothiocarbonyl) aminophenyl]-piperidin-4-yl]carbonylamino]-2-(benzyloxycarbonylamino)propanoic acid:

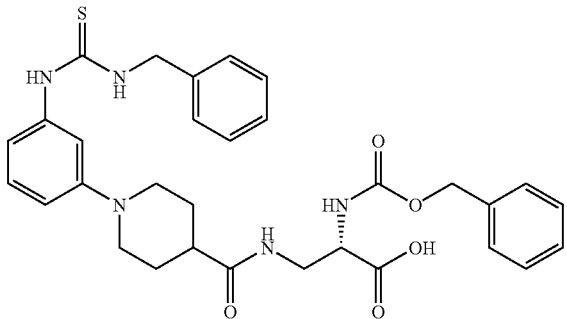

To a solution of the compound of Example 21 in methanol (2 ml) is added 2M aqueous sodium hydroxide solution (2 ml), and the mixture is stirred at 25° C. overnight. The reaction solution is neutralized with trifluoroacetic acid, and purified by CHP-20 (eluent: gradient, 35% to 100% methanol/0.05% aqueous trifluoroacetic acid solution) to give the title compound (40 mg).

¹H-NMR (300 MHz, CD₃OD, δ); 2.03 (4H, m), 2.56 (1H, m), 3.43 (3H, m), 3.71 (3H, m), 4.43 (1H, dd), 4.82 (2H, s), 5.09 (2H, dd), 7.38 (13H, m), 7.98 (1H, s). HPLC, Rt: 13.41 min.

EXAMPLES 23 TO 28

Instead of benzylisothiocyanate in Example 21, suitable isocyanates are treated in a similar manner to Example 21 to give (2S)-2-benzyloxycarbonylamino-3-[[1-(3-substituted ureidophenyl)piperidin-4-yl]carbonylamino]propanoic acid methyl esters (Examples 23 to 25).

The compounds of Examples 23 to 25 thus obtained are treated in a similar manner to Example 22 to give (2S)-2-benzyloxycarbonylamino-3-[[1-(3-substituted ureidophenyl)piperidin-4-yl]carbonylamino]-propanoic acids as listed in Table 5 (Examples 26 to 28).

TABLE 5

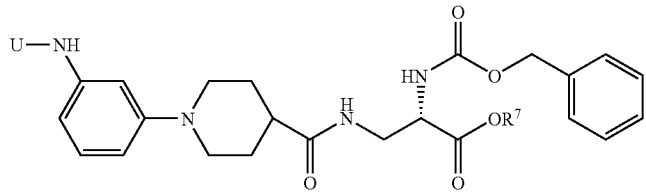

| | U | R[7] | HPLC; Rt (min) |
|---|---|---|---|
| Example 23 | PhNHCO— | Me | — |
| Example 26 | | H | 12.55 |
| Example 24 | 3-PyNHCO— | Me | — |
| Example 27 | | H | 8.55 |
| Example 25 | i-PrNHCO— | Me | — |
| Example 28 | | H | 11.06 |

EXAMPLE 29

Preparation of (2S)-3-[[1-[3-(benzylaminocarbonyl)aminophenyl]-piperidin-4-yl]carbonylamino]-2-(benzyloxycarbonylamino)propanoic acid methyl ester:

To a solution of the compound of Reference Example 7 (200 mg) in dimethylformamide (2 ml) are added successively (2S)-3-amino-2-(benzyloxycarbonylamino)propanoic acid methyl ester hydrochloride (400 mg), 1-hydroxybenzotriazole (108 mg), ethyldiisopropylamine (0.617 ml) and 1-ethyl-3-(3-dimethylaminopropyl)carbodiimide hydrochloride (404 mg), and the mixture is stirred at 25° C. overnight. The reaction solution is diluted with ethyl acetate, washed successively with 10% aqueous citric acid solution, saturated aqueous sodium hydrogen carbonate solution and saturated brine, and dried over magnesium sulfate. The solvent is evaporated under reduced pressure, and the residue is purified by silica gel column chromatography (eluent: gradient, 0% to 15% methanol/chloroform) to give the title compound.

EXAMPLE 30

Preparation of (2S)-3-{[1-[3-(benzylaminocarbonyl)aminophenyl]-piperidin-4-yl}carbonylamino]-2-(benzyloxycarbonylamino)propanoic acid:

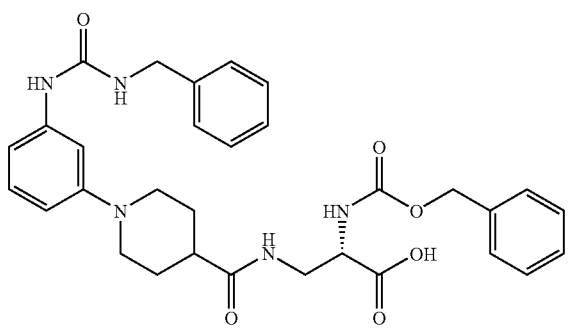

To a solution of the compound of Example 29 in methanol (10 ml) is added 2M aqueous sodium hydroxide solution (10 ml), and the mixture is stirred at 25° C. overnight. The reaction solution is neutralized with trifluoroacetic acid, purified by CHP-20 (eluent: gradient, 35% to 100% methanol/0.05% aqueous trifluoroacetic acid solution) to give the title compound.

$^1$H-NMR (300 MHz, $CD_3OD$, δ); 1.92 (4H, m), 2.44 (1H, m), 3.09 (2H, m), 3.46 (1H, m), 3.66 (3H, m), 4.39 (3H, m), 5.07 (2H, dd), 6.88 (1H, dd), 7.02 (1H, dd), 7.32 (1H, m), 7.57 (1H, s). HPLC, Rt: 12.54 min.

EXAMPLES 31 to 42

Instead of (2S)-3-amino-2-(benzyloxycarbonylamino) propanoic acid methyl ester hydrochloride in Example 29, suitable 3-aminopropanoic acid methyl ester derivatives are treated in a similar manner to Example 29 to give 3-[[1-[3-(benzylaminocarbonyl)aminophenyl]-piperidin-4-yl]carbonylamino]propanoic acid methyl ester compounds (Examples 31 to 36).

The compounds of Examples 31 to 36 thus obtained are treated in a similar manner to Example 30 to give 3-[[1-[3-(benzylaminocarbonyl)aminophenyl]piperidin-4-yl]carbonylamino]propanoic acid compounds as listed in Table 6 (Examples 37 to 42).

TABLE 6

[Structure: benzyl-NH-C(O)-NH-phenyl-N(piperidine)-C(O)-NH-CH(R⁵)-CH(R⁶)-COOR⁷]

| | R⁵ | R⁶ | R⁷ | HPLC; Rt (min) |
|---|---|---|---|---|
| Example 31 | 3-Py | H | Me | — |
| Example 37 | | | H | 8.43 |
| Example 32 | Ph | H | Me | — |
| Example 38 | | | H | 11.85 |
| Example 33 | 3,5-Cl₂Ph | H | Me | — |
| Example 39 | | | H | 14.05 |
| Example 34 | Me | H | Me | — |
| Example 40 | | | H | 9.86 |
| Example 35 | H | i-PrOCONH— | Me | — |
| Example 41 | | | H | 11.03 |
| Example 36 | H | 2,4,6-Me₃PhSO₂NH— | Me | — |
| Example 42 | | | H | 13.41 |

EXAMPLE 43

Preparation of (2S)-2-isopropoxycarbonylamino-3-[[1-[3-(1,4,5,6-tetrahydropyrimidin-2-yl) aminophenyl] piperidin-4-yl] carbonylamino]-propanoic acid methyl ester:

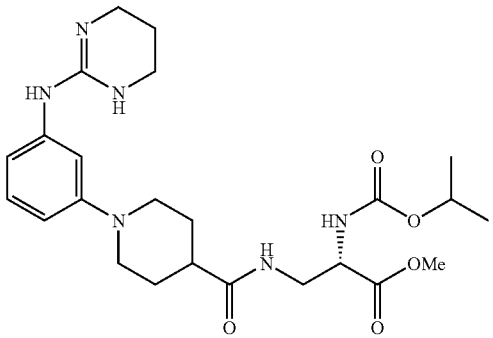

To a solution of the compound of Reference Example 10 in dichloromethane (5 ml) is added trifluoroacetic acid (5 ml), and the mixture is stirred at 25° C. overnight. The reaction solution is concentrated under reduced pressure to give the title compound.

EXAMPLE 44

Preparation of (2S)-2-isopropoxycarbonylamino-3-[[1-[3-(1,4,5,6-tetrahydropyrimidin-2-yl)aminophenyl]piperidin-4-yl]carbonylamino]-propanoic acid:

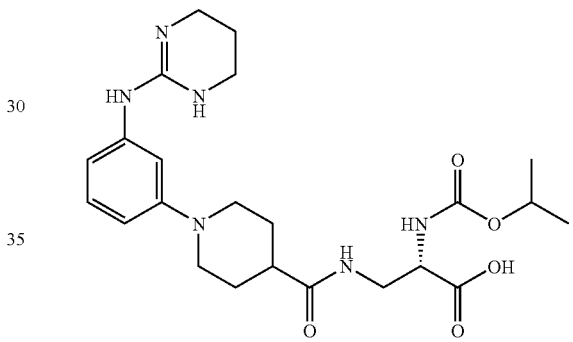

To a solution of the compound of Example 43 in methanol (5 ml) is added 2M aqueous sodium hydroxide solution (5 ml), and the mixture is stirred at 25° C. overnight. The reaction solution is neutralized with trifluoroacetic acid, and purified by CHP-20 (eluent: gradient, 35% to 100% methanol/0.05% aqueous trifluoroacetic acid solution) to give the title compound (40 mg).

¹H-NMR (300 MHz, CD₃OD, δ); 1.20 (3H, d), 1.22 (3H, d), 1.99 (6H, m), 2.42 (1H, m), 2.92 (2H, m), 3.36 (4H, t), 3.45 (1H, dd), 3.65 (1H, dd), 3.77 (2H, m), 4.33 (1H, dd), 6.77 (1H, d), 6.90 (1H, s), 7.01 (1H, dd), 7.33 (1H, t). HPLC, Rt: 6.98 min.

EXAMPLES 45 TO 50

Instead of (2S)-3-amino-2-(isopropoxycarbonylamino) propanoic acid methyl ester hydrochloride in Reference Example 10, suitable 3-aminopropanoic acid methyl ester derivatives are treated in a similar manner to Reference Example 10, and the products thus obtained are treated in a similar manner to Example 43 to give 3-[[1-(3-cyclic guanidinophenyl) piperidin-4-yl]carbonylamino]propanoic acid methyl esters (Examples 45 to 47).

The compounds of Examples 45 to 47 thus obtained are treated in a similar manner to Example 44 to give 3-[[1-(3-cyclic guanidinophenyl)piperidin-4-yl]carbonylamino]propanoic acids as listed in Table 7 (Examples 48 to 50).

TABLE 7

| | R⁵ | R⁶ | R⁷ | HPLC; Rt (min) |
|---|---|---|---|---|
| Example 45 | 3-Py | H | Me | — |
| Example 48 | | | H | 7.84 |
| Example 46 | 3,5-Cl₂Ph | H | Me | — |
| Example 49 | | | H | 11.36 |
| Example 47 | H | 2,4,6-Me₃PhSO₂NH— | Me | — |
| Example 50 | | | H | 10.36 |

EXAMPLES 51 to 120

Instead of ethyl chloroformate in Reference Example 12, suitable chloroformic acid ester derivatives or acylating agents are treated in a similar manner to Reference Example 12 to give 2-substituted aminopropanoic acid methyl ester compounds. These products and the product of Reference Example 12 are treated in a similar manner to Example 1 to give (2S)-2-substituted amino-3-[[1-[3-(1,4,5,6-tetrahydro-pyrimidin-2-yl)aminophenyl]piperidin-4-yl]carbonylamino] propanoic acid methyl esters (Examples 51 to 85).

The compounds of Examples 51 to 85 thus obtained are treated in a similar manner to Example 2 to give (2S)-2-substituted amino-3-[[1-[3-(1,4,5,6-tetrahydropyrimidin-2-yl)aminophenyl]piperidin-4-yl]-carbonylamino]propanoic acids as listed in Table 8 (Examples 86 to 120).

TABLE 8

| | R⁶ | R⁷ | HPLC; Rt (min) |
|---|---|---|---|
| Example 51 | CH₃CH₂OCONH— | Me | — |
| Example 86 | | H | 5.49 |
| Example 52 | CH₃(CH₂)₃OCONH— | Me | — |
| Example 87 | | H | 8.69 |
| Example 53 | CH₃(CH₂)₅OCONH— | Me | — |
| Example 88 | | H | 11.07 |
| Example 54 | CH₃(CH₂)₇OCONH— | Me | — |
| Example 89 | | H | 13.13 |
| Example 55 | CH₃(CH₂)₉OCONH— | Me | — |
| Example 90 | | H | 15.39 |
| Example 56 | CH₃(CH₂)₁₅OCONH— | Me | — |
| Example 91 | | H | 21.01 |
| Example 57 | (CH₃)₂CHCH₂OCONH— | Me | — |
| Example 92 | | H | 8.18 |
| Example 58 | (CH₃)₃CCH₂OCONH— | Me | — |
| Example 93 | | H | 9.26 |
| Example 59 | CH₃OCH₂CH₂OCONH— | Me | — |
| Example 94 | | H | 5.44 |
| Example 60 | (−)-3-p-menthyl-OCONH— | Me | — |
| Example 95 | | H | 13.07 |
| Example 61 | CH₂=CHCH₂OCONH— | Me | — |
| Example 96 | | H | 5.27 |
| Example 62 | CH₃(CH₂)₄CONH— | Me | — |
| Example 97 | | H | 8.46 |
| Example 63 | (CH₃)₂CHCH₂CONH— | Me | — |
| Example 98 | | H | 6.85 |
| Example 64 | (CH₃)₂C=CHCONH— | Me | — |
| Example 99 | | H | 6.70 |
| Example 65 | PhCH=CHCONH— | Me | — |
| Example 100 | | H | 9.03 |
| Example 66 | PhCH₂CONH— | Me | — |
| Example 101 | | H | 7.74 |

TABLE 8-continued

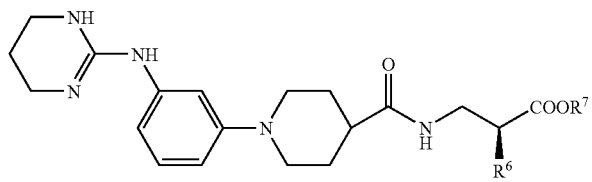

| | R⁶ | R⁷ | HPLC; Rt (min) |
|---|---|---|---|
| Example 67 | PhCH₂CH₂CONH— | Me | — |
| Example 102 | | H | 8.77 |
| Example 68 | cyclo-C₅H₉CONH— | Me | — |
| Example 103 | | H | 7.28 |
| Example 69 | PhCONH— | Me | — |
| Example 104 | | H | 7.41 |
| Example 70 | 2-PyCONH— | Me | — |
| Example 105 | | H | 9.25 |
| Example 71 | Ph—Ph—CONH— | Me | — |
| Example 106 | | H | 11.39 |
| Example 72 | CH₃CH₂CH₂SO₂NH— | Me | — |
| Example 107 | | H | 6.07 |
| Example 73 | CH₃(CH₂)₇SO₂NH— | Me | — |
| Example 108 | | H | 12.44 |
| Example 74 | PhCH₂SO₂NH— | Me | — |
| Example 109 | | H | 8.17 |
| Example 75 | (+)-2-oxobornan-10-yl- | Me | — |
| Example 110 | SO₂NH— | H | 9.00 |
| Example 76 | (−)-2-oxobornan-10-yl- | Me | — |
| Example 111 | SO₂NH— | H | 8.64 |
| Example 77 | PhSO₂NH— | Me | — |
| Example 112 | | H | 7.56 |
| Example 78 | 4-F—PhSO₂NH— | Me | — |
| Example 113 | | H | 8.20 |
| Example 79 | 4-MeO—PhSO₂NH— | Me | — |
| Example 114 | | H | 8.26 |
| Example 80 | 2-Naph-SO₂NH— | Me | — |
| Example 115 | | H | 10.1 |
| Example 81 | 3,5-Me₂-4-Isoxz-SO₂NH— | Me | — |
| Example 116 | | H | 7.74 |
| Example 82 | CH₃(CH₂)₅NHCONH— | Me | — |
| Example 117 | | H | 10.43 |
| Example 83 | (CH₃)₂CHNHCONH— | Me | — |
| Example 118 | | H | 5.79 |
| Example 84 | PhCH₂NHCONH— | Me | — |
| Example 119 | | H | 7.78 |
| Example 85 | 3-PyNHCONH— | Me | — |
| Example 120 | | H | 7.86 |

EXAMPLE 121

Preparation of (2S)-2-benzyloxycarbonylamino-5-[4-[3-(1,4,5,6-tetrahydropyrimidin-2-yl)aminophenyl]piperazin-1-yl]-5-oxopentanoic acid:

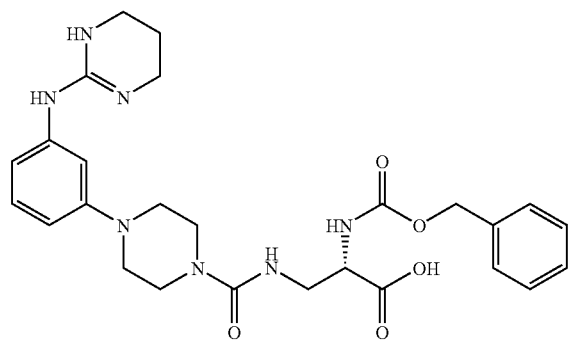

To a solution of the compound of Reference Example 16 (130 mg) in dichloromethane (10 ml) is added trifluoroacetic acid (10 ml), and the mixture is stirred at 25° C. overnight. The solvent is evaporated under reduced pressure, and the residue is purified by CHP-20 (eluent: gradient, 35% to 100% methanol/0.05% aqueous trifluoroacetic acid solution) to give the title compound (80 mg).

¹H-NMR (300 MHz, CD₃OD, δ): 1.95 (3H, m), 2.25 (1H, m), 2.53 (2H, m), 3.18 (4H, m), 3.35 (4H, t), 3.62 (2H, t), 3.72 (2H, m), 4.23 (1H, dd), 5.07 (2H, dd), 6.71 (1H, dd), 6.79 (1H, t), 6.93 (1H, dd), 7.32 (6H, m). HPLC, Rt: 10.86 min.

EXAMPLES 122 TO 125

Instead of 1,3-bis (tert-butoxycarbonyl)-2(1H)-tetrahydropyrimidinethione in Reference Example 16, 1,3-bis (tert-butoxycarbonyl)-2-thione compound is treated in a similar manner to Reference Example 16 to give the condensed product. The product thus obtained is treated in a similar manner to Example 121 to give (2S)-2-benzyloxycarbonylamino-5-[4-(3-cyclic guanidinophenyl)piperazine-1-yl]-5-oxopentanoic acids as listed in Table 9.

TABLE 9

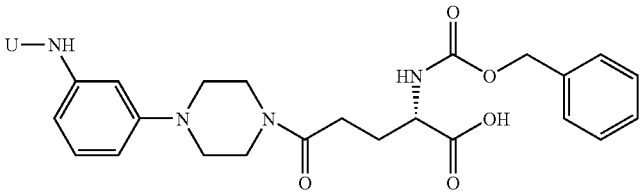

| U | HPLC; Rt (min) |
|---|---|
| Example 122 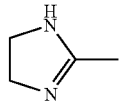 | 10.63 |
| Example 123 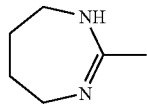 | 11.43 |
| Example 124 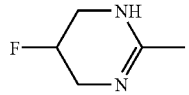 | 10.73 |
| Example 125 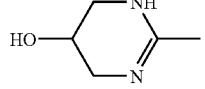 | 9.99 |

EXAMPLES 126 TO 135

(2S)-2-Alkyloxycarbonylamino-5-[4-(3-nitrophenyl)piperazin-1-yl]-5-oxopentanotic acid tert-butyl ester is prepared in a similar manner to Reference Example 14 except that N-alkyloxycarbonyl-L-glutamic acid tert-butyl ester is used instead of N-benzyloxycarbonyl-L-glutamic acid α-tert-butyl ester in Reference Example 14. This product is treated in a similar manner to Reference Example 15 to give 3-aminophenyl compounds, which are further treated together with a suitable 1,3-bis(tert-butoxycarbonyl)-2(1H)-tetrahydropyrimidinethione compound in a similar manner to Reference Example 16 to give a corresponding 3-[1,3-bis(tert-butoxycarbonyl)hexahydropyrimidin-2-ylidene]amino-phenylpiperazine compound.

This compound is treated in a similar manner to Example 121 to give (2S)-2-alkyloxycarbonylamino-5-[4-(3-cyclic guanidinophenyl)piperazin-1-yl]-5-oxopentanoic acids as listed in Table 10.

TABLE 10

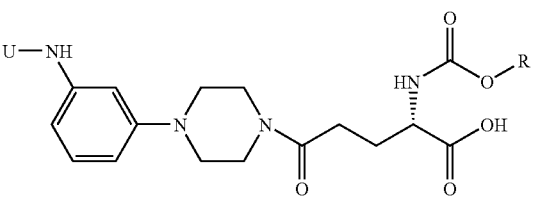

| | U | R | HPLC; Rt (min) |
|---|---|---|---|
| Example 126 | 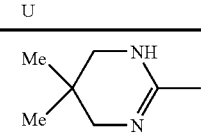 | iso-Bu | 11.43 |
| Example 129 | | $C_6H_{13}$ | 13.61 |
| Example 132 | | $C_{10}H_{21}$ | 17.18 |
| Example 127 | 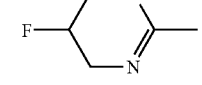 | iso-Bu | 10.11 |
| Example 130 | | $C_6H_{13}$ | 12.45 |
| Example 133 | | $C_{10}H_{21}$ | 16.20 |
| Example 128 | 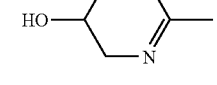 | iso-Bu | 9.23 |
| Example 131 | | $C_6H_{13}$ | 11.78 |
| Example 134 | | $C_{10}H_{21}$ | 15.54 |
| Example 135 | 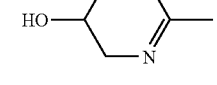 | $C_{10}H_{21}$ | 16.30 |

EXAMPLES 136 TO 143

Instead of the compound of Reference Example 11 and ethyl chloroformate in Reference Example 12, the compound of Reference Example 17 and suitable chloroformic acid ester derivatives or an acylating agent are treated in a similar manner to Reference Example 12 to give 2-substituted amino-5-oxopentanoic acid tert-butyl ester compounds, which are treated in a similar manner to Example 121 to give the compounds as listed in Table 11.

TABLE 11

[Structure]

| | $R^6$ | HPLC; Rt (min) |
|---|---|---|
| Example 136 | $CH_3CH_2OCONH-$ | 8.25 |
| Example 137 | $CH_3(CH_2)_5OCONH-$ | 12.43 |
| Example 138 | $(CH_3)_2CHCH_2OCONH-$ | 10.24 |
| Example 139 | $PhCH_2CONH-$ | 9.74 |
| Example 140 | $2,4,6-Me_3PhSO_2NH-$ | 11.88 |
| Example 141 | $PhSO_2NH-$ | 9.48 |
| Example 142 | $CH_3CH_2NHCONH-$ | 7.27 |
| Example 143 | $PhCH_2NHCONH-$ | 9.65 |

EXAMPLE 144

Preparation of (2S)-2-benzyloxycarbonylamino-3-[[4-[3-(1,4,5,6-tetrahydropyrimidin-2-yl)aminophenyl]piperazin-1-yl]carbonylamino]-propanoic acid methyl ester:

To a solution of the compound of Reference Example 20 (25 mg) in dichloromethane (5 ml) is added trifluoroacetic acid (5 ml), and the mixture is stirred at 25° C. overnight. The solvent is evaporated under reduced pressure to give the title compound.

EXAMPLE 145

Preparation of (2S)-2-benzyloxycarbonylamino-3-[[4-[3-(1,4,5,6-tetrahydropyrimidin-2-yl)aminophenyl]piperazin-1-yl]carbonylamino]-propanoic acid:

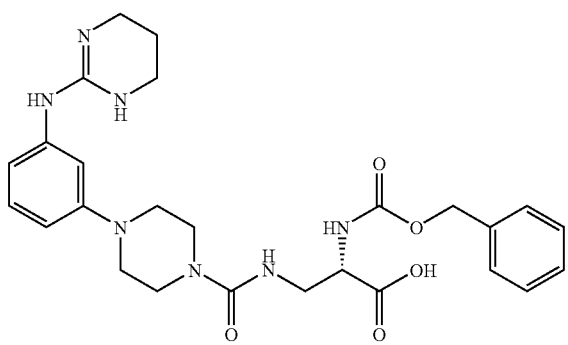

To a solution of the compound of Example 144 in methanol (5 ml) is added 2M aqueous sodium hydroxide solution (5 ml), and the mixture is stirred at 25° C. overnight. The reaction solution is neutralized with trifluoroacetic acid, and purified by CHP-20 (eluent: gradient, 35% to 100% methanol/0.05% aqueous trifluoroacetic acid solution) to give the title compound (8 mg).

$^1$H-NMR (300 MHz, CD$_3$OD, δ): 1.97 (2H, m), 3.15 (4H, t), 3.36 (4H, t), 3.48 (5H, m), 3.66 (1H, dd), 4.35 (1H, dd), 5.06 (2H, dd), 6.69 (1H, dd), 6.77 (1H, t), 6.91 (1H, dd), 7.30 (6H, m). HPLC, Rt: 10.52 min.

EXAMPLE 146

Preparation of (2S)-2-benzyloxycarbonylamino-4-[[1-[3-(1,4,5,6-tetrahydropyrimidin-2-yl)aminophenyl]piperidin-4-yl]amino]-4-oxobutanoic acid:

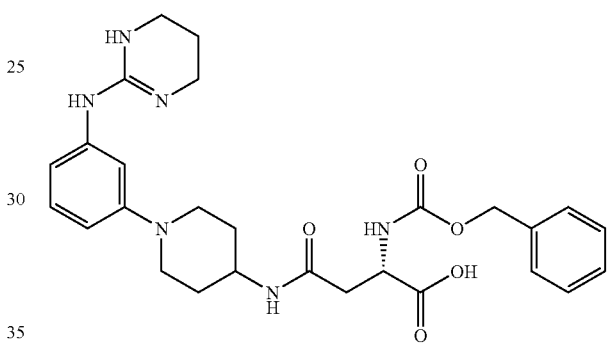

To a solution of the compound of Reference Example 25 (600 mg) in dichloromethane (10 ml) is added trifluoroacetic acid (10 ml), and the mixture is stirred at 25° C. overnight. The solvent is evaporated under reduced pressure, and the residue is purified by CHP-20 (eluent: gradient, 35% to 100% methanol/0.05% aqueous trifluoroacetic acid solution) to give the title compound (220 mg).

$^1$H-NMR (300 MHz, CD$_3$OD, δ): 1.76 (2H, m), 1.98 (4H, m), 2.73 (2H, m), 3.23 (2H, m), 3.38 (4H, m), 3.68 (2H, m), 3.91 (1H, m), 4.59 (2H, m), 5.09 (1H, dd), 7.02 (1H, dd), 7.30 (8H, m). HPLC, Rt: 9.34 min.

EXAMPLE 147

Preparation of (2S)-2-benzyloxycarbonylamino-5-[4-[3-(1,4,5,6-tetrahydropyrimidin-2-yl)aminophenyl]piperidin-1-yl]-5-oxopentanoic acid tert-butyl ester:

To a solution of N-benzyloxycarbonyl-L-glutamic acid α-tert-butyl ester (434 mg) and ethyldiisopropylamine (0.936 ml) in tetrahydrofuran (20 ml) is added pivaloyl chloride (0.146 ml) at 0° C., and the mixture is stirred at 0° C. for 30 minutes. To the reaction solution is added a solution of the compound of Reference Example 28 in tetrahydrofuran (20 ml), and the mixture is stirred at 25° C. overnight, and the solvent is evaporated under reduced pressure to give the title compound.

EXAMPLE 148

Preparation of (2S)-2-benzyloxycarbonylamino-5-[4-[3-(1,4,5,6-tetrahydropyrimidin-2-yl)aminophenyl]piperidin-1-yl]-5-oxopentanoic acid:

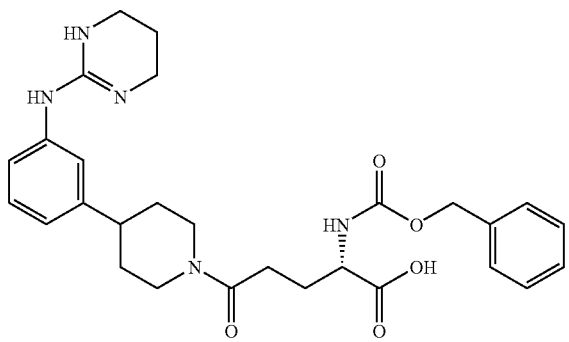

To a solution of the compound of Example 147 in dichloromethane (10 ml) is added trifluoroacetic acid (10 ml), and the mixture is stirred at 25° C. overnight. The solvent is evaporated under reduced pressure, and the residue is purified by CHP-20 (eluent: gradient, 35% to 100% methanol/0.05% aqueous trifluoroacetic acid solution) to give the title compound (200 mg).

$^1$H-NMR (300 MHz, CD$_3$OD, δ): 1.59 (2H, m), 1.93 (5H, m), 2.38–2.82 (4H, m), 3.16 (1H, dd), 3.38 (4H, dd), 3.99 (1H, d), 4.22 (1H, m), 4.65 (1H, d), 5.07 (2H, d), 7.21 (10H, m). HPLC, Rt: 11.49 min.

EXAMPLE 149

Preparation of (2S)-2-benzyloxycarbonylamino-3-[[1 1-[2-(1,4,5,6-tetrahydropyrimidin-2-yl)amino-6-methylpyrimidin-4-yl]piperidin-4-yl]-carbonylamino]propanoic acid methyl ester:

To a solution of the compound of Reference Example 32 (240 mg) in dichloromethane (2 ml) is added trifluoroacetic acid (2 ml), and the mixture is stirred at 25° C. for 4 hours. The solvent is evaporated under reduced pressure to give the title compound.

EXAMPLE 150

Preparation of (2S)-2-benzyloxycarbonylamino-3-[[1-[2-(1,4,5,6-tetrahydropyrimidin-2-yl) amino-6-methylpyrimidin-4-yl] piperidin-4-yl]-carbonylamino]propanoic acid:

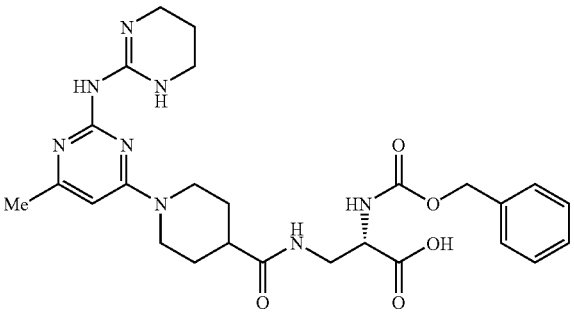

To a solution of the compound of Example 149 in methanol (4 ml) is added 2M aqueous sodium hydroxide solution (4 ml), and the mixture is stirred at 25° C. overnight. The reaction solution is concentrated under reduced pressure, and the residue is purified by CHP-20 (eluent: gradient, 35% to 100% methanol/0.05% aqueous trifluoroacetic acid solution) to give the title compound (50 mg).

$^1$H-NMR (300 MHz, CD$_3$OD, δ): 1.58 (2H, dd), 1.78 (2H, m), 2.02 (2H, m), 2.29 (3H, s), 2.49 (1H, m), 2.97 (2H, dd), 3.49 (5H, m), 3.66 (1H, m), 4.35 (3H, m), 5.06 (2H, dd), 6.37 (1H, s), 7.32 (5H, m). HPLC, Rt: 10.81 mm.

EXAMPLE 151

Preparation of (2S)-2-benzyloxycarbonylamino-3-[[4-[3-(1,4,5,6-tetrahydrofuranhydropyrimidin-2-yl) aminophenyl] cyclohexane] carbonylamino]propanoic acid:

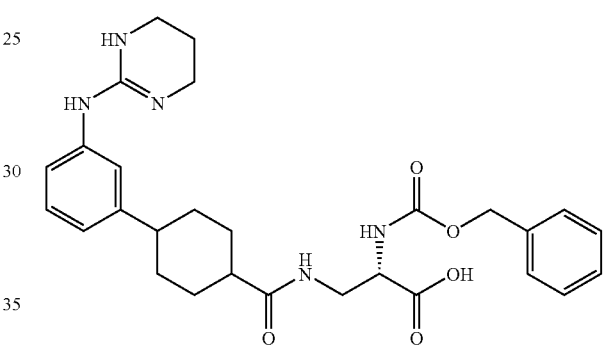

To a solution of the compound of Reference Example 37 (500 mg) in dichloromethane (10 ml) is added trifluoroacetic acid (10 ml), and the mixture is stirred at 25° C. for 3 hours. The solvent is evaporated under reduced pressure to give (2S)-2-benzyloxycarbonylamino-3-[[4-[3-(1,4,5,6-tetrahydropyrimidin-2-yl)aminophenyl]cyclohexane]carbonylamino]propanoic acid methyl ester.

To a solution of this ester compound in methanol (5 ml) is added 2M aqueous sodium hydroxide solution (5 ml), and the mixture is stirred at 25° C. overnight. The reaction solution is neutralized with trifluoroacetic acid, and purified by CHP-20 (eluent: gradient, 30% to 100% methanol/0.05% aqueous trifluoroacetic acid solution) to give Stereoisomer A (30 mg) and Stereoisomer B (30 mg) of the title compound.

Stereoisomer A; $^1$H-NMR (300 MHz, CD$_3$OD, δ): 1.55 (4H, m), 1.98 (6H, m), 2.22 (1H, m), 2.54 (1H, m), 3.37 (4H, t), 3.47 (1H, m), 3.64 (1H, dd), 4.36 (1H, dd), 5.10 (2H, dd), 7.05 (2H, m), 7.19 (1H, dd), 7.34 (6H, m).

HPLC, Rt: 11.70 min.

Stereoisomer B; $^1$H-NMR (300 MHz, CD$_3$OD, δ): 1.67 (4H, m), 1.98 (6H, m), 2.52 (1H, m), 2.63 (1H, m), 3.32 (4H, t), 3.43 (1H, m), 3.71 (1H, dd), 4.41 (1H, dd), 5.00 (2H, s), 7.02 (1H, m), 7.12 (1H, m), 7.20 (1H, m), 7.30 (6H, m). HPLC, Rt: 12.20 min.

EXAMPLE 152

Preparation of (2S)-2-benzyloxycarbonylamino-3-[[1-[2-methoxy-5-(1,4,5,6-tetrahydropyrimidin-2-yl)aminophenyl]piperidin-4-yl]carbonylamino]propanoic acid:

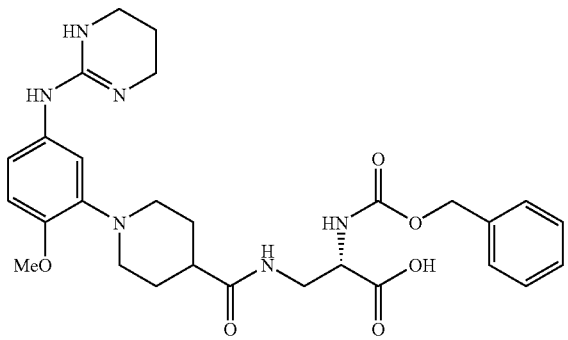

The compound of Reference Example 39 is treated in a similar manner to Reference Example 3 to give (2S)-2-(benzyloxycarbonylamino)-3-[[1-(2-methoxy-5-nitrophenyl)piperidin-4-yl]carbonylamino]-propanoic acid methyl ester. This product is further treated in a similar manner to Reference Examples 4 and 5 to give (2S)-2-benzyloxycarbonylamino-3-[[1-[5-[1,3-bis(tert-butoxycarbonyl)hexahydropyrimidin-2-ylidene]amino-2-methoxyphenyl]piperidin-4-yl]carbonylamino]propanoic acid methyl ester.

This product is treated in a similar manner to Example 1 to give (2S)-2-benzyloxycarbonylamino-3-[[1-[2-methoxy-5-(1,4,5,6-tetrahydropyrimidin-2-yl)aminophenyl]piperidin-4-yl]carbonylamino]propanoic acid methyl ester, which is further treated in a similar manner to Example 2 to give the title compound. HPLC, Rt: 8.57 min.

EXAMPLE 153

Preparation of (2S)-2-benzyloxycarbonylamino-3-[[1-[4-methyl-3-(1,4,5,6-tetrahydropyrimidin-2-yl)aminophenyl]piperidin-4-yl]-carbonylamino]propanoic acid:

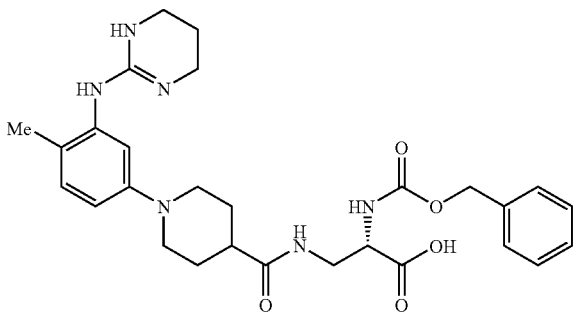

4-Methyl-3-nitrophenylboronic acid is treated in a similar manner to Reference Examples 1 to 5 to give (2S)-3-[[1-[3-[1,3-bis(tert-butoxycarbonyl)hexahydropyrimidin-2-ylidene]amino-4-methylphenyl]-piperidin-4-yl]carbonylamino]-2 (benzyloxycarbonylamino)propanoic acid methyl ester.

This product is treated in a similar manner to Example 1 to give (2S)-2-benzyloxycarbonylamino-3-[1-[[4-methyl-3-(1,4,5,6-tetrahydropyrimidin-2-yl)aminophenyl]piperidin-4-yl]carbonylamino]propanoic acid methyl ester, which is further treated in a similar manner to Example 2 to give the title compound. HPLC, Rt: 8.92 min.

EXAMPLES 154 TO 155

The compound of Reference Example 40 or 41 is treated in a similar manner to Reference Examples 14 to 16, and the resulting product is further treated in a similar manner to Example 121 to give the following compounds.

Example 154 $R^b$=OMe (HPLC Rt: 10.68 min.)
Example 155 $R^b$=F (HPLC Rt: 11.41 min.)

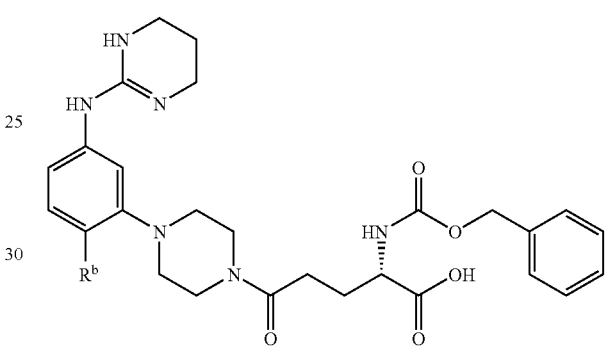

EXAMPLES 156 to 157

3,5-Difluoronitrobenzene or 3-fluoro-4-methylnitrobenzene is treated in a similar manner to Reference Example 13 to give 1-(5-fluoro-3-nitrophenyl)piperazine hydrochloride or 1-(2-methyl-5-nitrophenyl)piperazine hydrochloride.

This product is treated in a similar manner to Reference Examples 14 to 16, and the resulting product is treated in a similar manner to Example 121 to give the following compounds.

Example 155 $R^{b'}$=H, $R^{b''}$=F (Rt: 11.14 min.)
Example 156 $R^{b'}$=Me, $R^{b''}$=H (Rt: 10.20 min.)

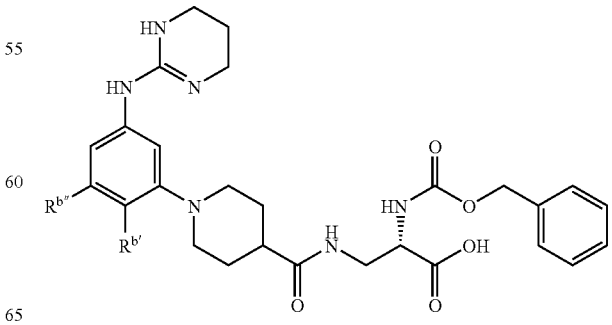

EXAMPLE 158

Preparation of (2S)-2-benzyloxycarbonylamino-5-[4-[5-fluoro-3-(1,4,5,6-tetrahydropyrimidin-2-yl)aminophenyl]piperazin-1-yl]-5-oxopentanoic acid:

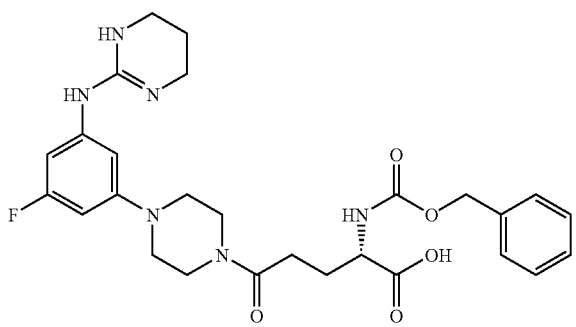

3,5-Difluoronitrobenzene is treated in a similar manner to Reference Examples 13 to 16, and the resulting product is treated in a similar manner to Example 121 to give the title compound. HPLC, Rt: 11.51 min.

EXAMPLES 159 TO 161

The compound of Reference Example 43 is treated in a similar manner to Reference Example 3 to give (2S)-3-[[1-(4-amino-2-pyridyl)piperidin-4-yl]carbonylamino]-2-(benzyloxycarbonylamino or isobutoxycarbonylamino)propanoic acid methyl ester. This product and a corresponding 1,3-bis(tert-butoxycarbonyl)-2(1H)-tetrahydropyrimidinethione compound are treated in a similar manner to Reference Example 5 to give a corresponding (2S)-2-(benzyloxycarbonylamino or isobutoxycarbonylamino)-3-[[1-[4-[1,3-bis(tert-butoxycarbonyl)hexahydropyrimidin-2-ylidene]amino-2-pyridyl]piperidin-4-yl]-carbonylamino]propanoic acid methyl ester.

This product thus obtained is treated in a similar manner to Examples 1 and 2 to give the compounds as listed in Table 12.

TABLE 12

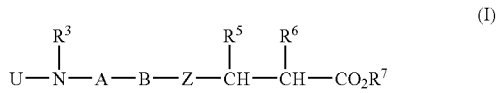

| | $R^a$ | R | HPLC; Rt (min) |
|---|---|---|---|
| Example 159 | H | CH$_2$Ph | 7.68 |
| Example 160 | F | CH$_2$Ph | 7.59 |
| Example 161 | H | CH$_2$CHMe$_2$ | 6.94 |

EXAMPLE 162

Preparation of (2S)-2-benzyloxycarbonylamino-3-[[1-[3-(1,4,5,6-tetrahydropyrimidin-2-yl)aminophenyl]piperidin-4-yl]-N-methylcarbonylamino]propanoic acid:

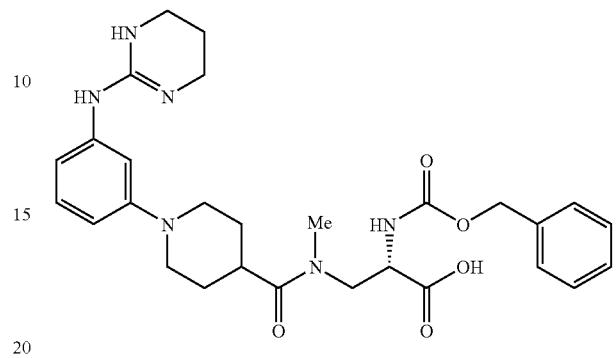

Instead of (2S)-3-amino-2-(benzyloxycarbonylamino)propanoic acid methyl ester hydrochloride in Reference Example 3, (2S)-3-methylamino-2-(benzyloxycarbonylamino)propanoic acid methyl ester is treated in a similar manner to Reference Example 3 to give (2S)-2-benzyloxycarbonylamino-3-[[1-(3-nitrophenyl)piperidin-4-yl]-N-methylcarbonylamino]propanoic acid methyl ester. This product thus obtained is treated in a similar manner to Reference Examples 4 to 5 and Examples 1 to 2 to give the title compound. HPLC, Rt: 9.36 min.

INDUSTRIAL APPLICABILITY

As mentioned above, the compound (I) of the present invention, a prodrug thereof, a pharmaceutical acceptable salt thereof or an N-oxide derivative thereof, or a hydrate or solvate thereof has a high selectivity for αvβ3 integrin and exhibits a potent inhibitory activity thereto with low toxicity, and hence, it can be used as a preventive and/or therapeutic agent for a disease in which αvβ3 integrin is involved, such as antirestenotic agents, antiarteriosclerotic agents, anticancer agents, anti-osteoporosis agents, antiinflammatory agents, antiimmune agents, and therapeutic agents for eye diseases.

What is claimed is:

1. An aryl-substituted alicyclic compound of the following formula (I), or a pharmaceutically acceptable salt thereof, or an N-oxide thereof, or a hydrate thereof.

$$U-N(R^3)-A-B-Z-CH(R^5)-CH(R^6)-CO_2R^7 \quad (I)$$

wherein U is the following formula:

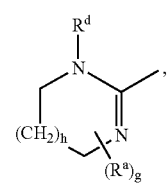

A is a group of the following formula:

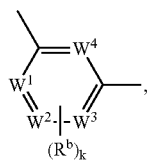

B is a group of the following formula:

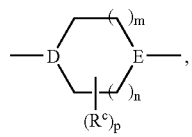

Z is —CONR$^4$(CH$_2$)$_q$—, —NR$^4$CO(CH$_2$)$_q$— or —COCH$_2$(CH$_2$)$_q$—,

W$^1$, W$^2$, W$^3$ and W$^4$ are the same or different, and each is —CH— or a nitrogen atom, D and E are the same or different, and each is —CH— or a nitrogen atom, R$^a$ is the same or different, and each is a hydrogen atom, a halogen atom, a hydroxy group, a C$_{1-6}$ alkyl group, a C$_{3-7}$ cycloalkyl group, a C$_{2-6}$ alkenyl group, a C$_{2-6}$ alkynyl group, an aryl group, an aralkyl group, a C$_{1-6}$ alkyloxy group, a C$_{1-6}$ alkyloxycarbonyl group, a formyl group, a C$_{1-6}$ alkylcarbonyl group, a carboxyl group, a C$_{1-6}$ alkylcarbonyloxy group, an amino group, a C$_{1-3}$ alkylamino group, a di(C$_{1-3}$ alkyl)amino group, a formylamino group, a C$_{1-3}$ alkylcarbonylamino group, an arylcarbonylamino group, a nitro group, a cyano group, a trifluoromethyl group, a trifluoromethoxy group or a trifluoroethoxy group, or when two R$^a$ groups attach to the same carbon atom, then they combine to form an oxo group or a thioxo group, or together with said carbon atom to form a spiro ring, R$^b$ is the same or different, and each is a hydrogen atom, a halogen atom, a hydroxy group, a C$_{1-6}$ alkyl group, a C$_{3-7}$ cycloalkyl group, a C$_{2-6}$ alkenyl group, a C$_{2-6}$ alkynyl group, an aryl group, an aralkyl group, a C$_{1-6}$ alkyloxy group, a C$_{1-6}$ alkyloxycarbonyl group, a formyl group, a C$_{1-6}$ alkylcarbonyl group, a carboxyl group, a C$_{1-6}$ alkylcarbonyloxy group, an amino group, a C$_{1-3}$ alkylamino group, a di(C$_{1-3}$ alkyl)amino group, a formylamino group, a C$_{1-3}$ alkylcarbonylamino group, an arylcarbonylamino group, a nitro group, a cyano group, a trifluoromethyl group, a trifluoromethoxy group or a trifluoroethoxy group, R$^c$ is the same or different, and each is a hydrogen atom, a halogen atom, a hydroxy group, a C$_{1-6}$ alkyl group, a C$_{3-7}$ cycloalkyl group, a C$_{2-6}$ alkenyl group, a C$_{2-6}$ alkynyl group, an aryl group, an aralkyl group, a C$_{1-6}$ alkyloxy group, a C$_{1-6}$ alkyloxycarbonyl group, a formyl group, a C$_{1-6}$ alkylcarbonyl group, a carboxyl group, a C$_{1-6}$ alkylcarbonyloxy group, an amino group, a C$_{1-3}$ alkylamino group, a di(C$_{1-3}$ alkyl)amino group, a formylamino group, a C$_{1-3}$ alkylcarbonylamino group, an arylcarbonylamino group, a nitro group, a cyano group, a trifluoromethyl group, a trifluoromethoxy group or a trifluoroethoxy group, or two R$^c$ groups may combine to form —(CR$^8$R$^9$)$_t$—, R$^d$ is a hydrogen atom, a C$_{1-6}$ alkyl group, a C$_{3-7}$ cycloalkyl group, a C$_{2-6}$ alkenyl group, a C$_{2-6}$ alkynyl group, an aryl group, an aralkyl group, a formyl group, a C$_{1-6}$ alkylcarbonyl group or a C$_{1-6}$ alkyloxycarbonyl group, R$^3$ and R$^4$ are the same or different, and each is a hydrogen atom, a C$_{1-6}$ alkyl group, a C$_{3-7}$ cycloalkyl group, a C$_{2-6}$ alkenyl group, a C$_{2-6}$ alkynyl group, an aryl group or an aralkyl group, R$^5$ is a hydrogen atom, a halogen atom, a C$_{1-6}$ alkyl group, a C$_{3-7}$ cycloalkyl group, a C$_{2-6}$ alkenyl group, a C$_{2-6}$ alkynyl group, an aryl group or an aralkyl group, R$^6$ is a hydrogen atom, a halogen atom, a hydroxy group, a C$_{1-6}$ alkyl group, a C$_{3-7}$ cycloalkyl group, a C$_{2-6}$ alkenyl group, a C$_{2-6}$ alkynyl group, an aryl group, an aralkyl group, a C$_{1-6}$ alkyloxy group, a C$_{3-7}$ cycloalkyloxy group, a C$_{2-6}$ alkenyloxy group, a C$_{2-6}$ alkynyloxy group, an aryloxy group, an aralkyloxy group, a C$_{1-6}$ alkylcarbonyloxy group, a C$_{3-7}$ cycloalkylcarbonyloxy group, a C$_{2-6}$ alkenylcarbonyloxy group, a C$_{2-6}$ alkynylcarbonyloxy group, an arylcarbonyloxy group, an aralkylcarbonyloxy group, an amino group or a mono-substituted amino group (in which the substituent thereof is a formyl, a C$_{1-10}$ alkylcarbonyl, a C$_{3-7}$ cycloalkylcarbonyl, a C$_{2-10}$ alkenylcarbonyl, a C$_{2-10}$ alkynylcarbonyl, an arylcarbonyl, an aralkylcarbonyl, a C$_{7-15}$ polycyclo-C$_{0-3}$ alkylcarbonyl, a C$_{1-16}$ alkyloxycarbonyl, a polyfluoro-C$_{1-16}$ alkyloxycarbonyl, a C$_{3-7}$ cycloalkyloxycarbonyl, a C$_{2-16}$ alkenyloxycarbonyl, a C$_{2-16}$ alkynyloxycarbonyl, an aryloxycarbonyl, a C$_{3-7}$ cycloalkyl-C$_{1-6}$ alkyloxycarbonyl, an aralkyloxycarbonyl, a C$_{1-10}$ alkylaminocarbonyl, a C$_{3-7}$ cycloalkylaminocarbonyl, a C$_{2-10}$ alkenylaminocarbonyl, a C$_{2-10}$ alkynylaminocarbonyl, an arylaminocarbonyl, an aralkylaminocarbonyl, a C$_{1-10}$ alkylsulfonyl, a C$_{3-7}$ cycloalkylsulfonyl, a C$_{2-10}$ alkenylsulfonyl, a C$_{2-10}$ alkynylsulfonyl, an arylsulfonyl, an aralkylsulfonyl, a C$_{7-15}$ polycyclo-C$_{0-3}$ alkylsulfonyl, a C$_{1-10}$ alkylaminosulfonyl, a C$_{3-7}$ cycloalkylaminosulfonyl, a C$_{2-10}$ alkenylaminosulfonyl, a C$_{2-10}$ alkynylaminosulfonyl, an arylaminosulfonyl or an aralkylaminosulfonyl), R$^7$ is a hydrogen atom, a C$_{1-6}$ alkyl group, a C$_{3-7}$ cycloalkyl group, an aryl group or an aralkyl group, R$^8$ and R$^9$ are the same or different, and each is a hydrogen atom, a C$_{1-3}$ alkyl group or an aryl group, g is an integer of 1 to 4, h is an integer of 0 to 3, k is an integer of 1 to 3, m and n are the same or different, and each is an integer of 0 to 3, but the sum of m and n should be an integer of 1 to 3, p is an integer of 1 to 4, q is 0 or 1, t is an integer of 1 to 3, provided that (i) when E is a nitrogen atom, then Z is —CONR$^4$(CH$_2$)$_q$ or COCH$_2$(CH$_2$)$_q$—, (ii) in the above definition, the alkyl group, the cycloalkyl group, the alkenyl group, the alkynyl group, and the alkyl moiety of the aralkyl group may optionally be substituted by 1 to 3 atoms or groups selected from a halogen, a C$_{1-6}$ alkyloxy, an amino and a hydroxy, and the aryl group and the aryl moiety may optionally be substituted by 1 to 5 atoms or groups selected from a halogen, a C$_{1-6}$ alkyl, a C$_{3-7}$ cycloalkyl, an aryl, an aralkyl, an amino, an amino-C$_{1-6}$ alkyl, a formylamino, a C$_{1-3}$ alkylcarbonylamino, a C$_{1-6}$ alkylamino, a C$_{1-6}$ alkylamino-C$_{1-6}$ alkyl, a di(C$_{1-6}$ alkyl)amino, a di(C$_{1-6}$ alkyl)amino-C$_{1-6}$ alkyl, an arylcarbonylamino, a $C_{1-6}$ alkylaminocarbonylamino, an arylaminocarbonylamino, a $C_{1-4}$ alkyloxy, a $C_{1-4}$ alkylthio, a $C_{1-4}$ alkylsulfonyl, a $C_{1-4}$ alkyloxy-$C_{1-6}$ alkyl, a carboxyl, a carboxyl-$C_{1-6}$ alkyl, a $C_{1-4}$ alkyloxycarbonyl, a hydroxy, a hydroxy-$C_{1-6}$ alkyl, a cyano, a trifluoromethyl, a trifluoromethoxy, a $C_{1-4}$ alkylcarbonyloxy and a nitro.

2. The aryl-substituted alicyclic compound according to claim 1, wherein U is the following formula:

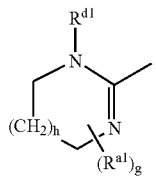

$R^{a1}$ is the same or different, and each is a hydrogen atom, a halogen atom, a hydroxy group, a $C_{1-6}$ alkyl group, a $C_{3-7}$ cycloalkyl group, an aryl group, an aralkyl group, a $C_{1-6}$ alkyloxy group, a $C_{1-6}$ alkoxycarbonyl group, a carboxyl group, a $C_{1-6}$ alkylcarbonyloxy group, an amino group, a di($C_{1-3}$ alkyl)amino group, a $C_{1-3}$ alkylcarbonylamino group, a nitro group, a cyano group, a trifluoromethyl group, a trifluoromethoxy group or a trifluoroethoxy group, or when two $R^{a1}$ groups attach to the same carbon atom, then they combine to form an oxo group or a thioxo group, or together with said carbon atom to form a spiro ring, $R^{d1}$ is a hydrogen atom, a $C_{1-3}$ alkyl group, a $C_{1-3}$ alkylcarbonyl group or a $C_{1-6}$ alkyloxycarbonyl group, and g and h are as defined in claim 1), A is a group selected from the following formulae:

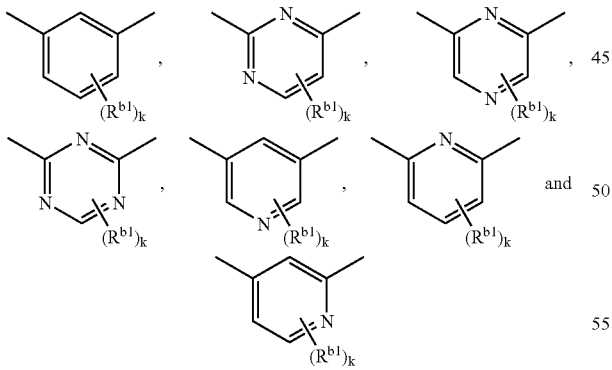

($R^{b1}$ is the same or different, and each is a hydrogen atom, a halogen atom, a hydroxy group, a $C_{1-3}$ alkyl group, an aryl group, a $C_{1-3}$ alkyloxy group, a $C_{1-3}$ alkyloxycarbonyl group, a carboxyl group, a $C_{1-3}$ alkylcarbonyloxy group, an amino group, a di($C_{1-3}$ alkyl)amino group, a $C_{1-3}$ alkylcarbonylamino group, a nitro group, a cyano group, a trifluoromethyl group or a trifluoromethoxy group, k is as defined in claim 1), B is a group selected from the following formulae:

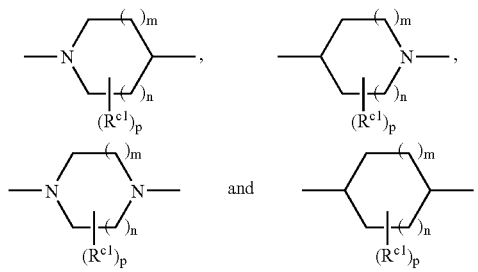

($R^{c1}$ is the same or different, and each is a hydrogen atom, a halogen atom, a hydroxy group, a $C_{1-6}$ alkyl group, a $C_{3-7}$ cycloalkyl group, an aryl group, an aralkyl group, a $C_{1-6}$ alkyloxy group, a $C_{1-6}$ alkyloxycarbonyl group, a formyl group, a carboxyl group, a $C_{1-6}$ alkylcarbonyloxy group, an amino group, a di($C_{1-3}$ alkyl)amino group, a $C_{1-3}$ alkylcarbonylamino group, a cyano group or a trifluoromethyl group, or two $R^{c1}$ groups may combine to form —$(CH_2)_t$—, m, n, p and t are as defined in claim 1), $R^3$ is a hydrogen atom, $R^4$ is a hydrogen atom or a $C_{1-3}$ alkyl group, or a pharmaceutically acceptable salt thereof or an N-oxide thereof, or a hydrate thereof.

3. The aryl-substituted alicyclic compound according to claim 2, wherein U is the following formulae:

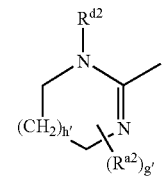

$R^{a2}$ is the same or different, and each is a hydrogen atom, a fluorine atom, a hydroxy group, a $C_{1-4}$ alkyl group, an aryl group, a $C_{1-3}$ alkyloxy group, a $C_{1-3}$ alkyloxycarbonyl group, a di($C_{1-3}$ alkyl)amino group, a $C_{1-3}$ alkylcarbonylamino group, a hydroxy-$C_{1-3}$ alkyl group, a carboxyl group, a $C_{1-3}$ alkylcarbonyloxy group, a trifluoromethyl group or a trifluoromethoxy group, $R^{d2}$ is a hydrogen atom, a methyl group, an acetyl group, a propionyl group, a methoxycarbonyl group, an ethoxycarbonyl group or a tert-butoxycarbonyl group, g' is 1 or 2, h' is an integer of 0 to 2), B is a group selected from the following formulae:

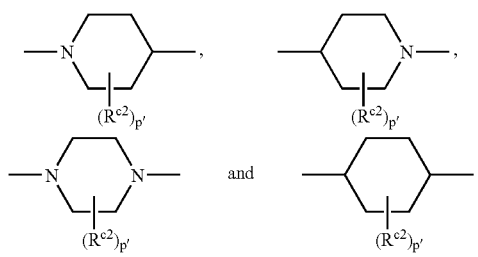

($R^{c2}$ is the same or different, and each is a hydrogen atom, a methyl group, a phenyl group, a $C_{1-2}$ alkyloxycarbonyl group or a carboxyl group, or two $R^{c2}$ groups may combine to form —$(CH_2)_t$—, p' is 1 or 2, t is an integer of 1 to 3), Z is —$CONR^{4'}$—, —$NR^{4'}CO$— or —$COCH_2$—, $R^{4'}$ is a hydrogen atom or a methyl group, $R^6$ is a mono-substituted amino group (the substituent thereof is a formyl, a $C_{1-10}$ alkylcarbonyl, a $C_{3-7}$ cycloalkylcarbonyl, a $C_{2-10}$ alkenylcarbonyl, a $C_{2-10}$ alkynylcarbonyl, an arylcarbonyl, an aralkylcarbonyl, a $C_{7-15}$ polycyclo-$C_{0-3}$ alkylcarbonyl, a $C_{1-16}$ alkyloxycarbonyl, a polyfluoro-$C_{1-16}$ alkyloxycarbonyl, a $C_{3-7}$ cycloalkyloxycarbonyl, a $C_{2-16}$ alkenyloxycarbonyl, a $C_{2-16}$ alkynyloxycarbonyl, an aryloxycarbonyl, a $C_{3-7}$ cycloalkyl-$C_{1-6}$ alkyloxycarbonyl, an aralkyloxycarbonyl, a $C_{1-10}$ alkylaminocarbonyl, a $C_{3-7}$ cycloalkylaminocarbonyl, a $C_{2-10}$ alkenylaminocarbonyl, a $C_{2-10}$ alkynylaminocarbonyl, an arylaminocarbonyl, an aralkylaminocarbonyl, a $C_{1-10}$ alkylsulfonyl, a $C_{3-7}$ cycloalkylsulfonyl, a $C_{2-10}$ alkenylsulfonyl, a $C_{2-10}$ alkynylsulfonyl, an arylsulfonyl, an aralkylsulfonyl, a $C_{7-15}$ polycyclo-$C_{0-3}$ alkylsulfonyl, a $C_{1-10}$ alkylaminosulfonyl, a $C_{3-7}$ cycloalkyaminosulfonyl, a $C_{2-10}$ alkenylaminosulfonyl, a $C_{2-6}$ alkynylaminosulfonyl, an arylaminosulfonyl or an aralkylaminosulfonyl), $R^7$ is a hydrogen atom, a $C_{1-6}$ alkyl group, a $C_{3-7}$ cycloalkyl group or an aralkyl group, or a pharmaceutically acceptable salt thereof or an N-oxide thereof, or a hydrate thereof.

4. An aryl-substituted alicyclic compound of the following formula (Ia), or a pharmaceutically acceptable salt thereof or an N-oxide thereof, or a hydrate thereof,

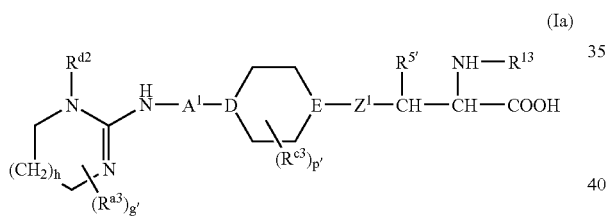

(Ia)

wherein $A^1$ is a group selected from the following formulae:

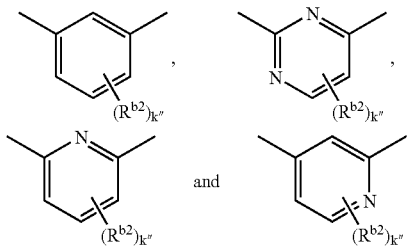

and ($R^{b2}$ is the same or different, and each is a hydrogen atom, a fluorine atom, a chlorine atom, a hydroxy group, a methyl group, a methoxy group, a phenyl group, a methoxycarbonyl group, a carboxyl group, an acetoxy group, an acetylamino group, a nitro group, a cyano group, a trifluoromethyl group or a trifluoromethoxy group, k" is 1 or 2), $Z^1$ is —$CONH$—, —$NHCO$— or —$COCH_2$—, $R^{d2}$ is a hydrogen atom, an acetyl group, a propionyl group, a methoxycarbonyl group, an ethoxycarbonyl group or a tert-butoxycarbonyl group, D and E are the same or different, and each is —CH— or a nitrogen atom, when E is a nitrogen atom, then $Z^1$ is —$CONH$— or —$COCH_2$—, $R^{a3}$ is the same or different, and each is a hydrogen atom, a fluorine atom, a hydroxy group, a methyl group, a methoxy group, a trifluoromethyl group or a trifluoromethoxy group, g' is 1 or 2, h' is an integer of 0 to 2, $R^{c3}$ is the same or different, and each is a hydrogen atom or a methyl group, or two $R^{c3}$ groups may combine to form —$(CH_2)_t$—, p' is 1 or 2, t is an integer of 1 to 3, $R^{5'}$ is a hydrogen atom, $R^{13}$ is a $C_{1-10}$ alkyloxycarbonyl group, a polyfluoro-$C_{1-10}$ alkyloxycarbonyl group, a $C_{3-7}$ cycloalkyloxycarbonyl group, a $C_{2-10}$ alkenyloxycarbonyl group, a $C_{2-10}$ alkynyloxycarbonyl group, an aryloxycarbonyl group, a $C_{3-7}$ cycloalkyl-$C_{1-6}$ alkyloxycarbonyl group, an aralkyloxycarbonyl group, a $C_{1-10}$ alkylaminocarbonyl group, a $C_{3-7}$ cycloalkylaminocarbonyl group, a $C_{2-10}$ alkenylaminocarbonyl group, a $C_{2-10}$ alkynylaminocarbonyl group, an arylaminocarbonyl group, an aralkylaminocarbonyl group, an arylsulfonyl group, an aralkylsulfonyl group or a $C_{7-15}$ polycyclo-$C_{0-3}$ alkylsulfonyl group, provided that in the above definition, the alkyl group, the cycloalkyl group, the alkenyl group, the alkynyl group and the alkyl moiety of the aralkyl group may optionally be substituted by 1 to 3 atoms or groups selected from a halogen, a $C_{1-3}$ alkyloxy, an amino and a hydroxy, and the aryl group and the aryl moiety may optionally be substituted by 1 to 3 atoms or groups selected from a halogen, a methyl, an ethyl, a propyl, a butyl, a $C_{3-7}$ cycloalkyl, an aryl, an aralkyl, an amino, a formylamino, an acetylamino, a dimethylamino, a dimethylaminomethyl, an aryl carbonylamino, a $C_{1-4}$ alkyloxy, a carboxyl, a $C_{1-3}$ alkyloxycarbonyl, a hydroxy, a hydroxymethyl, a cyano, a nitro, a trifluoromethyl, an acetoxy and a trifluoromethoxy.

5. An aryl-substituted alicyclic compound of the following formula (Ib), or a pharmaceutically acceptable salt thereof, or a hydrate thereof,

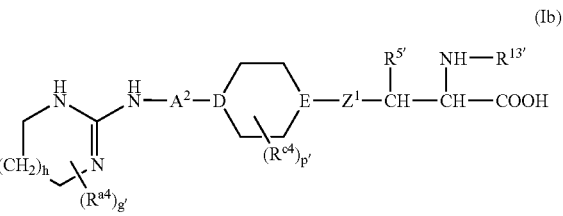

(Ib)

wherein $A^2$ is a group selected from the following formulae:

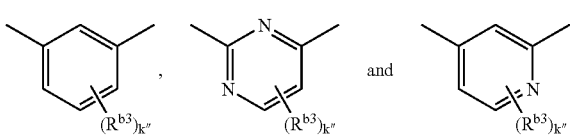

and ($R^{b3}$ is the same or different, and each is a hydrogen atom, a fluorine atom, a methyl group, a methoxy group, a trifluoromethyl group or a trifluoromethoxy group, k" is 1), $Z^1$ is —CONH—, —NHCO— or —COCH$_2$—, D and E are the same or different, and each is —CH— or a nitrogen atom, and when E is —CH—, then $Z^1$ is —CONH— or —NHCO—, and when E is a nitrogen atom, then $Z^1$ is —CONH— or —COCH$_2$—, $R^{a4}$ is the same or different, and each is a hydrogen atom, a fluorine atom, a hydroxy group or a methyl group, $R^{c4}$ is a hydrogen atom or a methyl group, $R^{5'}$ is a hydrogen atom, $R^{13'}$ is a $C_{1-10}$ alkyloxycarbonyl group, a polyfluoro-$C_{1-10}$ alkyloxycarbonyl group, a $C_{3-7}$ cycloalkyloxycarbonyl group, a $C_{2-10}$ alkenyloxycarbonyl group, a $C_{2-10}$ alkynyloxycatbonyl group, a $C_{3-7}$ cycloalkyl-$C_{1-6}$ alkyloxycarbonyl group, an aralkyloxycarbonyl group or an arylsulfonyl group, g' is 1 or 2, h' is an integer of 0 to 2, p' is 1 or 2, provided that in the above definition, the alkyl group, the cycloalkyl group, the alkenyl group, the alkynyl group, and the alkyl moiety of the aralkyl group may optionally be substituted by one atom or group selected from a halogen, a $C_{1-3}$ alkyloxy, an amino and a hydroxy, and the aryl group and the aryl moiety may optionally be substituted by 1 or 2 atoms or groups selected from a halogen, a methyl, an ethyl, a propyl, a butyl, a $C_{3-7}$ cycloalkyl, an aryl, an aralkyl, an amino, a formylamino, an acetylamino, a dimethylamino, a $C_{1-4}$ alkyloxy, a carboxyl, a hydroxy, a hydroxymethyl, a cyano, a nitro, a trifluoromethyl, an acetoxy and a trifluoromethoxy.

6. The aryl-substituted alicyclic compound according to claim 5, wherein E is —CH—, $Z^1$ is —CONH— or —NHCO—, and $R^{c4}$ is a hydrogen atom, or a pharmaceutically acceptable salt thereof or an N-oxide thereof, or a hydrate thereof.

7. The aryl-substituted alicyclic compound according to claim 5, wherein both D and E are simultaneously a nitrogen atom, and $Z^1$ is —CONH— or —COCH$_2$—, or a pharmaceutically acceptable salt thereof, or a hydrate thereof.

8. The aryl-substituted alicyclic compound according to claim 5, wherein D is —CH—, E is a nitrogen atom, $Z^1$ is —CONH— or —COCH$_2$—, and $R^{c4}$ is a hydrogen atom, or a pharmaceutically acceptable salt thereof, or a hydrate thereof.

9. An aryl-substituted alicyclic compound, which is selected from (2S)-2-benzyloxycarbonylamino-3-[[1-[3-(1,4,5,6-tetrahydropyrimidin-2-yl) aminophenyl]piperidin-4-yl]carbonylamino]propanoic acid, (2S)-2-benzyloxycarbonylamino-3-[[1-[2-(1,4,5,6-tetrahydropyrimidin-2-yl) amino-6-methylpyrimidin-4-yl]piperidin-4-yl]carbonylamino]propanoic acid, (2S)-2-benzyloxycarbonylamino-5-[4-[3-(1,4,5,6-tetrahydropyrimidin-2-yl)aminophenyl]piperazin-1-yl]-5-oxopentanoic acid, (2S)-2-benzyloxycarbonylamino-3-[[4-[3-(1,4,5,6-tetrahydropyrimidin-2-yl)-aminophenyl] piperazin-1-yl]carbonylamino]propanoic acid, (2S)-2-isopropoxycarbonylamino-3-[[1-[3-(1,4,5,6-tetrahydropyrimidin-2-yl)aminophenyl]piperidin-4-yl] carbonylamino]propanoic acid, (2S)-2-benzyloxycarbonylamino-3-[[1-[3-(1H-4,5,6,7-tetrahydro-1,3-diazepin-2-yl)aminophenyl]piperidin-4-yl] carbonylamino]propanoic acid, (2S)-2-benzyloxycarbonylamino-5-[4-[2-methoxy-5-(1,4,5,6-tetrahydropyrimidin-2-yl)aminophenyl]piperazin- 1-yl]-5-oxopentanoic acid, (2S)-2-benzyloxycarbonylamino-3-[[1-[2-methoxy-5-(1,4,5,6-tetrahydropyrimidin-2-yl)aniinophenyl]piperidin4-yl]carbonylamino]propanoic acid, (2S)-2-isobutoxycarbonylamino-3-[[1-[3-(1,4,5,6-tetrahydropyrimidin-2-yl)-aminophenyl]piperidin-4-yl]carbonylamino]propanoic acid, (2S)-2-hexyloxycarbonylamino-3-[[1-[3-(1,4,5,6-tetrahydropyrimidin-2-yl) -aminophenyl] piperidin-4-yl]carbonylamino]propanoic acid, (2S)-2-benzyloxycarbonylamino-3-[[1-[4-(1,4,5,6-tetrahydropyrimidin-2-yl)aminopyridin-2-yl]piperidin-4-yl] carbonylamino]-propanoic acid, (2S)-2-benzyloxycarbonylamino-3-[[1-[3-(4-hydroxy-1,4,5,6-tetrahydropyrimidin-2-yl)aminophenyl]piperidin-4-yl] carbonylamino]propanoic acid, (2S)-2-benzyloxycarbonylamino-3-[[1-[3-(4,4-dimethyl-1,4,5,6-tetrahydropyrimidin-2-yl)aminophenyl]piperidin-4-yl] carbonylamino]propanoic acid, (2S)-2-benzyloxycarbonylamino-3-[[1-[3-(4-fluoro-1,4,5,6-tetrahydropyrimidin-2-yl)aminophenyl]piperidin-4-yl] carbonylamino]propanoic acid, (2S)-2-benzyloxycarbonylamino-3-[[1-[4-methyl-3-(1,4,5,6-tetrahydropyrimidin-2-yl)aminophenyl]piperidin-4-yl] carbonylamino]propanoic acid, (2S)-2-(N'-hexylureido)-3-[[1-[3-(1,4,5,6-tetrahydropyrimidin-2-yl)aminophenyl] piperidin-4-yl]carbonylamino]propanoic acid, (2S)-2-(2-methoxyethoxycarbonylamino)-3-[[1-[3-(1,4,5,6-tetrahydropyrimidin-2-yl)aminophenyl]piperidin-4-yl] carbonylamino]propanoic acid, (2S)-2-butoxycarbonylamino-3-[[1-[3-(1,4,5,6-tetrahydropyrimidin-2-yl)aminophenyl]piperidin-4-yl] carbonylamino]propanoic acid, (2S)-2-octyloxycarbonylamino-3-[[1-[3-(1,4,5,6-tetrahydropyrimidin-2-yl)aminophenyl]piperidin-4-yl] carbonylamino]propanoic acid, (2S)-2-neopentyloxycarbonylamino-3-[[1-[3-(1,4,5,6-tetrahydropyrimidin-2-yl)aminophenyl]piperidin-4-yl] carbonylamino]propanoic acid, (2S)-2-benzyloxycarbonylamino-3-[[4-[3-(1,4,5,6-tetrahydropyrimidin-2-yl) -aminophenyl]cyclohexane] carbonylamino]propanoic acid, (2S)-2-benzyloxycarbonylamino-3-[[1-[5-fluoro-3-(1,4,5,6-tetrahydropyrimidin-2-yl)aminophenyl]piperidin-4-yl] carbonylamino]propanoic acid, (2S)-2-hexyloxycarbonylamino-5-[4-[3-(1,4,5,6-tetrahydropyrimidin-2-yl)aminophenyl]piperazin-1-yl]-5-oxopentanoic acid, (2S)-2-benzyloxycarbonylamino-3-[[1-[3-(2-imidazolin-2-yl)aminophenyl]piperidin-4-yl] carbonylamino]propanoic acid, (2S)-2-benzyloxycarbonylamino-3-[[1-[4-(4-fluoro-1,4,5,6-tetrahydropyrimidin-2-yl)aminopyridin-2-yl]piperidin-4-yl] carbonylamino]propanoic acid, (2S)-2-benzyloxycarbonylamino-3-[[1-[3-(4,4-difluoro-1,4,5,6-tetrahydropyrimidin-2-yl)aminophenyl]piperidin-4-yl] carbonylamino]propanoic acid, (2S)-2-isobutoxycarbonylamino-5-[4-[3-(1,4,5,6-tetrahydropyrimidin-2-yl)aminophenyl]piperazin- 1-yl]-5-oxopentanoic acid, (2S)-2-isobutoxycarbonylamino-3-[[1-[3-(5,5-dimethyl-1,4,5,6-tetrahydropyrimidin-2-yl) aminophenyl]piperidin-4-yl]carbonylamino]propanoic acid, (2S)-2-isobutoxycarbonylamino-3-[[1-[3-(5-fluoro-1,4,5,6-tetrahydropyrimidin-2-yl)aminophenyl]piperidin-4-yl]carbonylarnino]propanoic acid, (2S)-2-isobutoxycarbonylamino-3-[[1-[3-(5-hydroxy-1,4,5,6-tetrahydropyrimidin-2-yl)aminophenyl]piperidin-4-yl]carbonylamino]propanoic acid, (2S)-2-ethoxycarbonylamino-3-[[1-[3-(1,4,5,6-tetrahydropyrimidin-2-yl)aminophenyl]piperidin-4-yl]carbonylamino]propanoic acid, (2S)-2-decyloxycarbonylamino-3-[[1-[3-(1,4,5,6-tetrahydropyrimidin-2-yl)aminophenyl]piperidin-4-yl]carbonylamino]propasioic acid, (2S)-2-allyloxycarbonylamino-3-[[1-[3-(1,4,5,6-tetrahydropyrimidin-2-yl)aminophenyl]piperidin-4-yl]carbonylamino]propanoic acid, (2S)-2-benzyloxycarbonylamino-5-[4-[3-(5-fluoro-1,4,5,6-tetrahydropyrimidin-2-yl)aminophenyl]piperazin-1-yl]-5-oxopentanoic acid, (2S)-2-isobutoxycarbonylamino-5-[4-[3-(5-fluoro-1,4,5,6-tetrahydropyrimidin-2-yl)aminophenyl]piperazin-1-yl]-5-oxopentanoic acid, (2S)-2-hexyloxycarbonylamino-5-[4-[3-(5-fluoro-1,4,5,6-tetrahydropyrimidin-2-yl)aminophenyl]piperazin-1-yl]-5-oxopentanoic acid, and (2S)-2-benzyloxycarbonylamino-5-[4-[2-fluoro-5-(1,4,5,6-tetrahydropyrimidin-2-yl)aminophenyl]piperazin-1-yl]-5-oxopentanoic acid, or a pharmaceutically acceptable salt thereof, or a hydrate thereof.

10. An aryl-substituted alicyclic compound, which is selected from (2S)-2-benzyloxycarbonylamino-3-[N-[8-[3-(1,4,5,6-tetrahydropyrimidin-2-yl)-aminophenyl]-8-azabicyclo[3.2.1]octan-3-yl]carbamoyl]propanoic acid, (2S)-2-ethoxycarbonylamino-3-[[8-[3-(5,5-difluoro-1,4,5,6-tetrahydropyrimidin-2-yl)aminophenyl]-8-azabicyclo[3.2.1]octan-3-yl]carbonylamino]propanoic acid, (2S)-3-[[1-[5-fluoro-3-(1H-4,5,6,7-tetrahydro-1,3-diazepin-2-yl)aminophenyl]piperidin-4-yl]carbonylamino]-2-(isobutoxycarbonylamino)propanoic acid, (2S)-2-isopropoxycarbonylamino-5-[4-[5-(1H-4,5,6,7-tetrahydro-1,3-diazepin-2-yl)amino-2-methoxyphenyl]-piperazin-1-yl]-5-oxopentanoic acid, (2S)-5-[4-[2-fluoro-5-(1H-4,5,6,7-tetrahydro-1,3-diazepin-2-yl)amino]piperazin-1-yl]-2-(isobutoxycarbonylamino)-5-oxopentanoic acid, (2S)-2-butoxycarbonylamino-5-[4-[4-(1H-4,5,6,7-tetrahydro- 1,3-diazepin-2-yl)aminopyridin-2-yl]piperazin-1-yl]-5-oxopentanoic acid, (2S)-2-benzyloxycarbonylamino-3-[[1-[4-(1H-4,5,6,7-tetrahydro-1,3-diazepin-2-yl)aminopyridin-2-yl]piperidin-4-yl]carbonylamino]propanoic acid, (2S)-2-hexyloxycarbonylamino-3-[[1-[4-(2-imidazolin-2-yl)aminopyridin-2-yl]piperidin-4-yl]carbonylamino]-propanoic acid, (2S)-2-isopropoxycarbonylamino-3-[[4-[4-(2-imidazolin-2-yl)aminopyridin-2-yl]piperazin-1-yl]carbonylamino]propanoic acid, (2S)-2-benzyloxycarbonylamino-3-[[2,6-dimethyl-4-[3-(1,4,5,6-tetrahydropyrimidin-2-yl)aminophenyl]piperazin-1-yl]carbonylamino]-propanoic acid, (2S)-2-hexyloxycarbonylamino-3-[[2,5-dimethyl-4-[3-(5-fluoro-1,4,5,6-tetrahydropyrimidin-2-yl)aminophenyl]piperazin-1-yl]carbonylamino]propanoic acid, (2S)-2-isobutoxycarbonylamino-5-[2,6-dimethyl-4- [3-(5,5-dimethyl- 1,4,5,6-tetrahydropyrimidin-2-yl)aminophenyl]piperazin-1-yl]-5-oxopentanoic acid, (2S)-2-benzyloxycarbonylamino-5-[3,5-dimethyl-4-[3-(5,5-difluoro-1,4,5,6-tetrahydropyrimidin-2-yl)aminophenyl]piperazin-1-yl]-5-oxopentanoic acid, (2S)-2-hexyloxycarbonylamino-3-[[3,5-dimethyl-4-[3-(5-hydroxy-1,4,5,6-tetrahydropyrimidin-2-yl)aminophenyl]piperazin-1-yl]carbonylamino]propanoic acid, (2S)-2-isobutoxycarbonylamino-3-[[2,2-dimethyl-4-[3-(5-hydroxy-1,4,5,6-tetrahydropyrimidin-2-yl)aminophenyl]piperazin-1-yl]-carbonylamino]propanoic acid, (2S)-2-benzyloxycarbonylamino-5-[2-methyl-4-[3-(5-fluoro-1,4,5,6,-tetrahydropyrimidin-2-yl)aminophenyl]-piperazin-1-yl]-5-oxopentanoic acid, and (2S)-2-isopropoxycarbonyl-amino-5-[3-methyl-4-[3-(5-fluoro-1,4,5,6,-tetrahydropyrimidin-2-yl) -aminophenyl]piperazin-1-yl]-5-oxopentanoic acid, or a pharmaceutically acceptable salt thereof, or a hydrate thereof.

11. A pharmaceutical composition, which comprises as an active ingredient an aryl-substituted alicyclic compound as set forth in claim 1, or a pharmaceutically acceptable salt thereof, or an N-oxide thereof, or a hydrate thereof, and a pharmaceutically acceptable carrier or diluent.

12. A pharmaceutical composition, which comprises as an active ingredient an aryl-substituted alicyclic compound as set forth in claim 4, or a pharmaceutically acceptable salt thereof, or an N-oxide thereof, or a hydrate thereof, and a pharmaceutically acceptable carrier or diluent.

13. A pharmaceutical composition, which comprises as an active ingredient an aryl-substituted alicyclic compound as set forth in claim 5, or a pharmaceutically acceptable salt thereof, or an N-oxide thereof, or a hydrate thereof, and a pharmaceutically acceptable carrier or diluent.

14. A pharmaceutical composition, which comprises as an active ingredient an aryl-substituted alicyclic compound as set forth in claim 9, or a pharmaceutically acceptable salt thereof, or an N-oxide thereof, or a hydrate thereof, and a pharmaceutically acceptable carrier or diluent.

15. A pharmaceutical composition, which comprises as an active ingredient an aryl-substituted alicyclic compound as set forth in claim 10, or a pharmaceutically acceptable salt thereof, or an N-oxide thereof, or a hydrate thereof, and a pharmaceutically acceptable carrier or diluent.

16. A method of treatment of rheumatoid arthritis, which comprises administering an effective amount of the pharmaceutical composition as set forth in claim 11 to a patient in need thereof.

* * * * *